United States Patent
Wright et al.

(10) Patent No.: US 11,169,152 B2
(45) Date of Patent: Nov. 9, 2021

(54) FUNCTION-BASED PROBES FOR ENVIRONMENTAL MICROBIOME ANALYSIS AND METHODS OF MAKING AND USING THE SAME

(71) Applicant: Battelle Memorial Institute, Richland, WA (US)

(72) Inventors: Aaron T. Wright, Richland, WA (US); Susan Ramos-Hunter, Richland, WA (US); Natalie C. Sadler, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 264 days.

(21) Appl. No.: 16/132,266

(22) Filed: Sep. 14, 2018

(65) Prior Publication Data
US 2019/0086410 A1   Mar. 21, 2019

Related U.S. Application Data

(60) Provisional application No. 62/591,697, filed on Nov. 28, 2017, provisional application No. 62/559,212, filed on Sep. 15, 2017.

(51) Int. Cl.
| | |
|---|---|
| *G01N 33/573* | (2006.01) |
| *C12Q 1/54* | (2006.01) |
| *C07H 15/203* | (2006.01) |
| *G01N 33/569* | (2006.01) |

(52) U.S. Cl.
CPC ......... *G01N 33/573* (2013.01); *C07H 15/203* (2013.01); *C12Q 1/54* (2013.01); *G01N 33/56911* (2013.01); *G01N 2333/908* (2013.01); *G01N 2333/924* (2013.01); *G01N 2400/00* (2013.01)

(58) Field of Classification Search
None
See application file for complete search history.

(56) References Cited

U.S. PATENT DOCUMENTS

2011/0020837 A1   1/2011   Haberkant et al.

FOREIGN PATENT DOCUMENTS

| EP | 2 482 077 | 8/2012 |
| WO | WO 2014/031498 | 2/2014 |

OTHER PUBLICATIONS

Sadler et al., "Activity-based protein profiling of microbes," *Current Opinion in Chemical Biology*, vol. 24, pp. 139-144, Dec. 19, 2014.
Chauvigne-Hines et al., "Suite of Activity-Based Probes for Cellulose-Degrading Enzymes," *J. Am. Chem. Soc.*, vol. 134, pp. 20521-20532, Nov. 24, 2012.
Bottcher et al., "β-Lactams and β-lactones as activity-based probes in chemical biology," *MedChemComm*, No. 3, pp. 408-417, Jan. 4, 2012.
Lockhart et al., "Screening-based discovery of *Aspergillus fumigatus* plant-type chitinase inhibitors," *FEBS Letters*, No. 588, pp. 3282-3290, Jul. 22, 2014.
Hirose et al., "Review: Recent development of two chitinase inhibitors, Argifin and Argadin, produced by soil microorganisms," *Proc. Jpn. Acad. Ser. B*, 86(2): 85-102, Feb. 2010.
Invitation to Pay Additional Fees issued by International Searching Authority dated Feb. 12, 2019, for International Application No. PCT/US2018/051230.
Hong et al., "Live-cell stimulated raman scattering imaging of alkyne-tagged biomolecules," *Angew. Chem. Int. Ed.*, 53(23): 5827-5831, 2014.
International Search Report and Written Opinion issued for International Application No. PCT/IB2018/058935 dated Jun. 27, 2019.
Liu et al., "Exploring the binding proteins of glycolipids with bifunctional chemical probes," *Angew. Chem. Int. Ed.*, 55(46): 14330-14334, Nov. 7, 2016.
Wright et al., "A suite of activity-based probes for human cytochrome P450 enzymes," *J. Am. Chem. Soc.*, 131(30): 10692-10700, Aug. 5, 2009.

*Primary Examiner* — Layla D Berry
(74) *Attorney, Agent, or Firm* — Klarquist Sparkman, LLP

(57) ABSTRACT

Probe embodiments for identifying analytes involved in biofuel or bioenergy production, bioremediation, or nutrient cycling as well as methods of making and use are described herein. In some embodiments, probes identifying cellulose degradation and/or sugar transport, lignin or chitin degradation, or peptide or toxin metabolism are included. In some embodiments, probes for identifying analytes in a soil sample are included in the compositions and methods disclosed herein.

17 Claims, 14 Drawing Sheets

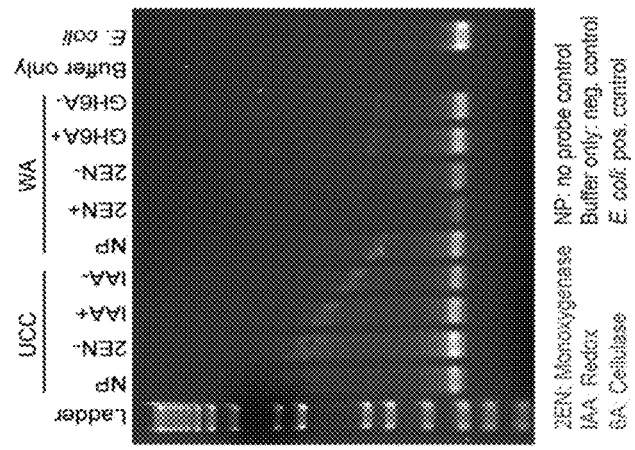
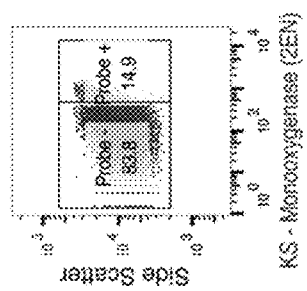
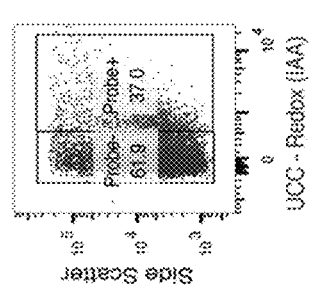
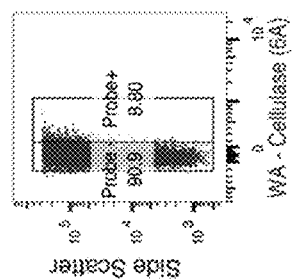
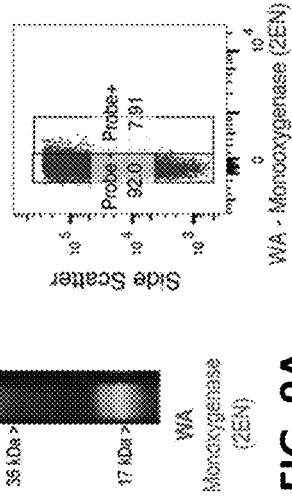
FIG. 9A  FIG. 9B  FIG. 9C  FIG. 9D  FIG. 9E  FIG. 9F

FUNCTION-BASED PROBES FOR ENVIRONMENTAL MICROBIOME ANALYSIS AND METHODS OF MAKING AND USING THE SAME

CROSS REFERENCE TO RELATED APPLICATIONS

This application claims the benefit of earlier filing date of U.S. Provisional Patent Application No. 62/591,697, filed on Nov. 28, 2017, and U.S. Provisional Patent Application No. 62/559,212, filed on Sep. 15, 2017; each of these prior applications is incorporated herein by reference in its entirety.

ACKNOWLEDGMENT OF GOVERNMENT SUPPORT

This invention was made with Government support under Contract DE-AC05-76RL01830 awarded by the U.S. Department of Energy. The Government has certain rights in the invention.

FIELD

The present disclosure concerns function-based probes and methods of using such probes for function-dependent separation, identification, and characterization of analytes present in environmental microbiomes.

BACKGROUND

There is a growing research interest in avoiding characterizing microbial communities by genomes or transcriptomes alone. However, current techniques using fluorescence in situ hybridization (FISH) for sorting microbes from microbiomes based upon gene content still almost universally fail to provide a sorting mechanism based solely upon function. This technique, and many others, are based upon labeling of genes or amino acids; however, the presence of a gene or an amino acid does not necessarily equal function. New techniques are needed that identify, separate, and quantify analyte species (for example, microbes, enzymes, toxins, and the like) present in biological environments (for example, soil, water, air, cells, and the like) so that such species and their functions can be determined.

SUMMARY

Disclosed herein are probe embodiments that can be used to identify and characterize analytes involved in, for example, cellulose degradation, chitin degradation, lignin degradation, sugar and small aromatic compound transport, toxin detection, and the like. In some embodiments, the probe can have a structure according to formulas described herein. Also disclosed herein are embodiments of a kit comprising a substrate and a probe according to any of the formulas disclosed herein wherein the substrate comprises a surface modified with a functional group configured to covalently bind with the anchor group of the probe.

Also disclosed herein are embodiments of methods of using the probes. In some embodiments, the method comprises exposing a sample to a probe embodiment described herein or a kit comprising the probe to label at least one analyte present in the sample with the probe thereby forming a probe-analyte conjugate. In some embodiments, the method can further comprise (i) exposing the sample to an energy source to promote formation of the probe-analyte conjugate; (ii) exposing the sample to a reagent comprising a detectable moiety configured to covalently bind with a pTag group of the probe; (iii) sorting or isolating the probe-analyte conjugate or a microbe comprising the probe-analyte conjugate; (iv) identifying the analyte or the microbe with the probe-analyte conjugate; or (v) any combination of (i)-(iv). Also disclosed herein is a method of altering microbial metabolism in an environment, comprising: exposing a sample from the environment to a probe embodiment or kit disclosed herein; allowing the probe to interact with at least one microbial protein present in the sample, wherein the at least one microbial protein comprises at least one specific metabolic function; determining the presence of the at least one microbial protein in the sample that is bound to the probe; evaluating the activity of the at least one microbial protein bound to the probe; and altering microbial metabolism in the environment by (i) enriching the environment with the at least one microbial protein or a microbe containing the at least one microbial protein; (ii) reducing the amount of the at least one microbial protein or an amount of a microbe containing the at least one microbial protein in the environment; (ii) increasing the at least one specific metabolic function; or (iv) reducing the at least one specific metabolic function. In some embodiments, the at least one specific metabolic function comprises nutrient cycling, bioremediation, or producing biofuel or bioenergy and the at least one microbial protein is a cellulose, hemicellulase, xylanase, glucosidase, sulfatase, phosphatase, protease, glucosidase, lytic polysaccharide monooxygenase (LPMO), or chitinase.

The foregoing and other objects, and features of the present disclosure will become more apparent from the following detailed description, which proceeds with reference to the accompanying figures.

BRIEF DESCRIPTION OF THE DRAWINGS

FIG. 7A shows standard probe labeling, which may include UV irradiation, and wherein probes label target extra- or intracellular proteins in live cells, followed by cell lysis, biotin attachment, labeled proteins enrichment and digestion, and LC-MS analysis of labeled proteins; FIG. 7B shows a "no probe" control wherein all steps from probe labeling are followed without the addition of a probe embodiment to thereby identify any non-selective protein-streptavidin binding; FIG. 7C shows the addition of a chemical compound comprising functional groups of probe embodiments disclosed herein, but without a corresponding binding group to thereby identify any potential background binding from the functional groups of the probe (for example, alkyne or diazirine portions); and FIG. 7D shows competition experiments in which a native compound is added to a probe embodiment and competitively inhibits probe binding to proteins, which demonstrates the function-based probes are forming native substrate-protein interactions.

FIGS. 9A-9F show results obtained from probe-dependent labeling and isolation of uncultivated microbes; FIG. 9A shows microbial monooxygenase proteins labeled in the WA soil community; FIG. 9B-9E show flow cytometry of probed communities wherein "no-probe" controls were used to distinguish between probe-positive and probe-negative events; and FIG. 9F shows gel separation of PCR-amplified 16S rRNA sequences from sorted cells, wherein "+" indicates probe-labeled sorted cells, "–" indicates unlabeled sorted cells, "IAA" indicates a redox probe, "2EN" indicates a monooxygenase probe, "6A" indicates a cellulase probe, "buffer only" indicates a negative control, "*E. coli*" indicates a positive control, and "NP" indicates no probe.

FIG. 11A shows a structure of GlcA-ABP and shows fluorescence (top) and coomassie-stained (bottom) SDS-PAGE analyses of GlcA-ABP-labeled β-glucuronidases tagged with tetramethylrhodamine azide via CuAAC; FIG. 11B shows quantification of labeling intensity using ImageJ, wherein the columns indicate the mean, and error bars indicate the standard error of the mean, * indicates an adjusted p=0.0203, and ** indicates an adjusted p=0.0047 by repeated measures one-way ANOVA with Dunnett's multiple comparisons test, n=3; FIG. 11C shows *E. coli* lysate (WT BW25113, ΔuidA pET32c, or the complement, ΔuidA puidA) labeled with GlcA-ABP at various concentrations, wherein labeled proteins were tagged with tetramethylrhodamine azide via CuAAC and analyzed via SDS-PAGE and the labeled protein was visualized via fluorescence (left), and total protein was imaged via coomassie blue stain (right); FIG. 11D shows whole-cell *E. coli* labeled with GlcA-ABP, and the labeled cells were tagged with CF®640R; FIG. 11E shows histograms of *E. coli* only (top left), *L. plantarum* only (top middle), or a mixture of the two (top right and bottom) labeled with GlcA-ABP, the cysteine-reactive IAA-ABP, or vehicle-only (DMSO), which is representative of three biological replicates.

FIGS. 14A-14O show that the GlcA-ABP+ population shifts upon antibiotic exposure; FIG. 14A shows a phylogenetic distribution of GlcA-ABP+ taxa in control mice (triangles) compared with vancomycin-treated mice (squares) and wherein the taxa are considered differentially abundant where Benjamini-Hochberg adjusted p<0.05 by Welch's t test or by G-test (n=3 pairs)

DETAILED DESCRIPTION

I. Overview of Terms

Figure 1:
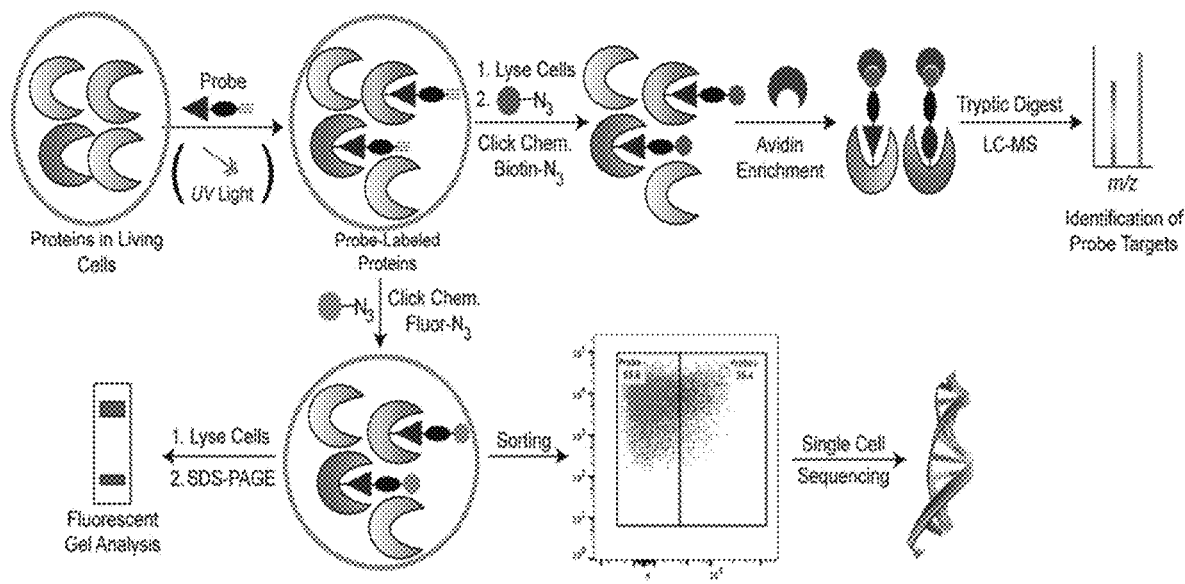
FIG. 1 shows an embodiment of a method using function-based probe labeling for protein target characterization, fluorescence-activated cell sorting, and single cell genome sequencing, wherein a probe embodiment is added to a sample and forms an irreversible bond to analytes that recognize the probe, after which a detectable label can be attached to the probe-analyte conjugate to facilitate sorting and/or gel analyses (bottom route) or enrichment by bead-based affinity capture and subsequent proteomic characterization by LC-MS (top route).

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Compounds disclosed herein may contain one or more asymmetric elements such as stereogenic centers, stereogenic axes and the like, for example asymmetric carbon atoms, so that the chemical conjugates can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. Additionally, certain structures illustrated herein may include a wavy line ("⌇") going through bond

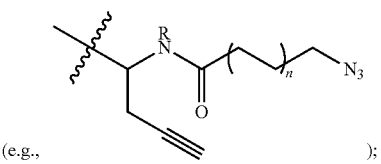

(e.g., );

the wavy line in this context is used to indicate a bond disconnection.

All forms (for example solvates, optical isomers, enantiomeric forms, polymorphs, free compound and salts) of a probe may be employed either alone or in combination.

To facilitate review of the various embodiments of the disclosure, the following explanations of specific terms are provided. Certain functional group terms include a "−" symbol at the beginning of the functional group formula; this symbol is not a part of the functional group, but instead denotes how the functional group connects to the formulas described herein. For example, a functional group with a formula "—OC(O)$R^b$" is attached to an atom of the functionalized compound by the oxygen atom of the functional group that is next to the "−" symbol.

Acyloxy: —OC(O)$R^b$, wherein $R^b$ is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aromatic: An aromatic group that is or can be coupled to a probe disclosed herein, wherein the aromatic group is or becomes coupled through an aliphatic group.

Aliphatic-aryl: An aryl group that is or can be coupled to a probe disclosed herein, wherein the aryl group is or becomes coupled through an aliphatic group.

Aliphatic-heteroaromatic: A heteroaromatic group that is or can be coupled to a probe disclosed herein, wherein the heteroaromatic group is or becomes coupled through an aliphatic group.

Aliphatic-heteroaryl: A heteroaryl group that is or can be coupled to a probe disclosed herein, wherein the heteroaryl group is or becomes coupled through an aliphatic group.

Alkenyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (for example, cycloalkenyl), cis, or trans (for example, E or Z).

Alkoxy: —O-aliphatic, such as —O-alkyl, —O-alkenyl, or —O-alkynyl, with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (for example, alkane). An alkyl group can be branched, straight-chain, or cyclic (for example, cycloalkyl).

Alkynyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (for example, cycloalkynyl).

Alkylaryl/Alkenylaryl/Alkynylaryl: An aryl group that is or can be coupled to a probe disclosed herein, wherein the aryl group is or becomes coupled through an alkyl, alkenyl, or alkynyl group, respectively.

Alkylheteroaryl/Alkenylheteroaryl/Alkynylheteroaryl: A heteroaryl group that is or can be coupled to a probe disclosed herein, wherein the heteroaryl group is or becomes coupled through an alkyl, alkenyl, or alkynyl group, respectively.

Amide: —C(O)NR$^b$R$^c$ wherein each of R$^b$ and R$^c$ independently is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Amine: —NR$^b$R$^c$, wherein each of R$^b$ and R$^c$ independently is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Ammonia monooxygenase (AMO): An enzyme that catalyzes the oxidation of ammonia to hydroxylamine (for example, Timmis et al., eds., *Handbook of Hydrocarbon and Lipid Microbiology*, ch. 7, 2505-2514, 2010, incorporated herein by reference in its entirety). In some examples, AMO can be used for bioremediation (for example, aromatic hydrocarbon bioremediation).

Anchor Group: A functional group that can be used to attach a probe embodiment to a surface of a substrate component. In some embodiments, the anchor group can be a clickable functional group, an activated ester (e.g., NHS-ester), a carboxylic acid, a halide, or an alkyl halide.

Aromatic: A cyclic, conjugated group or moiety of, unless specified otherwise, from 5 to 15 ring atoms having a single ring (for example, phenyl, pyridinyl, or pyrazolyl) or multiple condensed rings in which at least one ring is aromatic (for example, naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

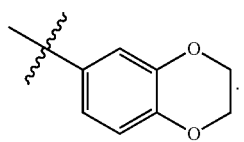 [SMILES: *c1ccc2c(c1)OCCO2]

However, in certain examples, context or express disclosure may indicate that the point of attachment is through a non-aromatic portion of the condensed ring system. For example,

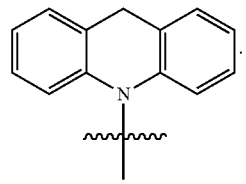 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (for example, S, O, N, P, or Si), such as in a heteroaryl group or moiety.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, aryl, heteroaryl, other functional groups, or any combination thereof. In some embodiments, the aryl ring is selected from, but not limited to, phenyl, naphthyl, anthracenyl, indenyl, azulenyl, fluorenyl, tetracyanoanthaquinodimethyl, and the like.

Benzyl carbonyl: —C(O)Ph.

Biomass: An organic substance that can be used to obtain energy (for example, biofuel; Liao et al., *Nat Rev Microbiol*, 14(5):288-304, 2016, incorporated by reference herein in its entirety). Biomass can include matter from any living organism, including plants, animals, or microbes, such as algae. Examples of biomass include direct sources, such as plants, fungi, and algae, and indirect sources, such as waste from living organisms. Exemplary examples of biomass include arable crops or products thereof (for example, sugarcane, corn, soybean, canola, or sugar, starch, or oil derived therefrom), lignocellulosic or woody biomass (for example, plant dry matter, such as plant matter with lignins, cellulose, and/or hemicellulose, for example, from terrestrial plants, including trees, such as poplar trees, bushes, and grass, such as switch grass and elephant grass, or agricultural waste or byproducts, including from corn, sugarcane, straw, and forestry), agricultural residues (for example, field and process residues, such as stalks, stems, leaves, seed pods, husks, seeds, molasses, roots, and bagasse), plant or animal waste, algae, or products therefrom.

Biofuel and bioenergy: Energy or fuel derived (for example, directly, such as from plants yeast, fungi, or algae, or indirectly, such as from plant waste or byproducts, for example, from agricultural, commercial, domestic, or industrial use; Meadows et al., *Biotechnol J*, 13(1), 1-13, 2018; Jiang et al., *Bioresour Bioprocess*, 4(1):11, 2017, both of which are incorporated by reference herein in their entireties) from biological processes, such as agriculture or anaerobic digestion. Biofuel can be non-renewable or renewable (for example, biofuel derived from photosynthetic processes, such as in algae or plants, or conversion of biomass into usable energy, such as thermal, chemical, and biochemical conversion). Exemplary forms of biofuel include, but are not limited to, biofuel in liquid, gas, or solid form, for example, first generation (for example, biofuel derived from food crops or crops grown on arable land), second generation (for example, biofuel derived from biomass), third generation (for example, biofuel derived from algae or algae products), or fourth generation biofuels (for example, biofuels derived using non-arable land, such as electrofuels, photobiological solar fuels, and carbon-neutral fuels, for example, using transesterification).

Bioprocessing: A process that uses complete living cells or their components (for example, microbes, such as bacteria and fungi; cells, such as cells from plants, yeast, insects, and animals; enzymes, such as enzymes involved in energy and/or product generation; and recombinant DNA; National Research Council (US) Committee on Bioprocess Engineering, *Putting Biotechnology to Work: Bioprocess Engineering*, Washington D.C., National Academies Press (US), 1992, incorporated by reference herein in its entirety) to obtain desired products. Bioprocessing applications vary and include the production of fuels and energy (for example, renewable and/or clean energy); agriculture and/or aquaculture (for example, damage control and nutrient production, such as microbes to reduce damage from temperature, pests, and chemicals, such as metals, or to enhance nutrient availability and/or uptake); and product manufacture (for example, chemicals, such as organic acids, oxygenated chemicals, fuel additives, and low-molecular-weight chemical and biological tools, such as biopharmaceutical tools; biopharmaceuticals, such as therapeutic proteins, polysaccharides, and antibiotics; food products, such as additives and processing aids; pesticides, such as biodegradable and environmentally compatible pesticides; fiber, such as from renewable sources; bioremediation or environmental-management aids, such as for controlling or remediating toxic wastes). In some examples, bioprocessing can occur in a specific environment (for example, a bioprocessing environment). For example, bioprocessing can occur in a bioreactor, cellular, soil, or aqueous environment.

Bioremediation: A process for treating a contaminated environment or media (for example, water, soil, subsurface material, or air). In some examples, bioremediation includes supporting, stimulating, or initiating microbe growth or habitation of a contaminated environment or media, for example, to treat waste (for example, wastewater, industrial waste, or solid waste) or degrade pollutants or contaminants (for example, reduced pollutants, such as hydrocarbon, phenol, aliphatic, alicyclic, or aromatic compounds; oxidized pollutants, such as chlorine-containing compounds, energetics or explosives, or nitrates; pesticides or organo-phosphonates; or heavy metals). In some examples, bioremediation includes treating a contaminated environment or media using at least one specific metabolic function, such as at least one specific metabolic function of enzymes, proteins, or microbes (for example, microbial enzymes or proteins or microbes expressing at least one enzyme or protein). In some examples, the contamination includes a polycyclic hydrocarbon or petroleum hydrocarbon (for example, benzene, toluene, ethyl benzene, or xylene); alkane hydrocarbon (for example, methane, ethane, propane, butane, pentane, hexane, heptane, octane, nonane, decane, undecane, dodecane, tridecane, tetradecane, pentadecane, hexadecane, heptadecane, octadecane, nonadecane, or eicosane); or chlorohydrocarbon (for example, chlorinated hydrocarbons, such as methyl chloride, methylene chloride, chloroform, ethyl chloride, or methylchloroform).

Carboxyl: —C(O)OR$^b$, wherein R$^b$ is aliphatic, aryl, heteroaliphatic, aliphatic-aryl, heteroaryl, aliphatic-heteroaryl, heteroaliphatic-aryl, heteroaliphatic-heteroaryl, hydrogen, and any combination thereof.

Cellulose: A linear chain polysaccharide that can include hundreds or thousands of β-1,4-linked glucose units and can be degraded chemically or enzymatically (for example, by cellulases, enzymes that degrade cellulose and related polysaccharides, for example, to produce monosaccharides or disaccharides, such as cellobiose, for example, by the cellulases cellobiohydrolases and β-glucosidases; for example, Zhang and Zhang, *Bioprocessing technologies in biorefinery for sustainable production of fuels, chemicals, and polymers*, Wiley, Hoboken, ch. 8-10, 131-192, 2013; Bhat and Bhat, *Biotechnol Adv,* 15(3-4):583-620, 1997, both of which are incorporated herein by reference in their entireties). Cellulose is found in plant cell walls and can also be made by some animals and bacteria. In some examples, cellulose is used as feedstock or a source of energy in bioenergy or biofuel production.

Chitin: A fibrous polysaccharide polymer found in, for example, arthropod exoskeleton and fungi cell walls, which plays a role in nutrient cycling (for example, carbon and nitrogen cycling). Chitin can be enzymatically degraded, for example, by chitinases (for example, hydrolytic enzymes that can reduce chitin into monosaccharides and oligosaccharides) and lytic polysaccharide monooxygenases (LPMO; for example, microbial oxidative copper enzymes involved in the degradation of polysaccharides, such as recalcitrant polysaccharides). In some examples, complete lysis of insoluble chitin polymer occurs in three steps: insoluble chitin polymer is cleaved into water soluble oligomers by LPMO and chitinases; the oligomers are degraded into dimers, for example, by chitinases, such as in the glycoside hydrolase family 18; and β-N-acetyl-hexosaminidases cleave dimers into monomers (Beier and Bertilsson, *Front Microbiol,* 4:149, 2013; incorporated herein by reference in its entirety).

Climate change: Includes various alterations to the environment, such as on global and local scales, for example, as a result of natural or human activities. Some examples of alterations to the environment include changes to atmospheric $CO_2$ levels (for example, increased atmospheric $CO_2$ levels), temperature (for example, increased global temperatures with increased or decreased local temperatures), or water levels (for example, increased or decreased local water levels, such as drought or decreased snowpack or increased precipitation or streamflow).

Click Chemistry: Chemical synthetic methods for making compounds using reagents that can be joined together using efficient reagent conditions and that can be performed in benign solvents or solvents that can be removed or extracted using facile methods, such as evaporation, extraction, or distillation. A representative example of click chemistry is a reaction that couples an azide and an alkyne to form a triazole.

Clickable Functional Group: A functional group that can be used in a click chemistry reaction to form a product. In some embodiments, the clickable functional group is an azide or an alkyne.

Ester: —C(O)OR$^b$, wherein R$^b$ is selected from hydrogen, aliphatic, aryl, heteroaliphatic, aliphatic-aryl, heteroaryl, aliphatic-heteroaryl, heteroaliphatic-aryl, heteroaliphatic-heteroaryl, or any combination thereof.

Environment: Surroundings or habitat, such as the native habitat of an organism or community (for example, the native habitat of a microbe or community of microbes). Environments can vary relative to an organism and community and include, for example, a bioreactor, physical (for example, cellular), soil, or aqueous environment.

The term "natural environment" is used to describe non-artificial or non-man-made surroundings of living and non-living things. A natural environment can include interactions among all living species, climate, weather, and natural resources that affect survival (for example, human, animal, and plant survival) and economic activity. Large-scale alterations to the climate of the natural environment affecting survival and economic activity on a large or small scale can be referred to as climate change. For example, large-scale alterations to the climate can affect survival of humans, animals, plants, and microbes differently depending on their surroundings (or environment), including a physical environment, such as a cellular environment or the plant rhizosphere, endosphere, phyllosphere, endophytic microbiome, or exophytic microbiome.

Glycoside hydrolase: Enzymes that catalyze hydrolysis of glycosidic bonds in sugars (such as complex sugars; e.g., van den Brink and de Vries, Appl Microbiol Biotechnol, 91(6):1477-92, 2011, incorporated herein by reference in its entirety). In some examples, glycoside hydrolase includes endoglucanases, exoglucanases, β-glucosidases, xylanases and xylosidases, glucuronidases, mannanases, or arabinosidases.

Halogen: An atom selected from fluoro, chloro, bromo, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group. Exemplary heteroaliphatic groups include, but are not limited to, aliphatic groups comprising an ether, a thioether, an ester, an amine, a carboxy, a carbonyl, or an amide.

Heteroaliphatic-aromatic: An aromatic group that is or can be coupled to a probe disclosed herein, wherein the aromatic group is or becomes coupled through a heteroaliphatic group.

Heteroaliphatic-aryl: An aryl group that is or can be coupled to a probe disclosed herein, wherein the aryl group is or becomes coupled through a heteroaliphatic group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaromatic: An aromatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or two or more fused rings, which fused rings may or may not be aromatic and/or contain a heteroatom, provided that the point of attachment is through an atom of the aromatic heteroaryl group. In some embodiments, the heteroaryl ring is selected from, but not limited to, pyridinyl, quinolinyl, quinazolinyl, quinoxalinyl, benzoquinolinyl, benzoquinoxalinyl, benzoquinazolinyl, indolyl, indolinyl, benzofuranyl, benzothiophenyl, benzimidizolyl, purinyl, carbazolyl, acridinyl, phenazinyl, and the like.

Heteroaliphatic-heteroaromatic: A heteroaromatic group that is or can be coupled to a probe disclosed herein, wherein the heteroaromatic group is or becomes coupled through a heteroaliphatic group.

Ketone: —C(O)$R^b$, wherein $R^b$ is selected from aliphatic, aryl, heteroaliphatic, aliphatic-aryl, heteroaryl, aliphatic-heteroaryl, heteroaliphatic-aryl, heteroaliphatic-heteroaryl and any combination thereof.

Lignin: A cross-linked phenolic polymer typically found in plant cell walls. Although lignin is a recalcitrant polymer and resistant to acid/base hydrolysis, it can be degraded enzymatically (for example, by ligninolytic enzymes, including heme peroxidases, such as lignin peroxidases, manganese peroxidases, versatile peroxidases, and dye-decolorizing peroxidases, as well as copper-based laccases; for example, Janusz et al., FEMS Microbiology Reviews, 41(6): 941-962, 2017; Cragg et al., Current Opinion in Chemical Biology, 29:108-119, 2015, both of which are incorporated herein by reference in their entireties). In some examples, lignins include p-hydroxyphenyl, guaiacyl, or syringyl monomers.

Microbe: Microorganism or microscopic organism, including all unicellular organisms and microbes that live as a single cell or in a colony of cells. Examples of microbes include bacteria, archaea, algae, fungi, protozoa, yeast, and viruses. In some examples, microbes are present in an environment (for example, the surroundings of plants) or are present in, on, or around another organism, such as a plant (for example, as part of a microbiome of a plant, such as an internal or external plant microbiome).

Nutrient cycling: The process by which nutrients, such as carbon, nitrogen, phosphorus, and sulfur, are exchanged among different environments and ecosystems, such as biosphere, pedosphere, geosphere, hydrosphere, atmosphere, lithosphere, and terrestrial and marine ecosystems. In some examples, proteins and enzymes (for example, microbial enzymes) are used for nutrient cycling. In some examples, nutrient cycling includes nitrogen or carbon cycling, such as using proteins or enzymes that directly or indirectly interact with vitamin b (for example, for transport or metabolism of vitamin b1, b2, b3, b5, b7, b9, and b12; Bertrand and Allen, Front Microbiol, 3:375, 2012, incorporated herein by reference in its entirety); amino acids (for example, for transport, assimilation, or metabolism of amino acids, such as by glutamine synthetase, glutamate synthase, or glutamate dehydrogenase; Moe, Am J Bot, 100(9):1692-705, 2013; van Heeswijk et al., Microbiol Mol Biol Rev, 77(4):628-95, 2013; Mora, Microbiol Rev, 54(3):293-304, 1990, all of which are incorporated herein by reference in their entireties), including alanine (ala or A), arginine (arg or R), asparagine (asn or N), aspartic acid (asp or D), cysteine (cys or C), glutamine (gin or Q), glutamic acid (glu or E), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V); sugars or starches (for example, metabolism of sugars and starches, such as xylanose, glucose, or cellbiose); or lignins (for example, metabolism or transport of p-hydroxyphenyl, guaiacyl, and syringyl monomers). In some examples, nutrient cycling includes sulfur or phosphorus cycling (for example, Kertesz et al., FEMS Microbiol Rev, 24(2):135-75, 2000; Korstee et al., Biochemistry (Mosc), 65(3):332-40, 2000, both of which are incorporated herein by reference in their entireties).

Plant stress: Plants experience plant stress when they are not growing under ideal conditions, including access to ideal nutrient levels, water levels, temperature, microbes, or light levels or upon exposure to pests (for example, a living organism that occurs where it is not wanted or that causes damage to plants, animals, or ecosystems), pathogens (for example, any organism that can produce disease), or pollutants (for example, contaminants, such as a substance or energy, including light or radiation, that causes adverse, undesired, harmful, or poisonous effects). Microbes associated with plants can affect plant stress, such as increase or decrease plant stress, for example, depending on the stress (for example, change in $CO_2$ level, temperature, or water level) or microbe (for example, bacteria, fungi, or algae, such as microbes that interact with plants and inhabit the plant or surrounding soil).

Phosphate: A functional group having a structure —P(O)(O$^-$)$_2$ or —P(O)(OH)$_2$ when attached to a probe embodiment described herein and having a structure P(O)(O$^-$)$_3$ or P(O)(OH)$_3$ when not attached to a probe embodiment. Such groups that are in ionized form can further be associated with a suitable counterion.

Proteomics: A study of proteins, for example, a large- or small-scale study, such as using techniques for separating, identifying, and analyzing proteins (for example, analyzing intermolecular or intramolecular interactions, such as protein structure, protein-protein interactions, or protein-ligand interactions; Lee, *Trends Biotechnol.*, 19(6):217-22, 2001, incorporated herein by reference in its entirety). Many tools are available for proteomic analysis, for example, mass spectrometry (for example, using hard or soft ionization techniques, including matrix-assisted laser desorption/ionization or electrospray ionization, for example, with mass analyzers, such as time of flight, quadrupole filter, or ion trapping, as well as other techniques, such as liquid chromatography, capillary electrophoresis, tandem mass spectrometry, or fragmentation techniques, for example, collision-induced dissociation); electrophoresis (for example, 1D- or 2D-gel electrophoresis or western blotting), immunological assays (for example, immunological microarray assays or enzyme-linked immunosorbent assays, ELISAs), protein microarray assays (for example, functional protein or target protein array assays), chromatography (for example, affinity, size-exclusion, ion-exchange, or reverse-phase), tools for analyzing protein structure or electrochemistry (for example, x-ray crystallography or nuclear magnetic resonance), computational or bioinformatics tools (for example, protein identification, structure, or interaction modeling tools), or any combination thereof. In some embodiments, mass spectrometry (MS), such as liquid chromatography MS (LC-MS), is used.

Tag Moiety: A functional group or a molecule that is capable of producing a signal that can be visually and/or instrumentally detected. In particular disclosed embodiments, the Tag moiety provides the ability to visualize or detect, using an appropriate detection method, an enzyme because the reporting moiety becomes covalently attached to the enzyme.

pTag Moiety: A functional group that is capable of being converted to a Tag moiety by coupling with a functional group or molecule capable of producing a signal that can be visually and/or instrumentally detected.

Sulfate: A functional group having a structure —OSO$_2$O$^-$ or —OSO$_2$OH when attached to a probe embodiment described herein and having a structure SO$_2$(O$^-$)$_2$ or SO$_2$(OH)$_2$ when not attached to a probe embodiment. Such groups that are in ionized form can further be associated with a suitable counterion.

The descriptions provided above are not intended to include impermissible substitution patterns (for example, methyl substituted with 5 different groups, and the like). Such impermissible substitution patterns are recognized by a person of ordinary skill in the art. In formulas and specific compounds disclosed herein, a hydrogen atom is present and completes any formal valency requirements (but may not necessarily be illustrated) wherever a functional group or other atom is not illustrated. For example, a phenyl ring that is drawn as

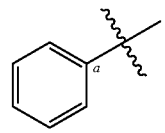 [SMILES: *c1ccccc1]

comprises a hydrogen atom attached to each carbon atom of the phenyl ring other than the "a" carbon, even though such hydrogen atoms are not illustrated.

Any functional group disclosed herein and/or defined above can be substituted or unsubstituted, unless otherwise indicated herein.

II. INTRODUCTION

New approaches capable of coupling the measurement of biochemical activity with identification of the species involved (for example, microbes and enzymes) are needed to better understand how to improve a variety of processes associated with plants and environmental microbiomes (for example, cellular, soil, and/or aquatic environments). Such processes can include, but are not limited to, energy production from biomass degradation (for example, (bio)processing of lignocellulosic and/or chitin-based feedstocks, sugar transportation, etc.), plant nutrition, and bioremediation. In particular, a process for separating microbes and other analytes based upon their actual function is needed and is accomplished and described herein. In particular, a function-based probe technology for function-dependent separation of analyte species, such as uncultivated microbes, from their native habitat is disclosed. This technology further provides the ability to perform enrichment of particular analytes and also to perform single cell genome sequencing. This function-based probe approach addresses a challenge to discover and study new branches of life and new metabolic activities through massive-scale isolation and sequencing of unexplored microbial "dark matter" by analyzing cellular samples, soil samples, and/or aquatic samples with the probes.

Disclosed herein are embodiments of function-based probes, devices, kits, and methods for selectively labeling analytes (for example, proteins and enzymes in microbial cells) within samples (for example, soil, cellular, and/or aquatic samples) based upon specific functional activities of interest (for example, bioprocessing for development of alternative energy sources, carbon and nitrogen cycling in soil relevant to climate change and plant/crop performance, soil toxin analysis, soil and plant nutrient acquisition, and the like).

The function-based probes disclosed herein can be deployed directly in living microbial populations within their native habitat. The probes are capable of binding to analytes of interest and even can be taken up by cells. The probes are designed with specific structural motifs that facilitate interactions with a particular analyte such that the particular analyte will bind the probe while other analytes will not. The probes further comprise structural components that facilitate binding to the analyte and detecting the probe-analyte conjugate. The probes thus can be used to detect the presence of particular analytes and further can be used to enrich these analytes for downstream analysis (for example, flow cytometry or other detection methods, sequencing, proteomics, and combinations thereof). A schematic illustration of methods that use certain probe embodiments described herein is provided in FIG. 1. In particular embodiments, the probes are used to functionally annotate and isolate uncultivated microbes present, for example, in cellular environments, soil environments, aquatic environments, and combinations thereof.

Probe embodiments disclosed herein comprise a reactive group that is configured to form an irreversible bond with a target analyte and a tag precursor moiety that can be converted to a tag moiety that can be detected using various analytical techniques. In some embodiments, the tag moiety can be attached to the probe before its use. In some embodiments, the probes can further comprise a binding group that directs a probe toward a particular analyte capable of interacting with and/or detecting the binding group. The binding group also may facilitate cell permeability. In yet additional embodiments, the probe can comprise an anchor group that includes a functional group that is suitable for covalently anchoring the probe to a substrate, such as substrate components of device embodiments disclosed herein. In some embodiments, the anchor group can be attached to the probe embodiment by way of a bi-functional linker as described herein. The probe embodiments disclosed herein form stable covalent bonds with active analytes in complex proteomes by direct reaction with reactive analyte functional groups (for example, protein residues) and/or via photoreactive crosslinking.

In some embodiments, cell populations identified by probe embodiments described herein can be classified based on function (for example, enzyme activity, metabolite uptake, or protein-metabolite sensing) and subsequently sequenced to determine phylogeny. The function-based probes and methods described herein can be used to analyze myriad microbial functions of interest by using different chemical probes specific for defined functions. The disclosed technology is not limited to targeted cell sorting for sequencing, however, and also can be used in parallel with proteome analyses that reveal the identity of the proteins responsible for function-based labeling of cells. This technology provides a generalizable strategy to isolate microbes with desired functions from communities from all types of environments, and to sequence proteins and genomes associated with that activity. It also permits the manipulation of communities for improved metabolic output. For instance, soil and aquatic biomes can be evaluated to determine whether there are any deficiencies and/or improvements needed to promote plant/soil nutrition, particularly in response to environmental changes. Additionally, entities involved in the degradation and transport of components within plants and/or soil can be evaluated, particularly lignolytic, cellulolytic, and intracellular metabolic and transport pathways. Additionally, negative health effects may be attributed to off-target activity from organophosphate compounds present in soil and aquatic environments and thus certain probe embodiments can be used to mimic such compounds and identify the pathways in which these types of compounds participate.

III. PROBES AND METHODS OF MAKING

Probe embodiments described herein comprise moieties that facilitate their use in function-based sorting and identification of analytes present in environmental microbiomes. In particular embodiments, the probes comprise a reactive group capable of forming an irreversible chemical bond with a target analyte. The reactive group forms a stable covalent bond with analyte species in complex proteomes upon exposure to a reactive region of the analyte (for example, protein residues) and/or by activation of the reactive group to form a reactive intermediate that binds to the analyte (for example, photoreactive crosslinking with a protein). In some embodiments, the probes further comprise a precursor moiety ("pTag") that can be converted to a tag moiety. In other embodiments, the probes can comprise a pre-installed tag moiety. The tag moiety (whether pre-installed or added subsequent to exposing the probe to an analyte) provides the ability to rapidly and sensitively detect and measure labeled analytes. In some embodiments, the probe can further comprise a binding group, which can be a functional group or a molecule that is attached, either directly or indirectly, to the reactive group of the probe. The binding group is used to draw the analyte to the probe. In some embodiments, the binding group can be cleaved or displaced from the probe by the analyte. Thus, the binding group can facilitate binding the probe and the analyte together via the reactive group of the probe. In yet additional embodiments, the probe can comprise an anchor group that facilitates immobilization of the probe on a substrate for analysis.

Methods of using the probe embodiments described herein also are disclosed. In particular disclosed method embodiments, the probe can be adhered to a support or simply combined with a sample. The probe is allowed to interact with any suitable enzymes present in the sample and/or can be affirmatively activated to facilitate binding the probe to the species of interest. The species that becomes labeled with the probe can be enriched and measured by proteomics, and/or can undergo further analysis (for example, imaging, SDS-PAGE, or fluorescence-activated cell sorting (or "FACS"), mass spectrometric analysis, proteomics, or combinations thereof). Methods of use are described in more detail herein. Classes of probe embodiments of the present disclosure are discussed below.

A. Glycoside Hydrolase Probes, Lignin Degradation Probes, and Sugar Transfer Probes Efficient lignin removal from lignocellulosic plant biomass allows access the energy-rich and more easily metabolized cellulose and hemicellulose for the production of biofuels and other cellulose-based chemicals. Lignin accounts for 15-30% of lignocellulosic plant biomass, but its structural complexity and degradation resistance makes it a roadblock to biofuels production.

Several microorganisms effectively degrade the carbohydrate components of lignocellulose. However, very few are known to be capable of complete biomass degradation; that is, lignin depolymerization and metabolism coordinated with cellulose and hemicellulose degradation and metabolism. Fungi have been studied since the mid-1980s, but there is still no commercial biocatalytic process for fungal lignocellulose deconstruction, primarily because of fungi's poor stability in industrial processes and difficulties in developing efficient heterologous systems for enzyme expression and purification. Therefore, potential new and emerging microbes need to be characterized at the systems level to advance research toward efficient and economically feasible next-generation biofuel production.

Soil microbes, including bacteria and fungi—particularly from heavily forested or vegetated regions—deconstruct lignocellulose. The actinomycetes have potential for biofuels production, particularly *Streptomyces* species, because of their efficiency in lignin degradation, established genetic and molecular engineering tools, and availability of a small number of genomes. Despite the relatively new attraction toward these microbes, little is known about the involvement or functional activities of analytes involved in lignocellulose degradation, or the transport and intracellular utilization of lignocellulosic catabolites. Currently, elucidation of these activities is heavily reliant on poorly annotated genomes, with as much as 25-50% of gene products annotated as "hypothetical." A challenge in transforming these microbes from research organisms to industrially relevant microbes for biofuel production is a thorough understanding of the cohort of discrete proteins involved in complex lignocellulose transformation and metabolism, which is experimentally observed only as organism-level chemical phenotypes.

Unlike computational methods that depend on gene function inference from homology-based informatics, the present disclosure concerns variants of function-based probes that undergo specific interactions with analytes, including analytes involved in lignin degradation and thus can be used to define the lignocellulolytic physiology of bacterium involved in the degradation. As such, a preexisting understanding of "known" domains is not needed and instead the probes and methods rely on in vivo biochemical events for annotation, thereby facilitating discovering, for example, new enzymes and pathways that cannot be identified using conventional methods. Some probe embodiments include mechanism-based probes that report on function by reactions dependent on the catalytic mechanism of the target enzymes (for example, glycoside hydrolases and lignin peroxidases). Some additional probe embodiments include probes that mimic lignocellulosic catabolites to elucidate the extra- and intracellular protein interactions involved in the transport and metabolic fate of these small molecules (for example, cellobiose or β-aryl ether-based probes). Results from probe exposure can be coupled to global proteome, RT-PCR, and biochemical activity assays to functionally map and annotate the unique lignocellulolytic mechanism(s), functional associations, and differential functional activity responses to varying feedstock substrates employed by different enzymes.

Certain embodiments of the probes and function-based analytical methods of the present disclosure concern chemical probes that are designed for lignocellulose degrading microbes and can be used to identify, characterize, annotate, and map functional lignolytic, cellulolytic, and intracellular metabolic and transport pathways. In particular disclosed embodiments, soil actinomycetes, such as *Streptomyces viridosporus* T7A, and other microbes applicable for biofuel generation can be characterized at individual protein levels using the probe embodiments disclosed herein. The probe embodiments disclosed herein also can be used to identify and characterize novel lignocellulolytic enzymes and metabolic pathways of such enzymes. In additional embodiments, probe embodiments described herein can be used to identify and characterize carbohydrate transporters, which mediate the recovery of metabolites from the enzymatic catabolism of plant cell walls. Such probe embodiments only bind transporters that actively uptake saccharide substrates and thus can target proteins involved in sugar transport and metabolism and mimic sugars that can be transported and bind to specific proteins in lignin and/or cellulose metabolic pathways, thereby providing observation of metabolic pathways that proteins employ with sugars. Also disclosed are probe embodiments that can be used to characterize lignin degradation and aromatic monomer transport and metabolism. These probes target bacterial heme peroxidases, including heme-containing lignin depolymerizing peroxidases.

In some embodiments, the probes can be used to profile glycoside hydrolases, including endoglucanases, exoglucanases, β-glucosidases, xylanases and xylosidases, glucuronidases, mannanases, and arabinosidases. In particular embodiments, the probes are capable of reacting with cellulosic endo- and exoglucanases in *S. viridosporus*. Certain probe embodiments have a structure satisfying Formula I or Formula IA, illustrated below.

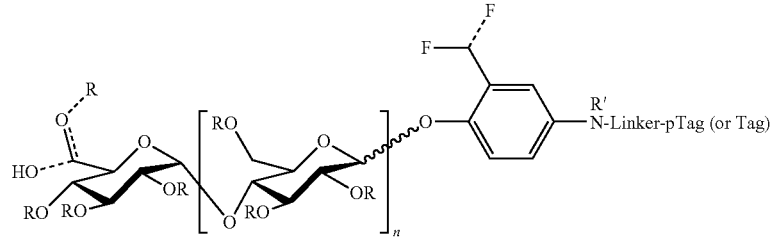

Formula I

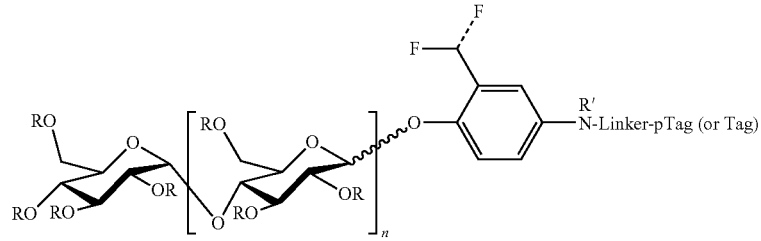

Formula IA

With reference to Formula I and Formula IA, the linker group can be an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; the pTag group comprises a clickable functional group or the Tag group (if present) is a detectable moiety; each R independently can be hydrogen, aliphatic, or a protecting group; R' can be hydrogen, aliphatic, heteroaliphatic, or aromatic; and n can be a integer selected from 0 to 10, such as 1 to 10, or 2 to 10, or 3 to 10, or 4 to 10. In particular disclosed embodiments, the linker is a heteroaliphatic linker comprising a carbonyl group and an aliphatic group, such as an alkyl, alkenyl, or alkynyl group, with particular embodiments comprising a lower alkyl group, such as —$(CH_2)_m$—, wherein m is an integer selected from 1 to 10, such as 1 to 8, or 1 to 6, or 1 to 4, or 1 to 3. In yet additional embodiments, the linker can be a heteroaliphatic linker comprising a carbonyl group and a heteroaliphatic group, such as an alkylene oxide (for example, PEG). In particular embodiments, the pTag group is an azide or an alkyne. In particular disclosed embodiments, each R independently is hydrogen or an acetyl group. In particular embodiments, n is an integer selected from 0 to 10, such as 1 to 10 or 2 to 10 and in preferred embodiments is 2, 3, 4, or 5. In embodiments where n is 0, the saccharide component comprises an acid moiety. In an independent embodiment, n is not 0 or 1. If the probe comprises a pre-installed Tag group, the Tag group can be a detectable moiety, such as a fluorophore, a chromogen, or a member of a specific binding pair (for example, biotin or streptavidin). The wavy bond ("⌇") indicates that the bond can either be in an alpha or beta configuration.

In yet additional embodiments, the linker group of these probes, and any probes disclosed herein, can be a bi-functional linker that binds the pTag (or Tag) group to the probe and further binds an anchor group to the probe. This anchor group provides a functional handle by which the probe can be attached to a substrate, which is discussed in further detail herein. Representative anchor groups can include, but are not limited to, clickable functional groups (for example, an alkyne or an azide), carboxylic acids, NHS-esters, amines, alkyl halides or any other functional group that can be coupled to a surface-modified substrate as described herein. Representative structures of bi-functional linker are illustrated below and the amine portion (labeled as "$N_p$") of the probe used to append the bi-functional group is illustrated and n can be an integer ranging from 0 to 20, such as 0 to 15, or 0 to 10, or 0 to 5, or 0 to 3; and each R independently is hydrogen, aliphatic, or aromatic.

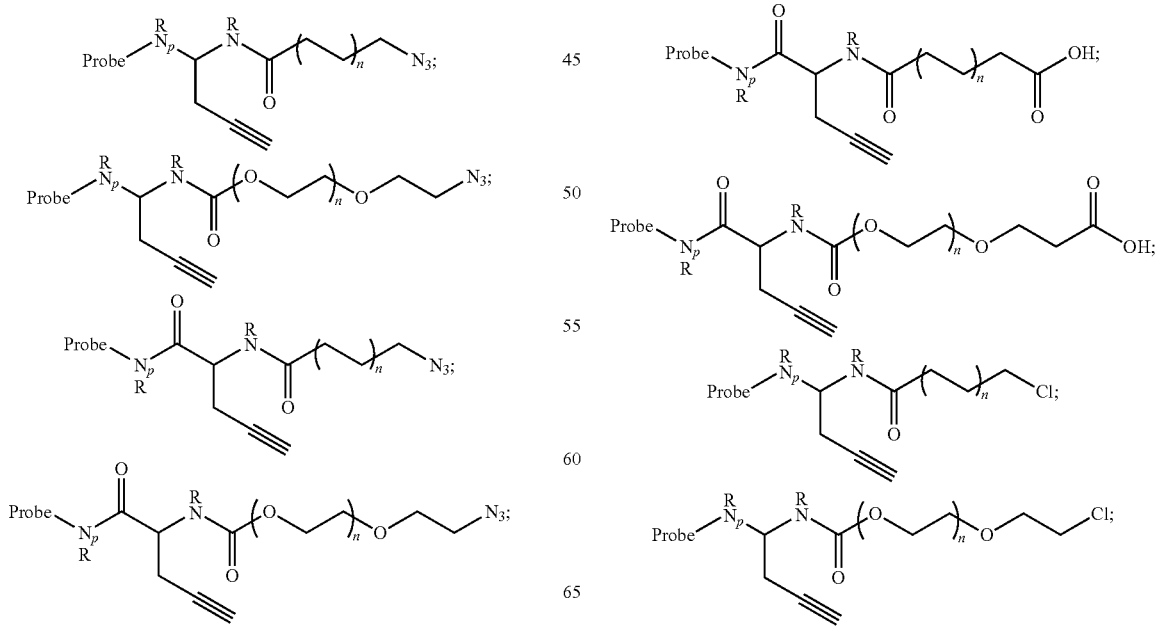

-continued
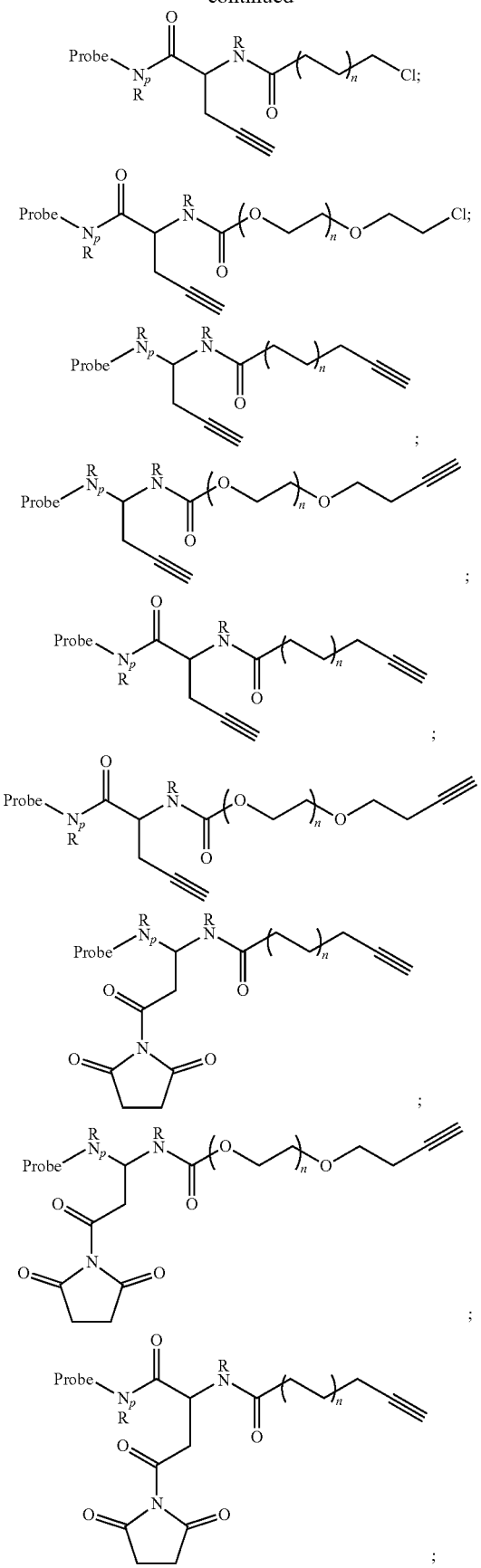
-continued
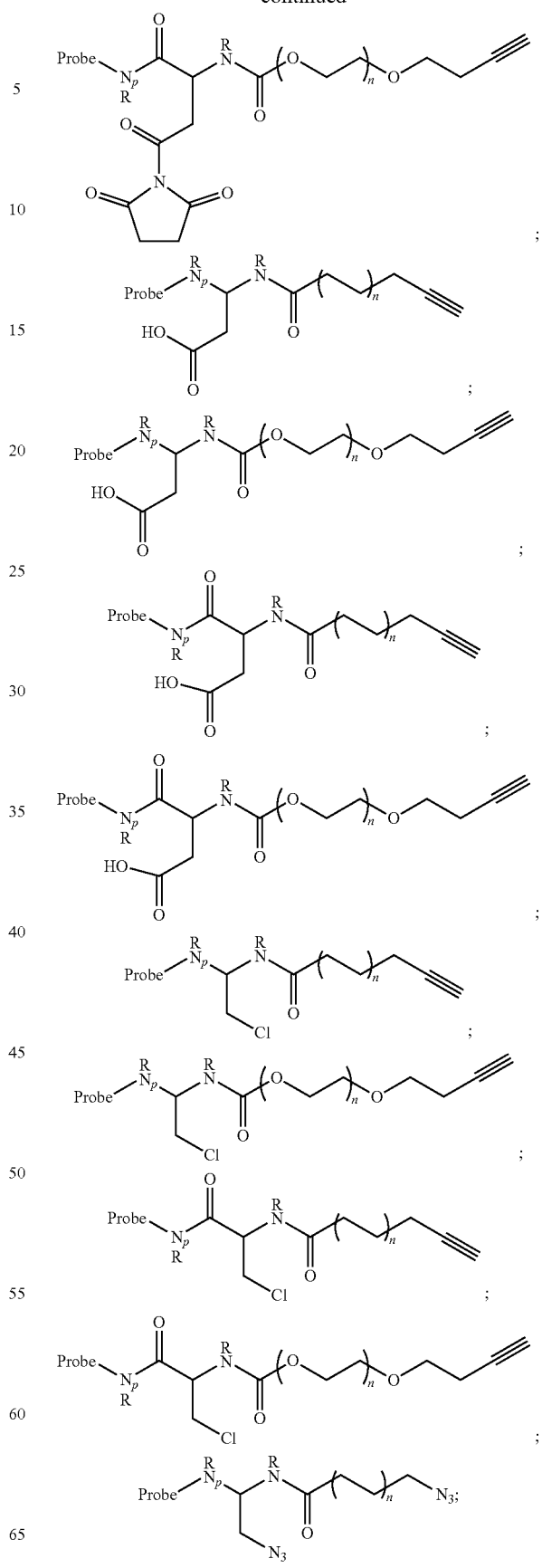

-continued
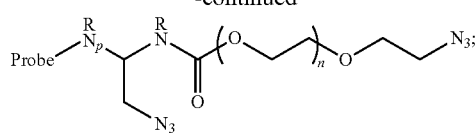
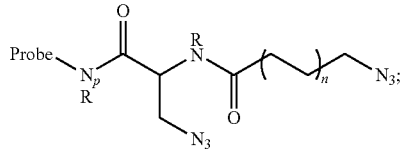
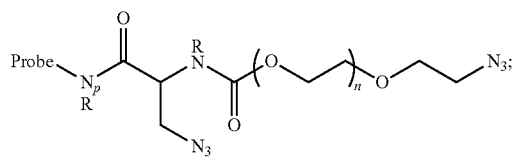
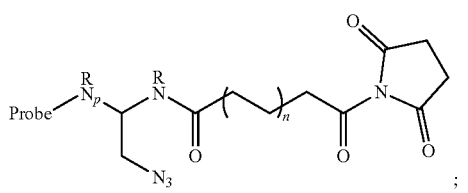
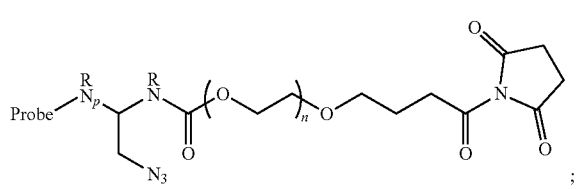
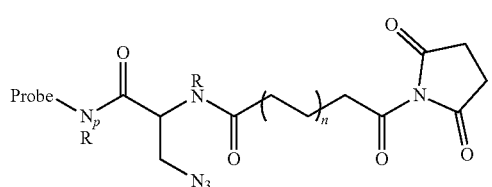
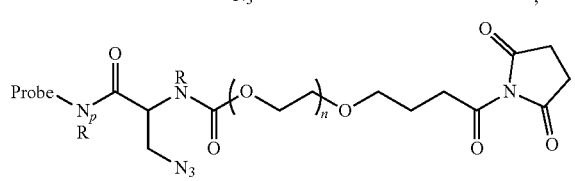
-continued
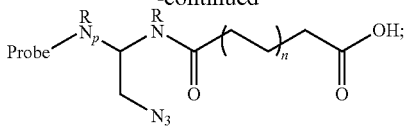
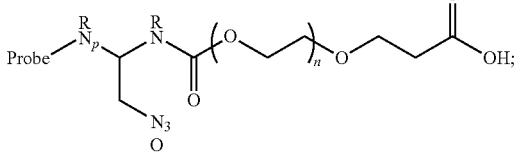
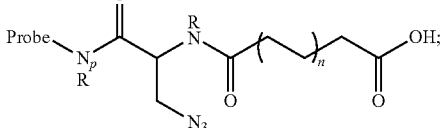
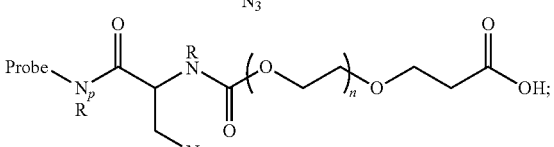
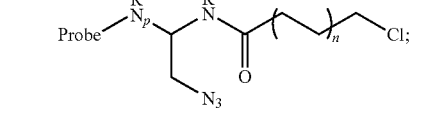
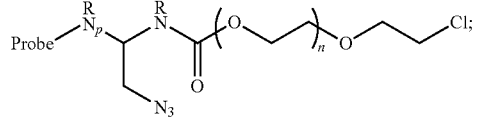
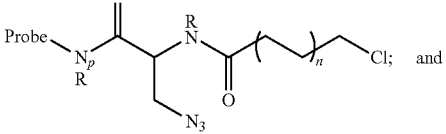
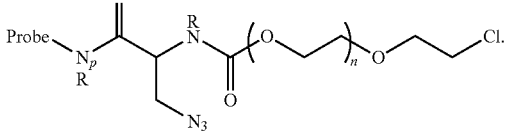
Representative species of Formula I include, but are not limited to:
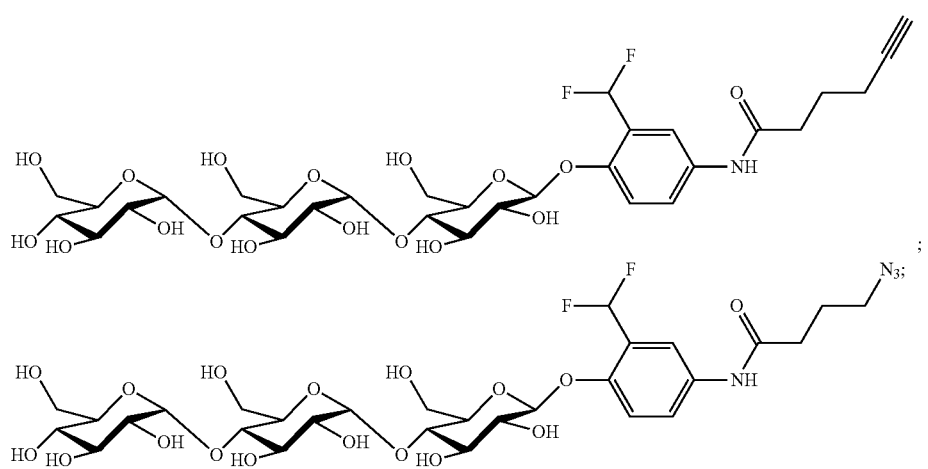

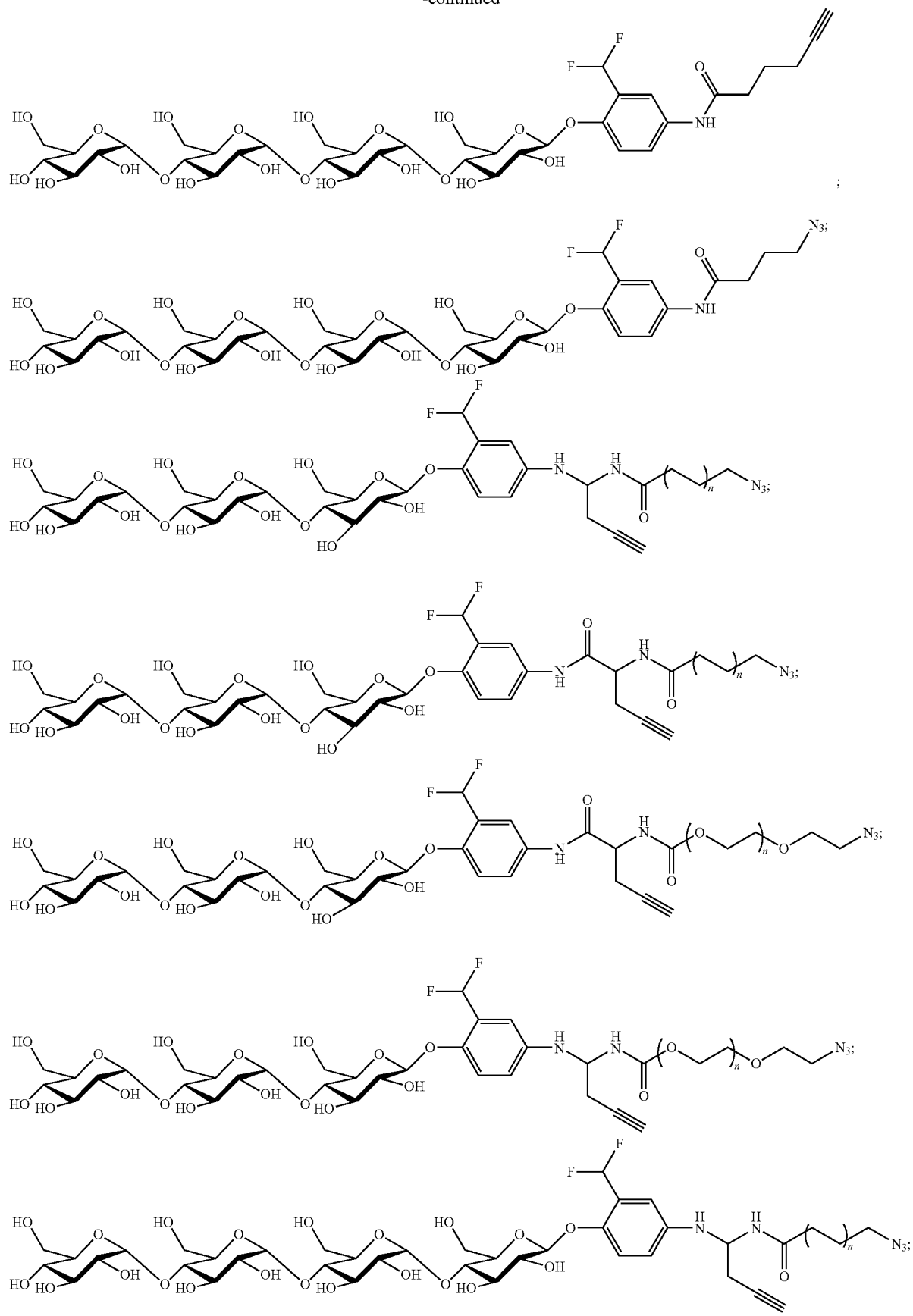

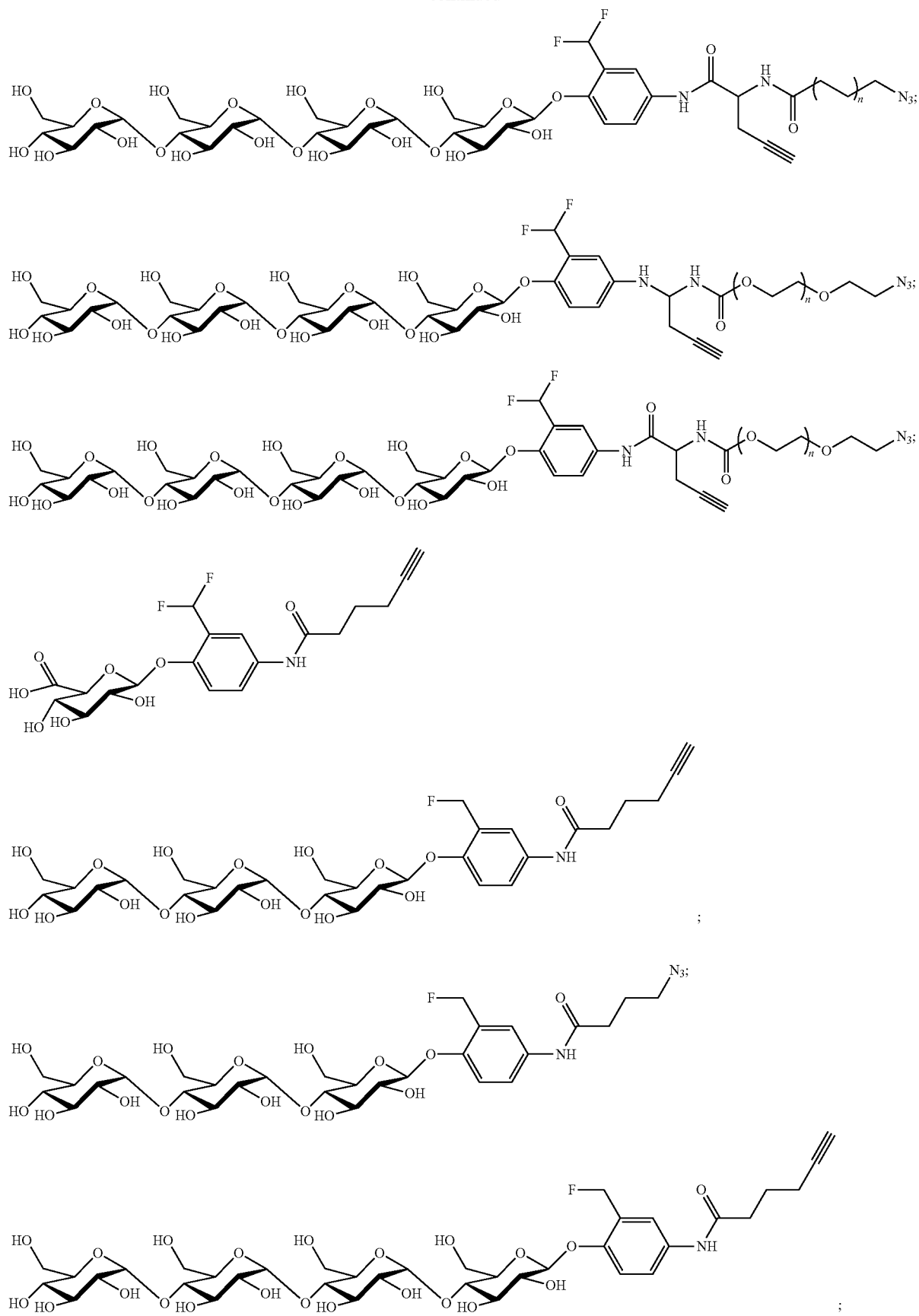

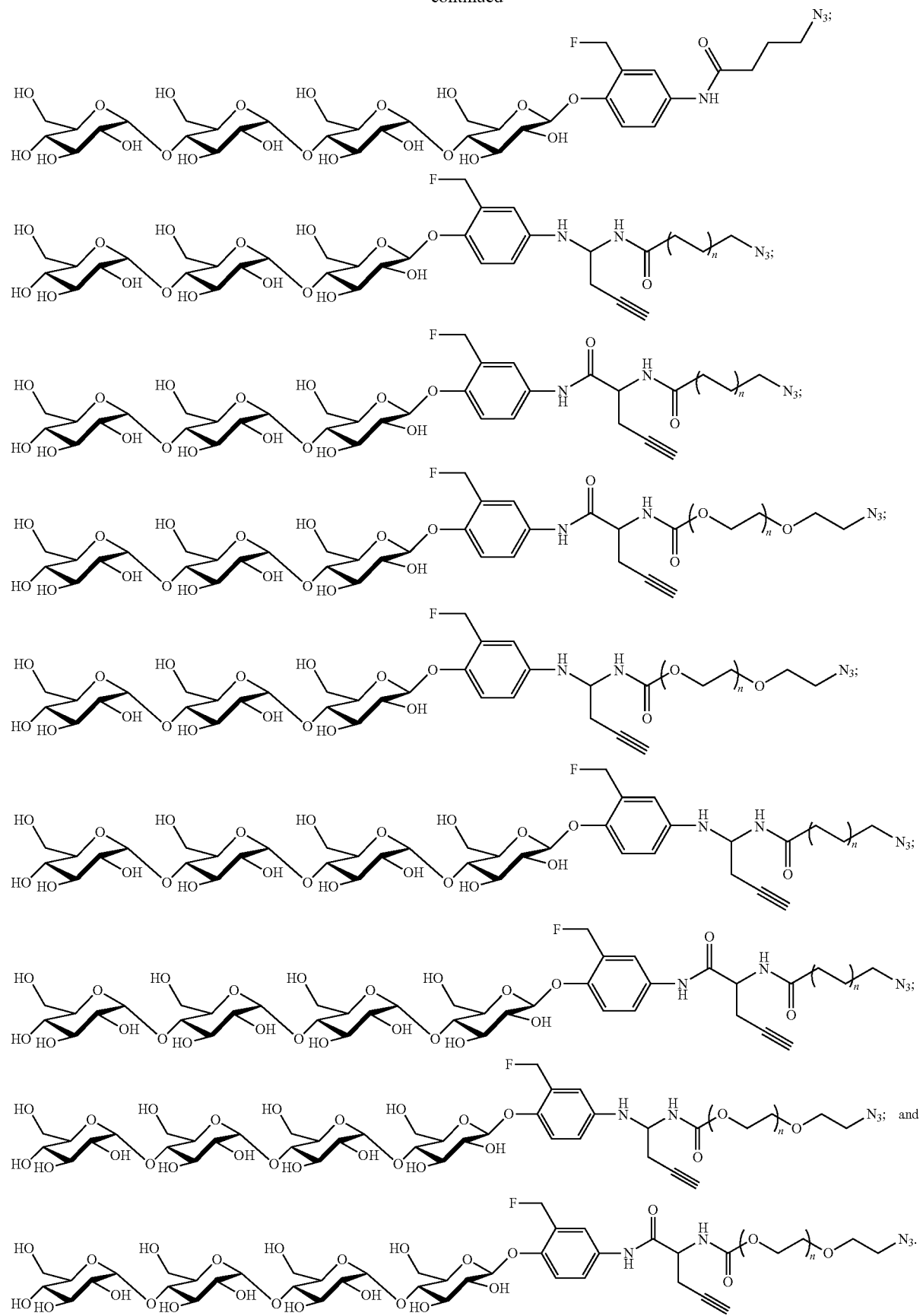

Probes used for methods involving identifying and characterizing glycoside hydrolase (that is, probes of Formula I) can be made using embodiments of the general method illustrated below in Scheme 1. With reference to Scheme 1, X can be a suitable leaving group, such as an OTf group or a halide atom (for example, Br or Cl). In some embodiments, Y can be a hydroxyl group or a halide. The method illustrated in Scheme 1 also can be modified using methods recognizable to those of ordinary skill in the art with the benefit of the present disclosure to incorporate a bi-functional linker group as described herein. One exemplary embodiment of making a bi-functional linker group having a pTag (or Tag) moiety and an anchor group is illustrated below in Scheme 1A.

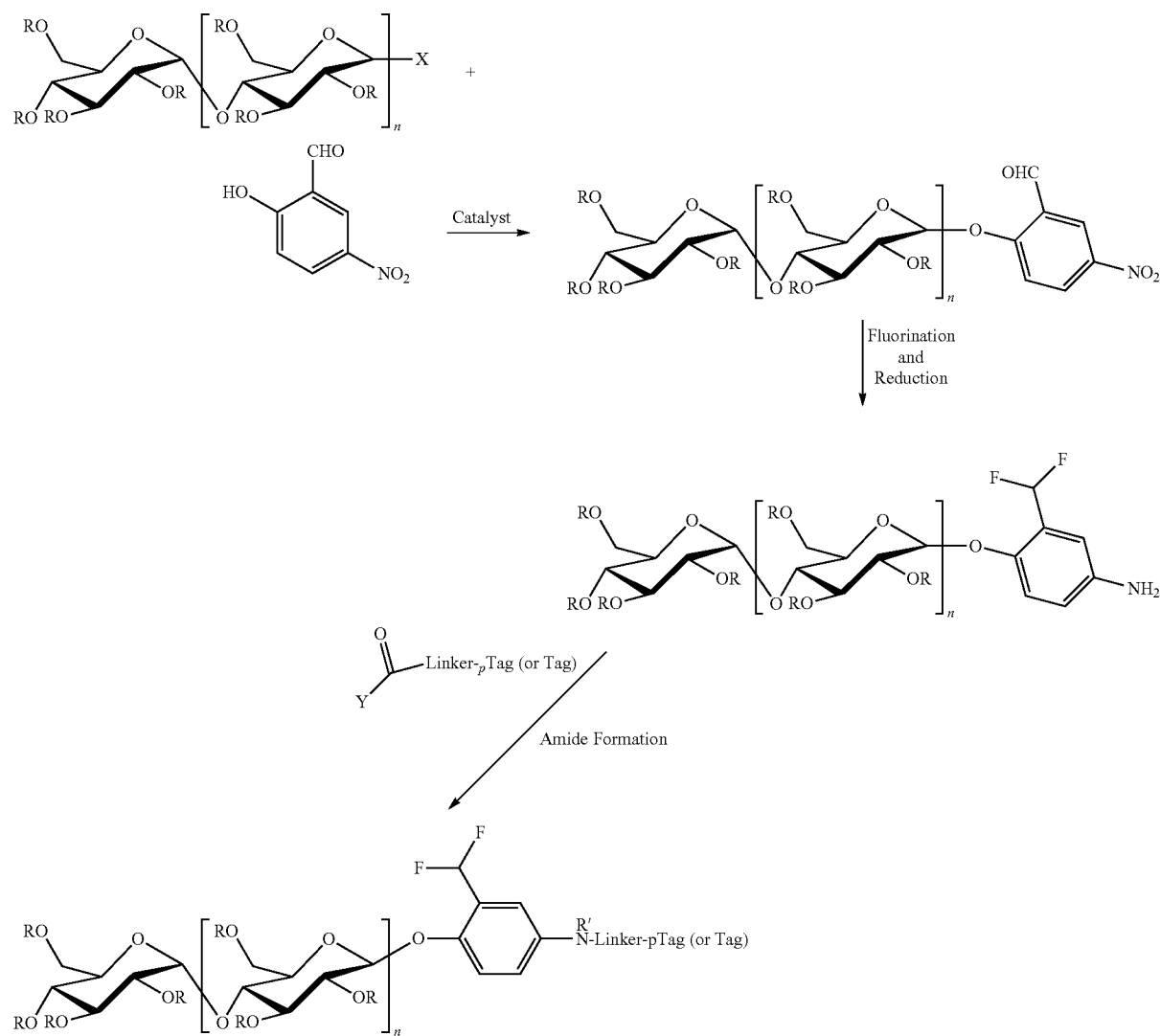

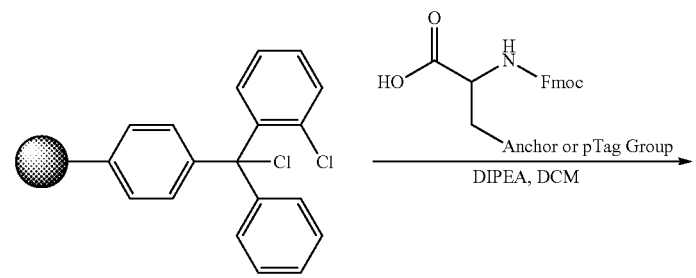

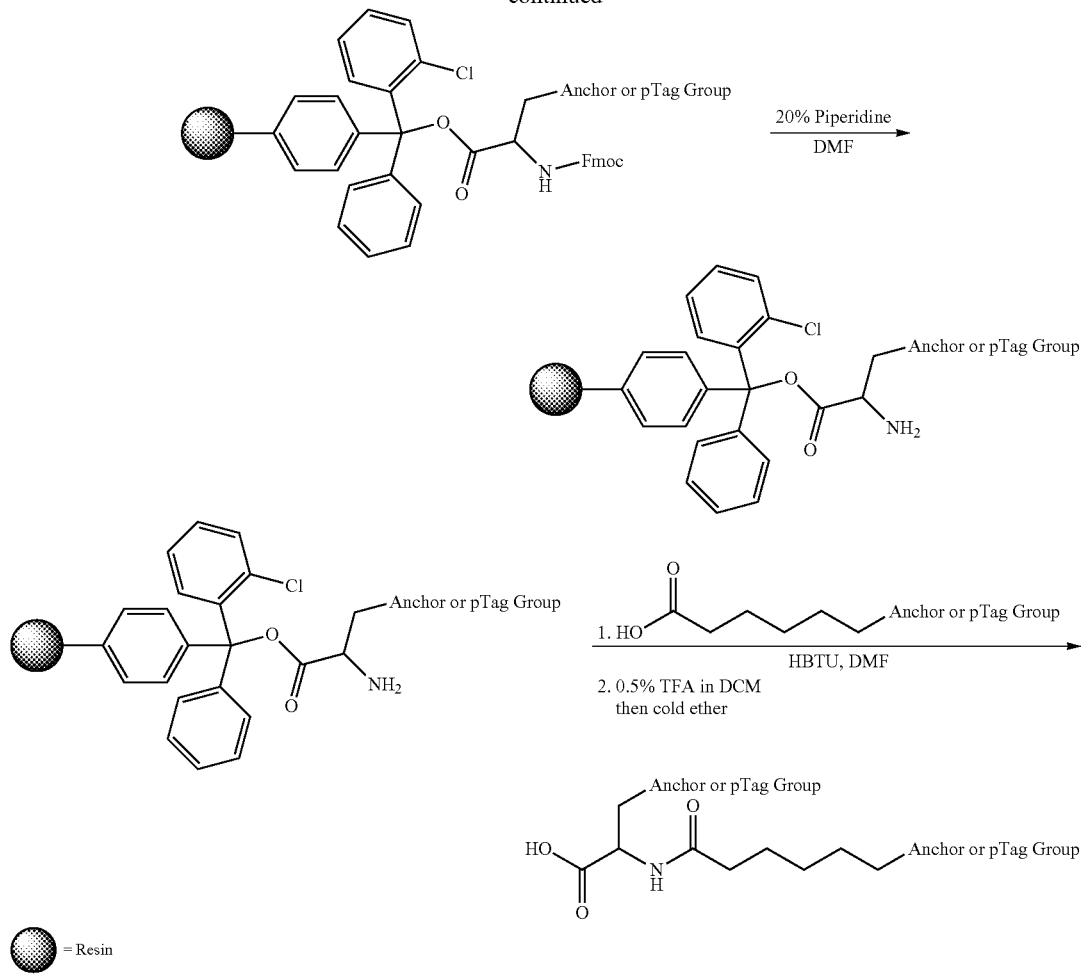

As indicated above, probe embodiments that can be used to identify and evaluate metabolic pathways that proteins employ with sugars are also disclosed. In some embodiments, these types of probes can have structures satisfying Formula II, illustrated below.

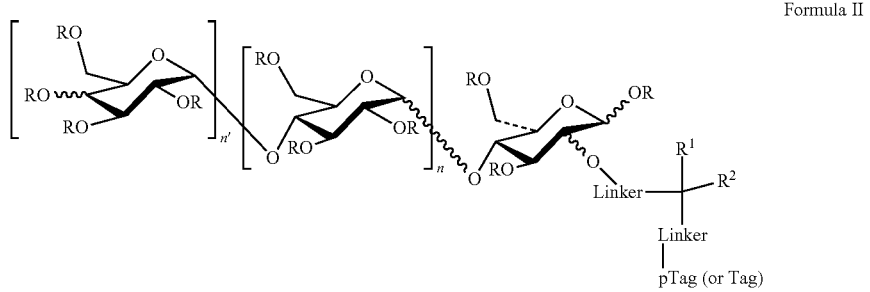

Formula II

With reference to Formula II, each linker group independently can be an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; the pTag group comprises a clickable functional group; $R^1$ is hydrogen or is a nitrogen atom that is further bound to $R^2$ by a double bond; $R^2$ is a benzophenone group or is a nitrogen atom that is further bound to $R^1$ by a double bond when $R^1$ also is a nitrogen atom. In embodiments where $R^1$ and $R^2$ are both nitrogen and thus are bound to each other, a diazirine moiety is provided. Each R group of Formula II independently can be hydrogen, aliphatic, or a protecting group (for example, acetyl); and each of n and n' independently can be an integer selected from 0 to 10, such as 1 to 10, or 2 to 10, or 3 to 10, or 4 to 10. In particular disclosed embodiments, the linker group attached to the saccharide oxygen comprises an amide group (—C(O)NR—) and an aliphatic group and the other linker comprises an aliphatic group. In such embodiments, the aliphatic group can be an alkyl, alkenyl, or alkynyl group, with particular embodiments comprising a lower alkyl group, such as —$(CH_2)_m$, wherein m is an integer selected from 1 to 10, such as 1 to 8, or 1 to 6, or 1 to 4, or 1 to 3. In yet additional embodiments, the linker group can be a bi-functional linker as described above. Any such bi-functional linkers can be used with these probe embodiments. In particular embodiments, the pTag group is an azide or an alkyne. In particular disclosed embodiments, each R independently is hydrogen or an acetyl group. In particular embodiments, n is an integer selected from 0, 1, 2, or 3 and n' is an integer selected from 0 or 1. If the probe comprises a pre-installed Tag group, the Tag group can be a detectable moiety, such as a fluorophore, a chromogen, or a member of a specific binding pair (for example, biotin or streptavidin).

In some embodiments, the probe can have a structure satisfying Formulas IIA or IIB, illustrated below, wherein each wavy bond ("⌇") indicates that the bond can either be in an alpha or beta configuration.

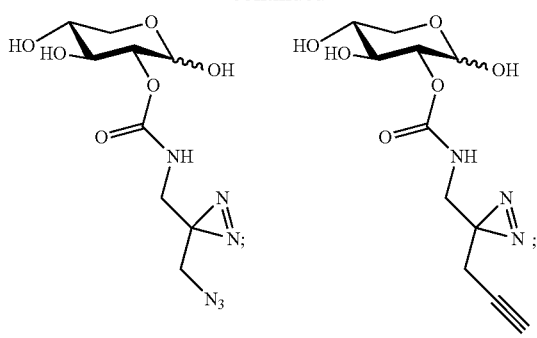

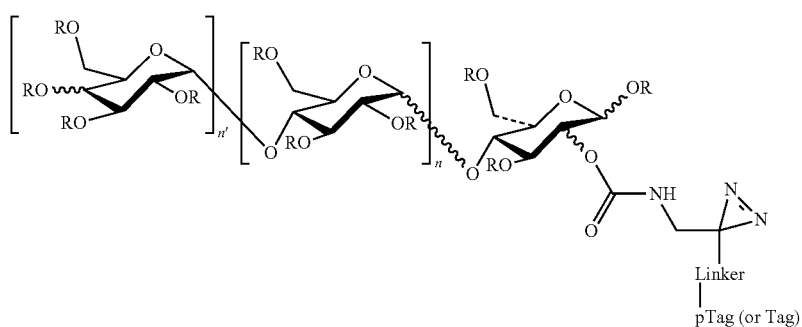

Formula IIA

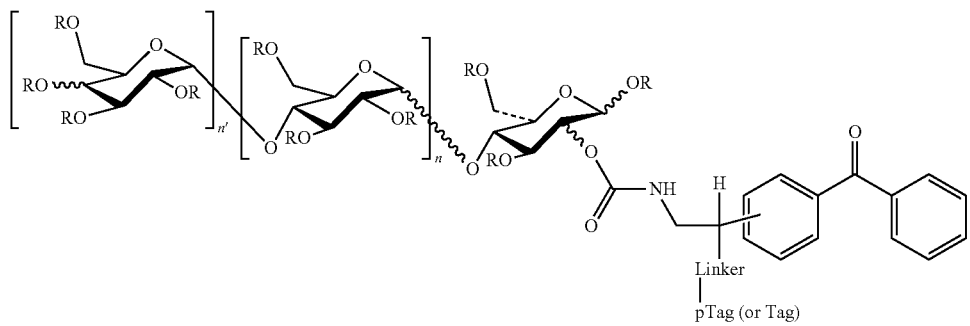

Formula IIB

Exemplary probe species meeting any one or more of Formulas II, IIA, and IIB are illustrated below:

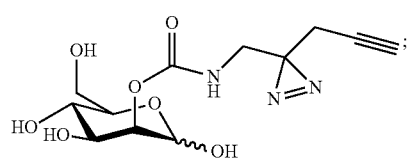

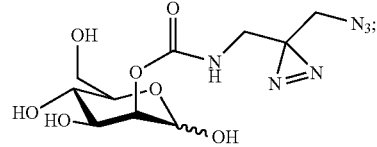

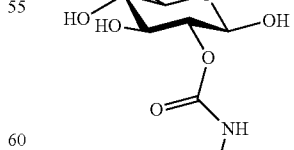

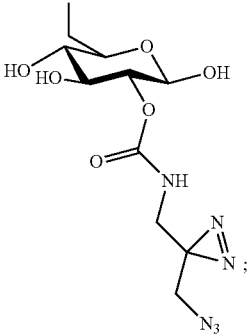

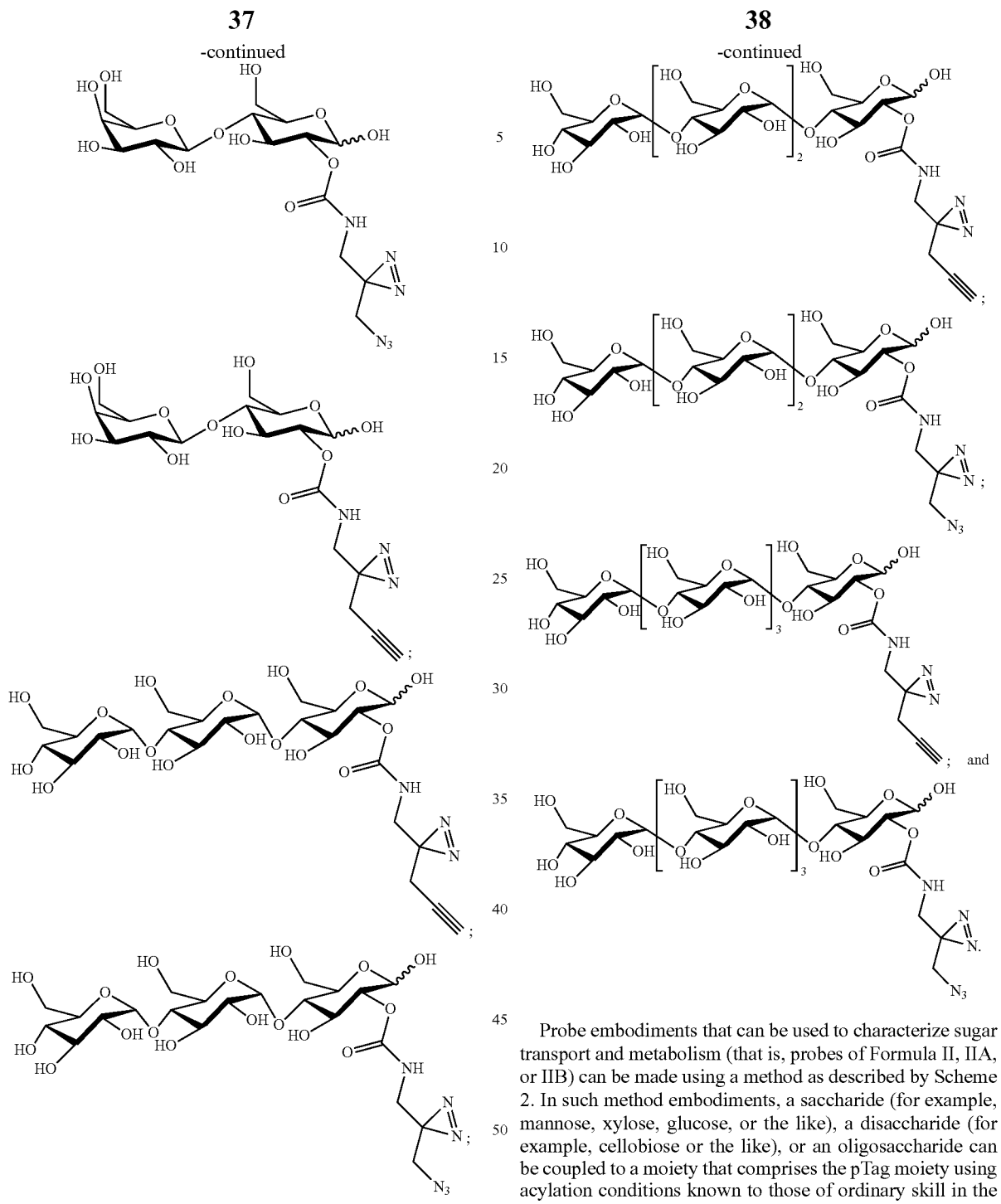

Probe embodiments that can be used to characterize sugar transport and metabolism (that is, probes of Formula II, IIA, or IIB) can be made using a method as described by Scheme 2. In such method embodiments, a saccharide (for example, mannose, xylose, glucose, or the like), a disaccharide (for example, cellobiose or the like), or an oligosaccharide can be coupled to a moiety that comprises the pTag moiety using acylation conditions known to those of ordinary skill in the art with the benefit of the present disclosure.

Scheme 2

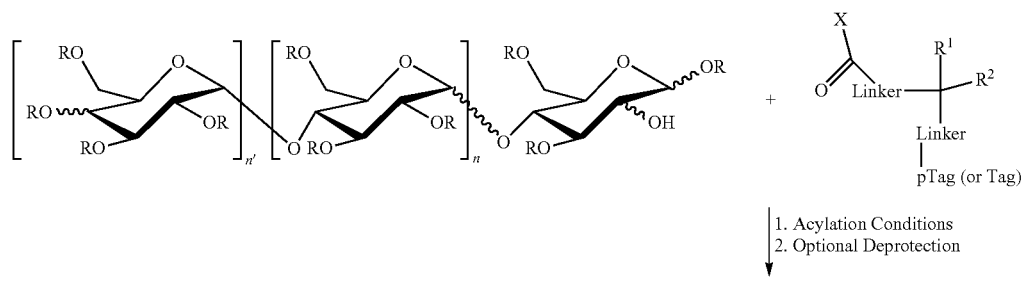

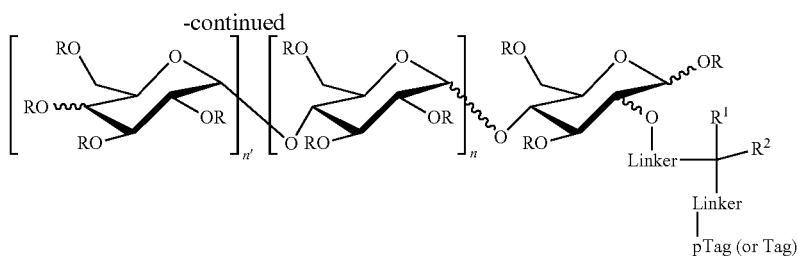

Figure 2:
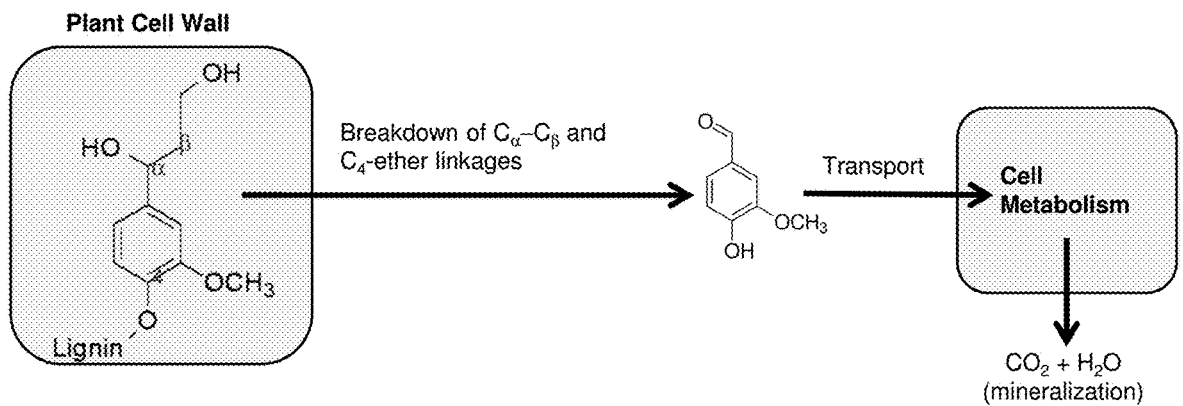
FIG. 2 shows a scheme of the enzymatic degradation of plant cell wall lignin, wherein breakdown of a lignin unit results in smaller aromatic monomers that are transported into the cell and further metabolized and potentially fully mineralized to $CO_2 + H_2O$.

In yet additional embodiments, probes that can be used to characterize lignin degradation and aromatic monomer transport and metabolism are disclosed. A schematic showing lignin degradation and aromatic monomer transport/metabolism is provided by FIG. 2. Probe embodiments that can target extracellular peroxidase enzymes, such as heme peroxidases and non-heme peroxidases (for example, Cu-containing laccases), which are involved in such processes, can have structures satisfying Formulas III, IV, or V illustrated below.

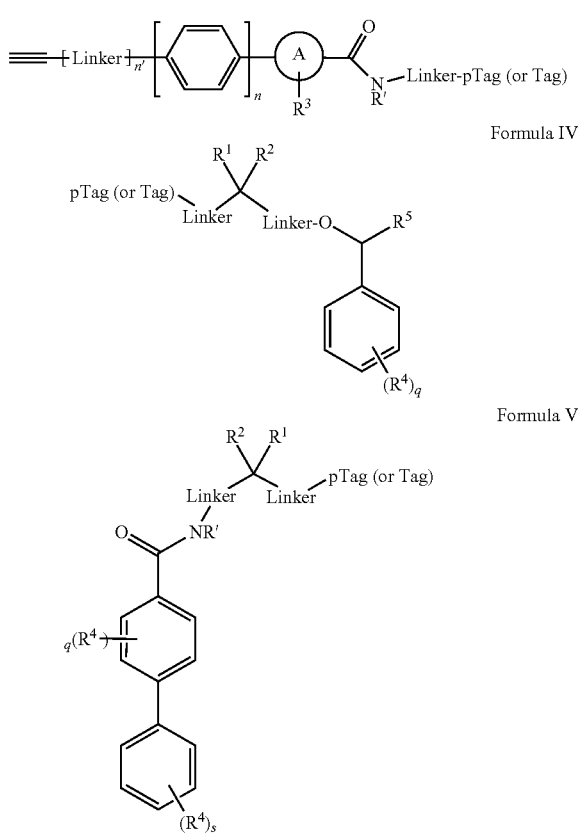

Formula III

Formula IV

Formula V

With reference to Formulas III, IV, and V, each linker independently can be an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; and the pTag group comprises a clickable functional group. In particular disclosed embodiments, each linker group independently is an aliphatic linker group, such as an alkyl, alkenyl, or alkynyl group, with particular embodiments comprising a lower alkyl group, such as —$(CH_2)_m$, wherein m is an integer selected from 1 to 10, such as 1 to 8, or 1 to 6, or 1 to 4, or 1 to 3; or an heteroaliphatic linker, such as an alkylene oxide (for example, PEG). In yet additional embodiments, the linker group can be a bi-functional linker as described above. Any such bi-functional linkers can be used with these probe embodiments. In particular embodiments, the pTag group is an azide or an alkyne. If the probe comprises a pre-installed Tag group, the Tag group can be a detectable moiety, such as a fluorophore, a chromogen, or a member of a specific binding pair (for example, biotin or streptavidin). Further variables of each formula are described below.

With reference to Formula III, ring A can be an aromatic ring system; R' can be hydrogen, aliphatic, heteroaliphatic, or aromatic; $R^3$ can be —$(CH_2)_p$—OPh or —$(CH_2)_p$-Ph wherein p is an integer ranging from 1 to 10, such as 1 to 5, or 1 to 3; and n can be an integer selected from 0, 1, and 2; and n' can be 0 or 1. In particular disclosed embodiments, ring A is an aryl or heteroaryl group, such as phenyl, naphthyl, or pyridinyl. In particular disclosed embodiments, $R^3$ can be —$(CH_2)_p$—OPh or —$(CH_2)_p$-Ph wherein p is 2. In particular disclosed embodiments, n is 0 or 1 and n' is 0.

With reference to Formulas IV and V, $R^1$ is hydrogen or is a nitrogen atom that is further bound to $R^2$ by a double bond; $R^2$ is a benzophenone group or is a nitrogen atom that is further bound to $R^1$ by a double bond when $R^1$ also is a nitrogen atom. In embodiments where $R^1$ and $R^2$ are both nitrogen and thus are bound to each other, a diazirine moiety is provided. In Formulas IV and V, each $R^4$ independently can be selected from hydroxyl or alkoxy (for example, methoxy, ethoxy, propoxy, and the like) and each q independently can be an integer ranging from 1 to 4 or 1 to 5, such as 1, 2, 3, 4, or 5.

With reference to Formula IV, $R^5$ is a phenyl ether-containing group, such as

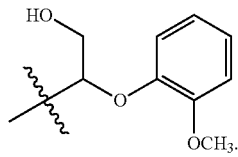 [SMILES: *C(CO)Oc1ccccc1OC]

With reference to Formula V, R' can be hydrogen, aliphatic, heteroaliphatic, or aromatic; and s is an integer ranging from 1 to 5, such as 1, 2, 3, 4, or 5.

Probes of Formula III also can have structures satisfying any one or more of Formulas IIIA, IIIB, or IIIC, illustrated below.

Formula IIIA
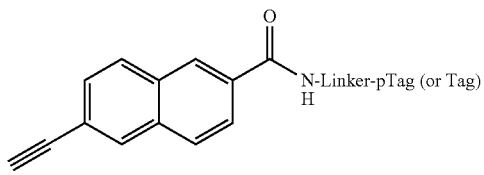
Formula IIIB
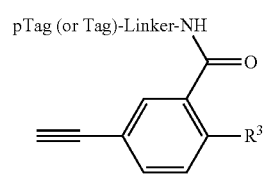
Formula IIIC
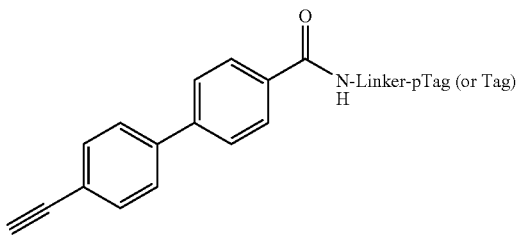
Exemplary probes of Formulas III, IIIA-IIIC, IV, and V are illustrated below:
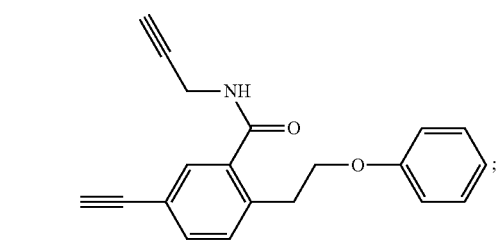
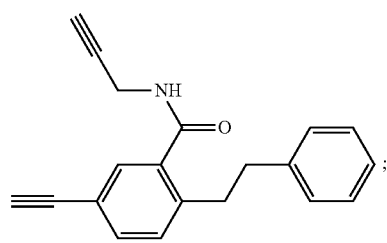
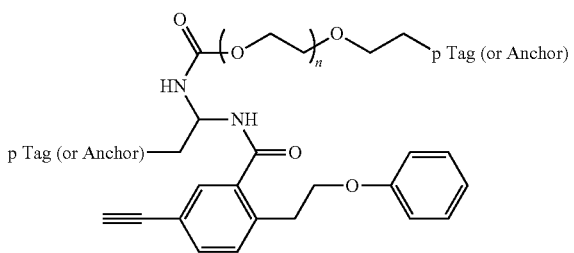
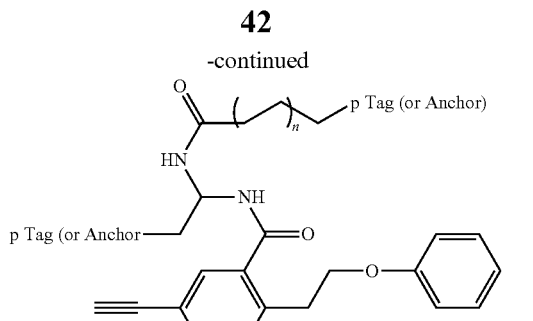
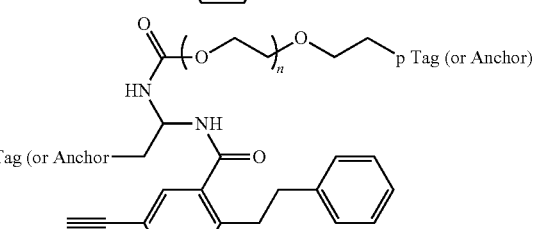
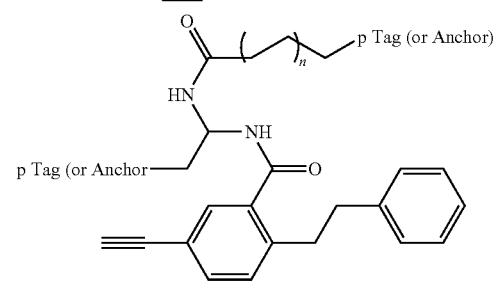
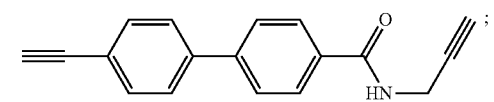
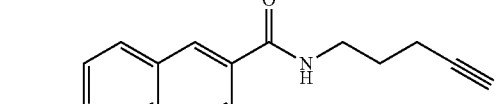
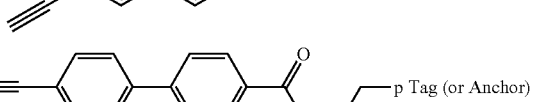
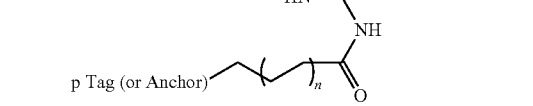
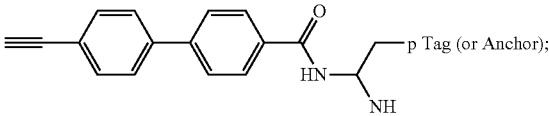
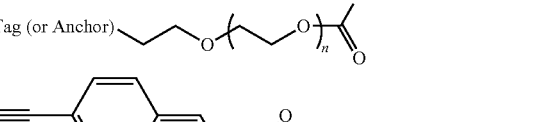
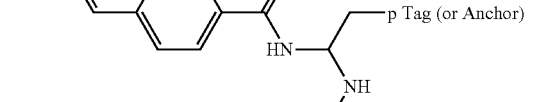

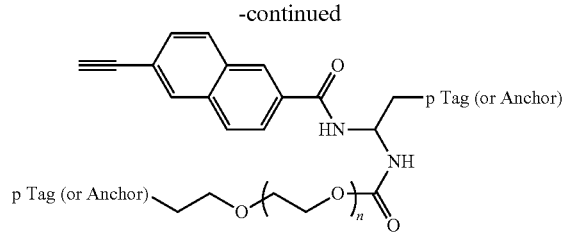
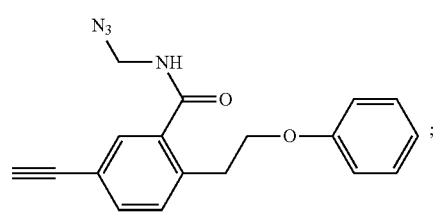
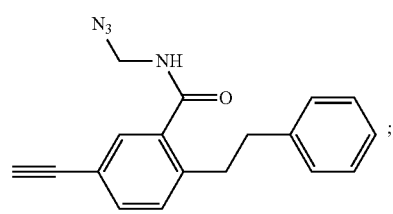
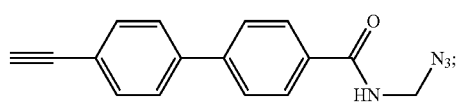
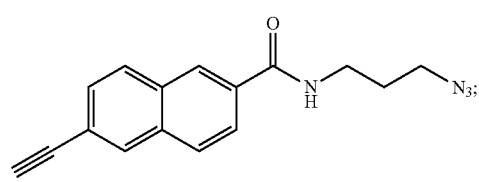
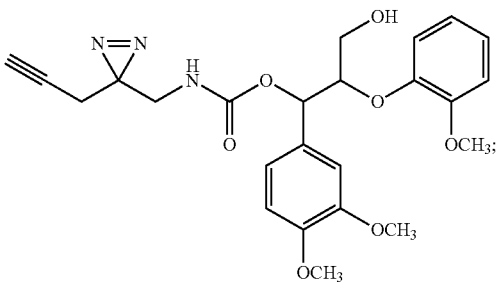
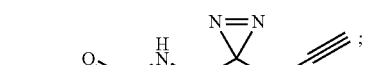
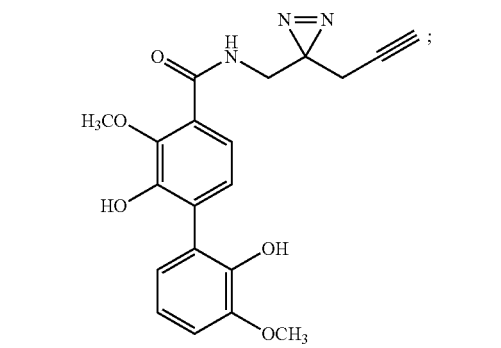
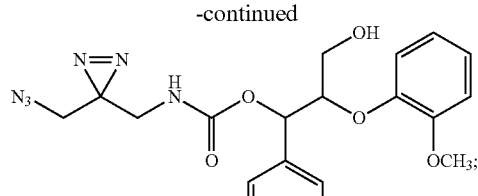
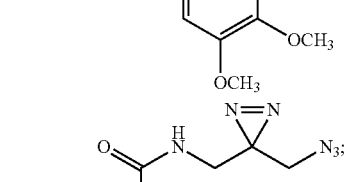
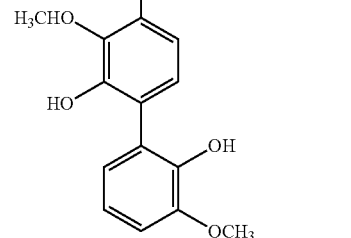
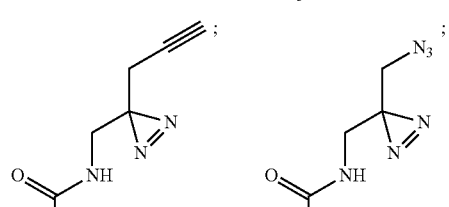
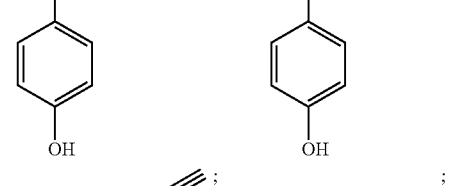
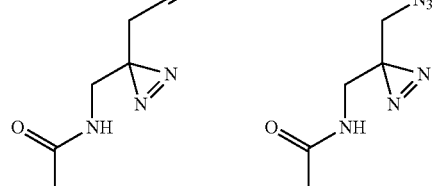
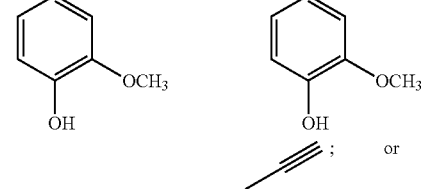
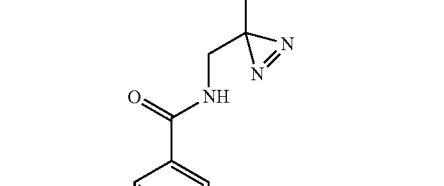
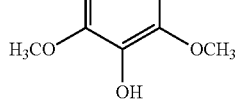

-continued

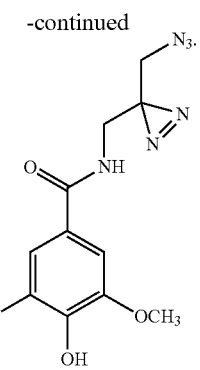

Methods for making probe embodiments used for characterizing extracellular peroxidase enzymes and/or lignin monomers (that is, probes of Formulas III, IV, and V) also are disclosed. Such methods can comprise reacting an aryl precursor comprising an alkyne moiety and a carboxylic acid group and optionally comprising an $R^3$ group, or an aryl precursor comprising one or more $R^4$ groups and a carboxylic acid group with an amine-terminated group that comprises the linker and the pTag (or Tag) group or an amine-terminated group that comprises the linker, the pTag (or Tag) group, and a photoactivatable moiety (for example, a diazirine or a benzophenone). Amide bond forming conditions recognizable to those of ordinary skill in the art with the benefit of the present disclosure can be used (for example, using a base and an amide forming coupling reagent, like HOBt, DCC, HATU, TBTU, PyBOP, or the like).

B. Chitin Degradation Probes

Also disclosed herein are embodiments of probes that can be used to target and identify enzymes involved in chitin degradation and thus can be used to evaluate carbon and nitrogen cycles involved in soil biomes. In particular disclosed embodiments, the probes can target species involved in chitin degradation, including lytic polysaccharide monooxygenases (LPMOs), β-N-acetyl-hexosaminidases, and other chitinases (for example, chitinases belonging to families 18, 19, and 20). The probes also can be used to analyze the activity of such enzymes and assess their roles in carbon and nitrogen cycling.

Lytic polysaccharide monooxygenases work synergistically with chitinases to disrupt the crystalline structure of chitin and cleave the polysaccharide chain existing in crystalline forms. LPMOs are mono-copper enzymes capable of cleaving glyosidic bonds via an elimination reaction. Chitinases are hydrolytic enzymes that reduce chitin into mono- and oligosaccharides. It has been determined that complete lysis of insoluble chitin polymer occurs in three main steps: (1) cleaving the polymer into water-soluble oligomers, (2) splitting of these oligomers into dimers, and (3) cleavage of the dimers into monomers. LPMOs and chitinases can promote the first step, chitinases of the chitinase family 18 can be involved in the second step, and other chitinases, such as β-N-acetyl-hexosaminidases can be involved in the third step.

Probe embodiments that can target LPMOs can have structures satisfying Formula VI, VIA or VIB illustrated below. These probes comprise an alkyne moiety that can be oxidized to a reactive ketene intermediate that will then covalently bond with the LPMOs and also comprise a glucosamine-based skeleton that further promotes selective reactivity with the LPMOs.

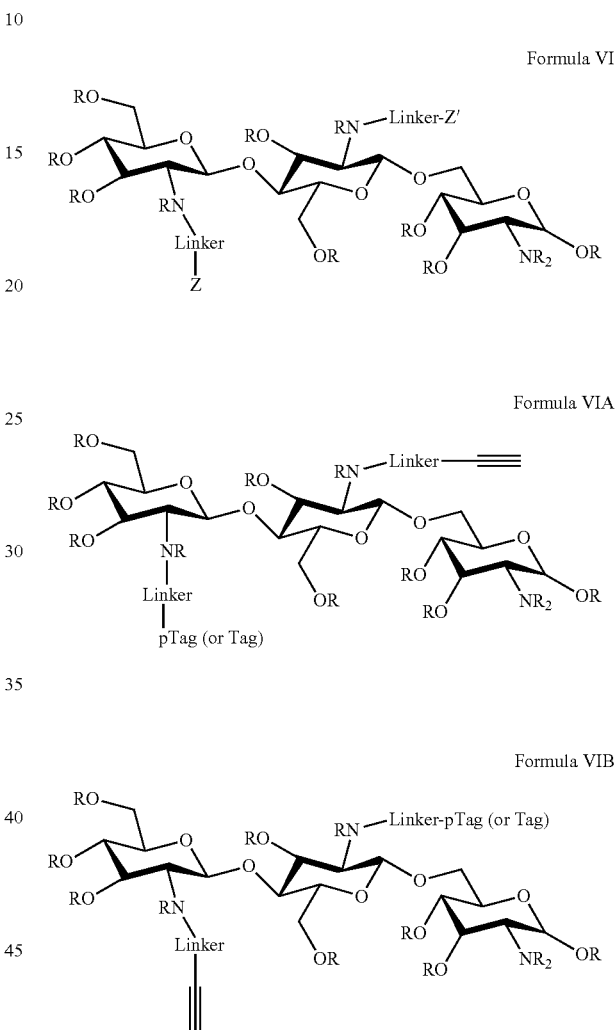

With reference to Formula VI, VIA, and VIB, each linker independently can be selected from an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; the pTag group comprises a clickable functional group. In particular disclosed embodiments, each linker group independently is an aliphatic linker group, such as an alkyl, alkenyl, or alkynyl group, with particular embodiments comprising a lower alkyl group, such as $-(CH_2)_m$, wherein m is an integer selected from 1 to 10, such as 1 to 8, or 1 to 6, or 1 to 4, or 1 to 3; or an heteroaliphatic linker, such as an alkylene oxide (for example, PEG). In particular disclosed embodiments, the linker is a heteroaliphatic linker comprising a carbonyl group and an aliphatic group, such as an alkyl, alkenyl, or alkynyl group, with particular embodiments comprising a lower alkyl group, such as —(CH$_2$)$_m$, wherein m is an integer selected from 1 to 10, such as 1 to 8, or 1 to 6, or 1 to 4, or 1 to 3. In yet additional embodiments, the linker can be a heteroaliphatic linker comprising a carbonyl group and a heteroaliphatic group, such as an alkylene oxide (for example, PEG). In yet additional embodiments, the linker group can be a bi-functional linker as described herein. Any such bi-functional linkers can be used with these probe embodiments. In particular embodiments, the pTag group is an azide or an alkyne. If the probe comprises a pre-installed Tag group, the Tag group can be a detectable moiety, such as a fluorophore, a chromogen, or a member of a specific binding pair (for example, biotin or streptavidin).

In particular embodiments, probes for LMPOs can be selected from exemplary species provided below:

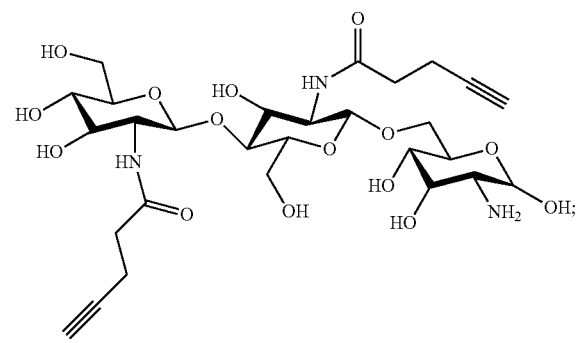

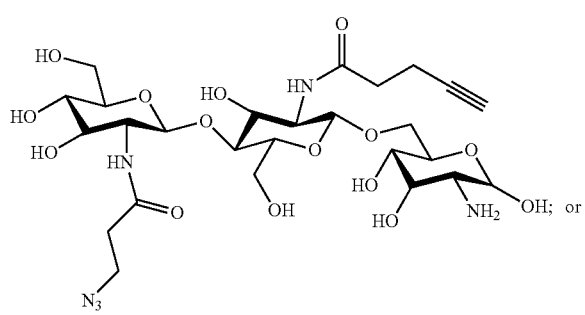

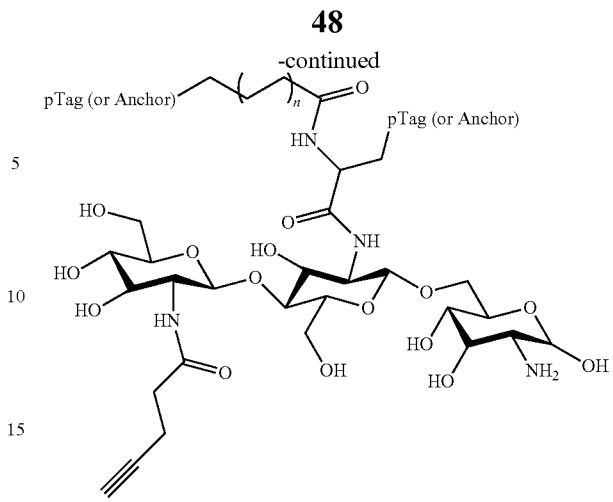

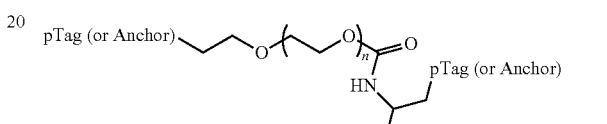

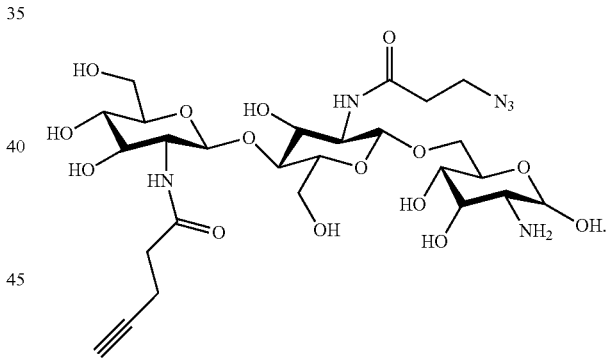

Methods of making the probe embodiments described above also are provided herein. Probe embodiments used to target LPMOs can be made using steps illustrated below in Scheme 3.

Scheme 3

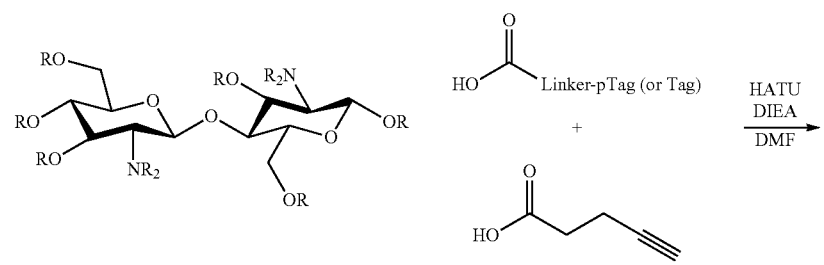

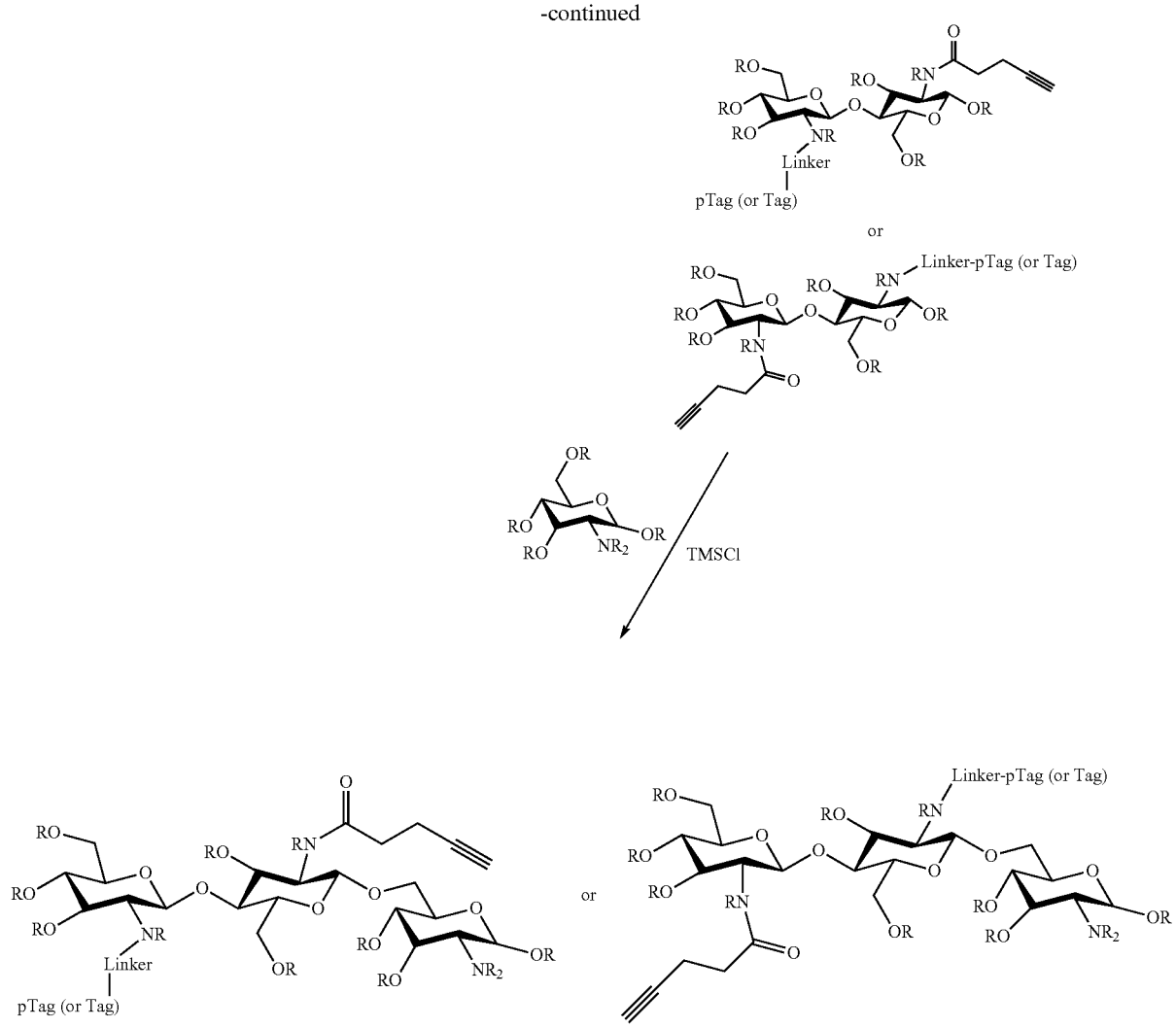
An exemplary method of making a probe for targeting LPMOs is illustrated below in Scheme 4.
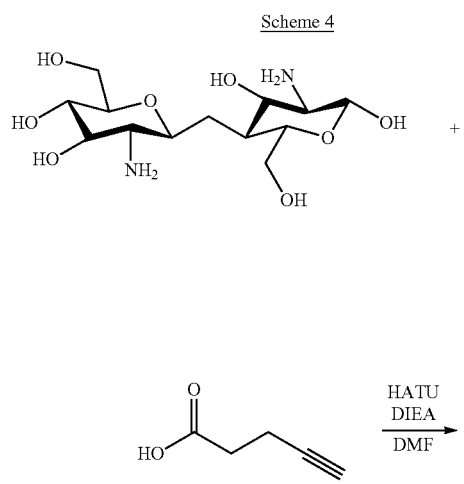
Scheme 4
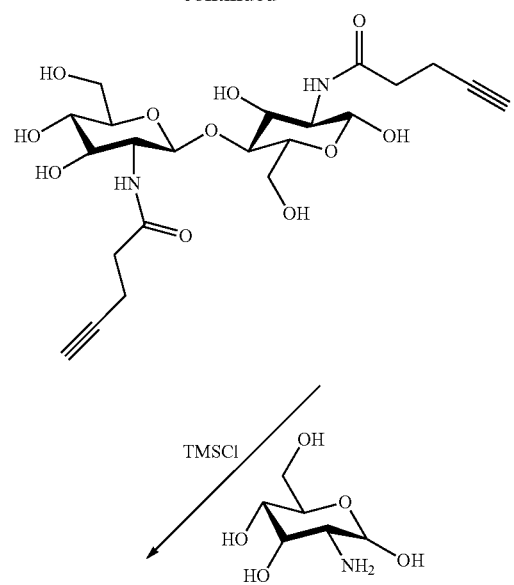

-continued

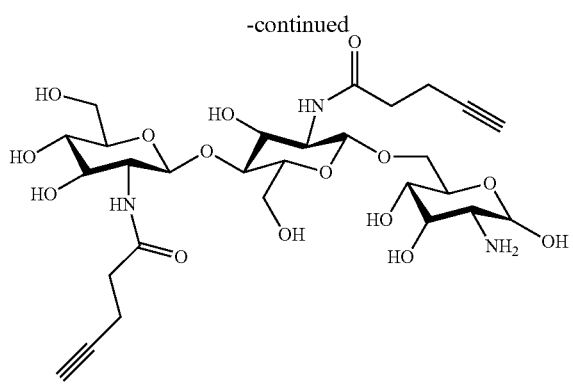

Probes that can be used to identify and analyze chitinases, including those of family 18 and β-N-acetyl-hexosaminidases, have structures satisfying Formula VII or VIII, illustrated below. These probes comprise a reactive isoxazolium group that undergoes a base-mediated ring opening step to form a ketenimine that reacts with a functional group on the chitinase (for example, a carboxylic acid group) to form an enamide, thereby binding the probe to the enzyme target.

Formula VII

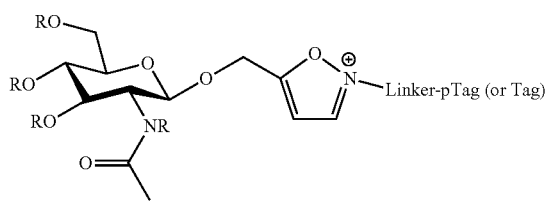

Formula VIII

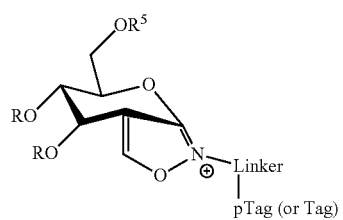

With reference to Formulas VII and VIII, each linker independently can be selected from linker group can be an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; each R independently is hydrogen, aliphatic, or a protecting group; the pTag group comprises a clickable functional group. In particular disclosed embodiments, each linker group independently is an aliphatic linker group, such as an alkyl, alkenyl, or alkynyl group, with particular embodiments comprising a lower alkyl group, such as —$(CH_2)_m$—, wherein m is an integer selected from 1 to 10, such as 1 to 8, or 1 to 6, or 1 to 4, or 1 to 3; or an heteroaliphatic linker, such as an alkylene oxide (for example, PEG). In yet additional embodiments, the linker group can be a bi-functional linker as described herein. Any such bi-functional linkers can be used with these probe embodiments. In particular embodiments, the pTag group is an azide or an alkyne. If the probe comprises a pre-installed Tag group, the Tag group can be a detectable moiety, such as a fluorophore, a chromogen, or a member of a specific binding pair (for example, biotin or streptavidin). Also, with reference to Formula VIII, $R^5$ can be hydrogen or a thiocarbamide-containing saccharide moiety (for example, a mono-, di-, tri-, or oligosaccharide). An exemplary thiocarbamide-containing saccharide is illustrated below:

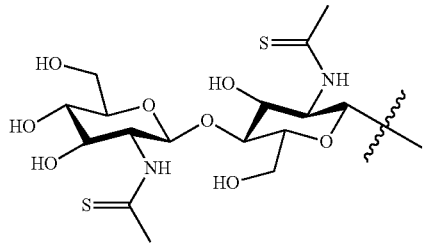

In particular embodiments, probes for chitinases can be selected from exemplary species provided below:

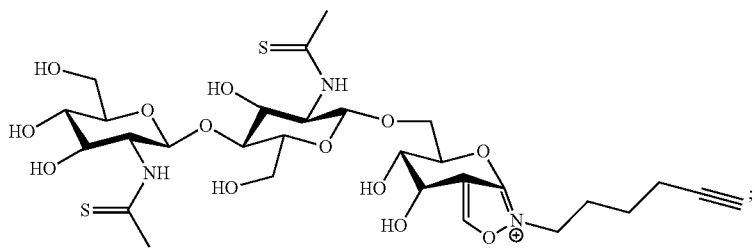

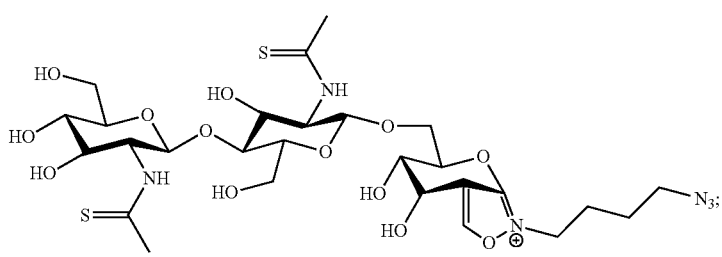

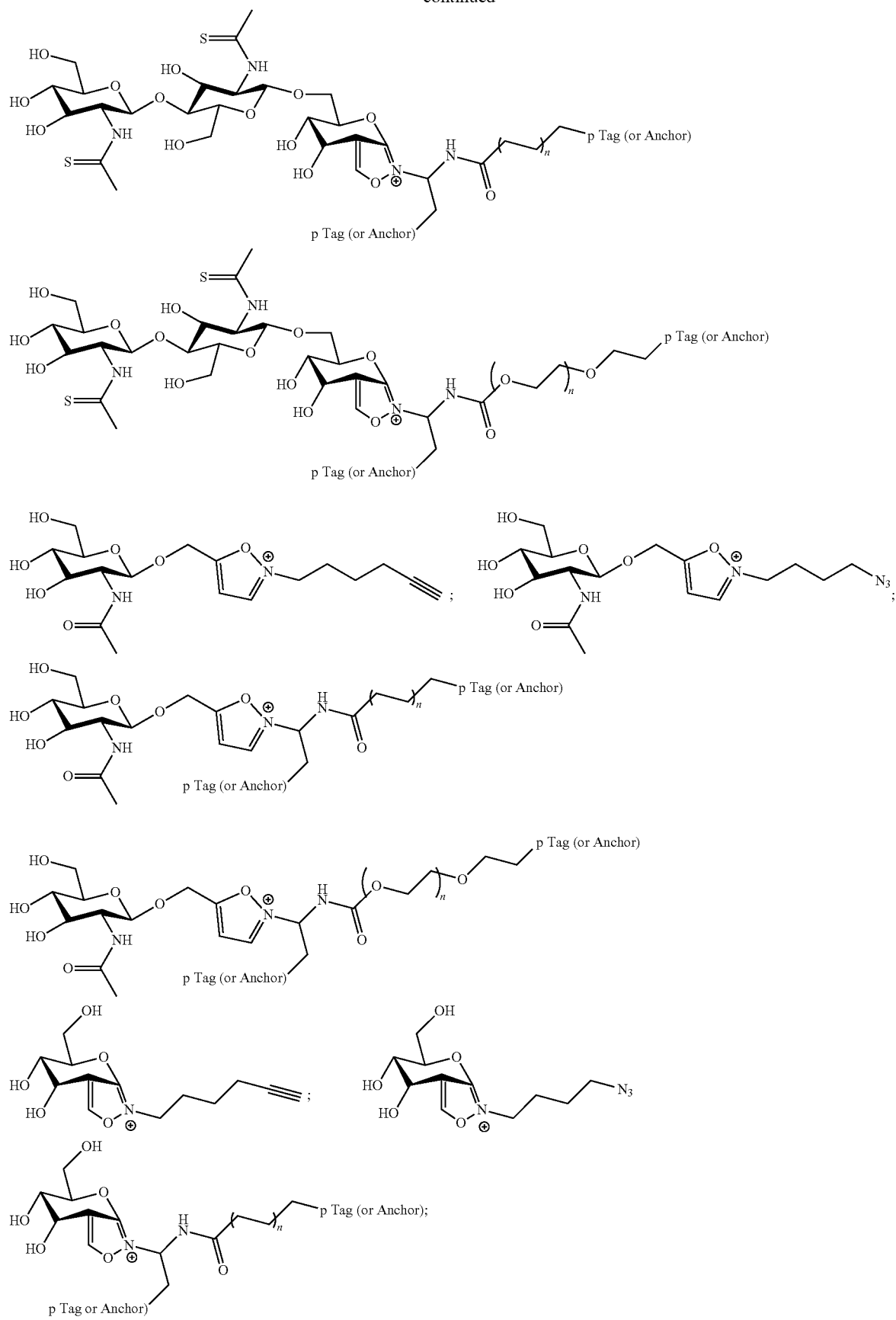

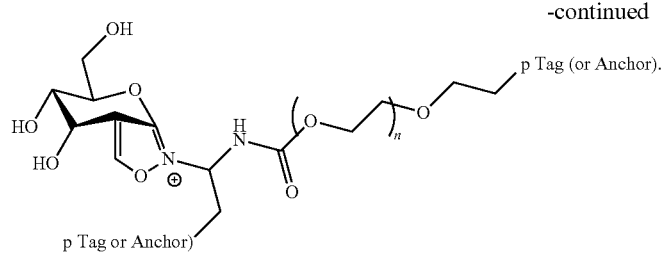
Probe embodiments used to target chitinases (including β-N-acetyl-hexosaminidases) can be made using steps illustrated below in Schemes 5-7.
Scheme 5
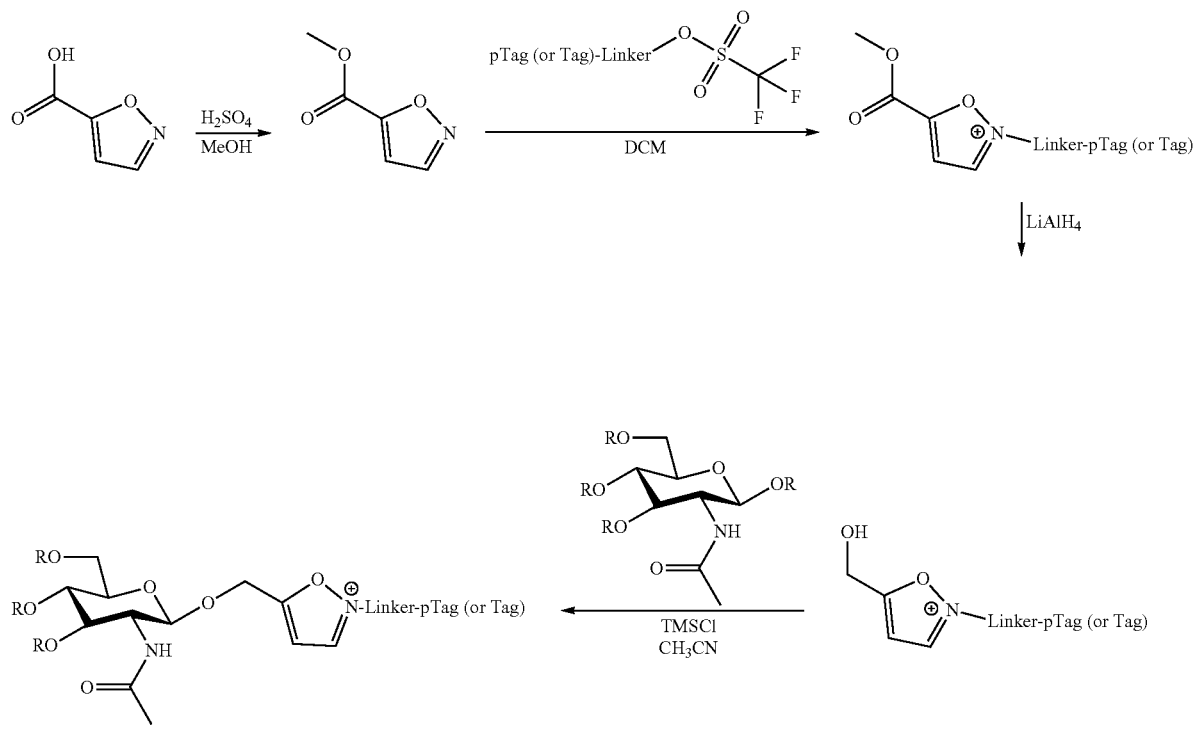
Scheme 6
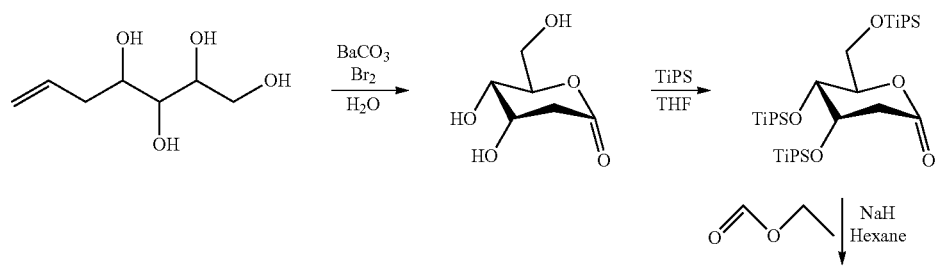

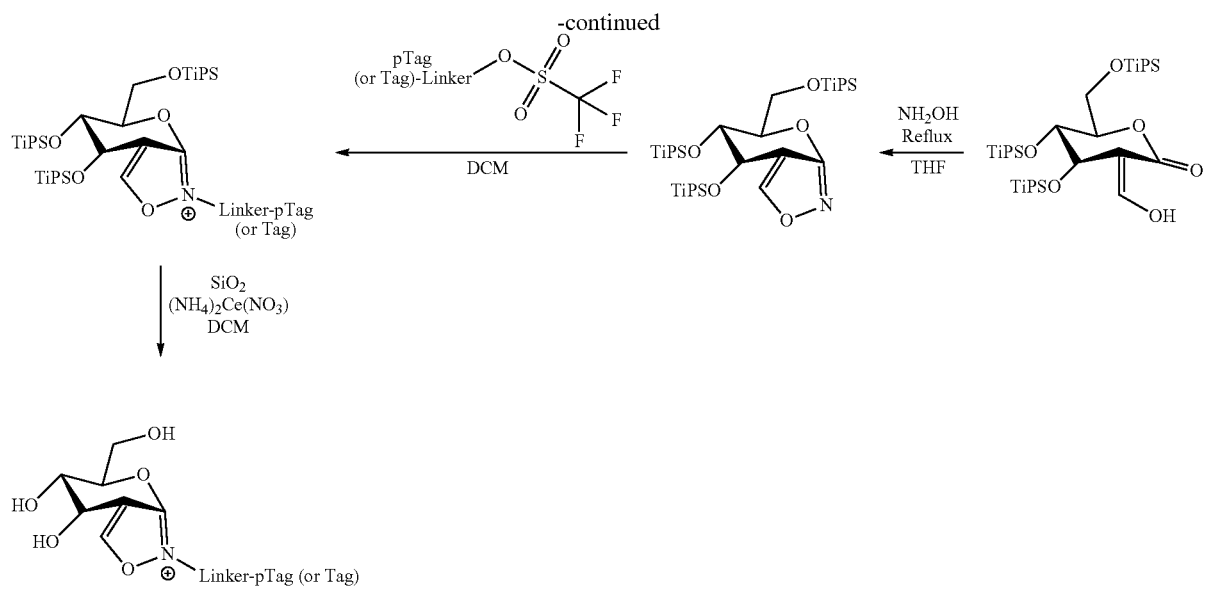
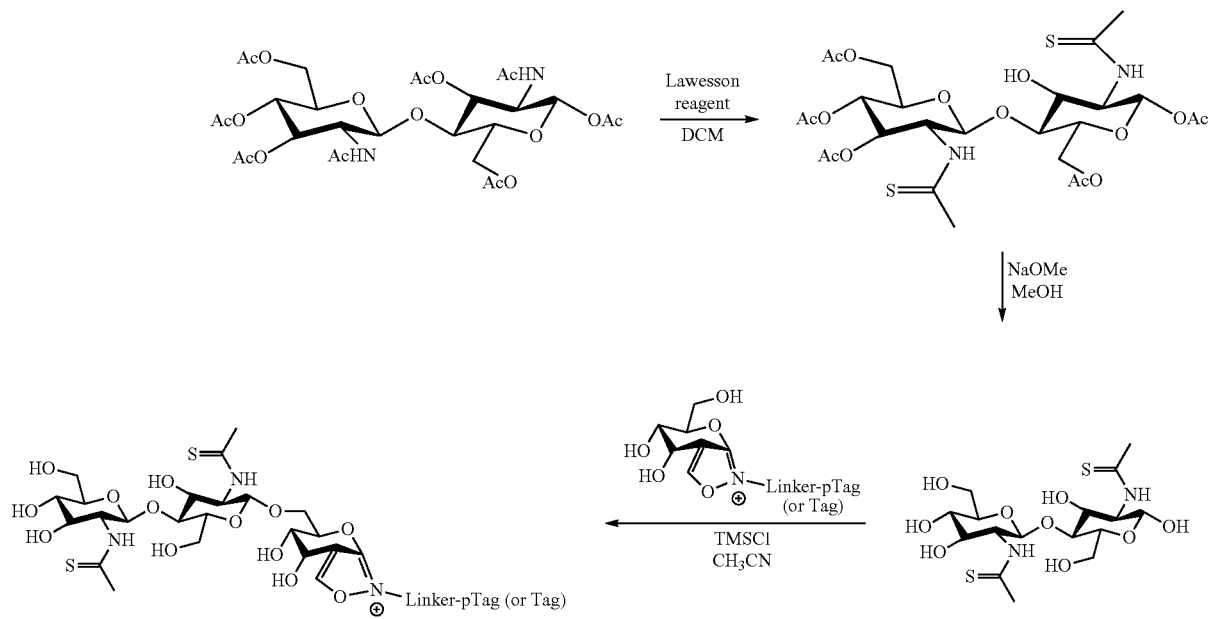
Exemplary methods for making chitinase probes described above are provided below in Schemes 8-10.
Scheme 8
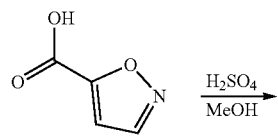

59
60
-continued
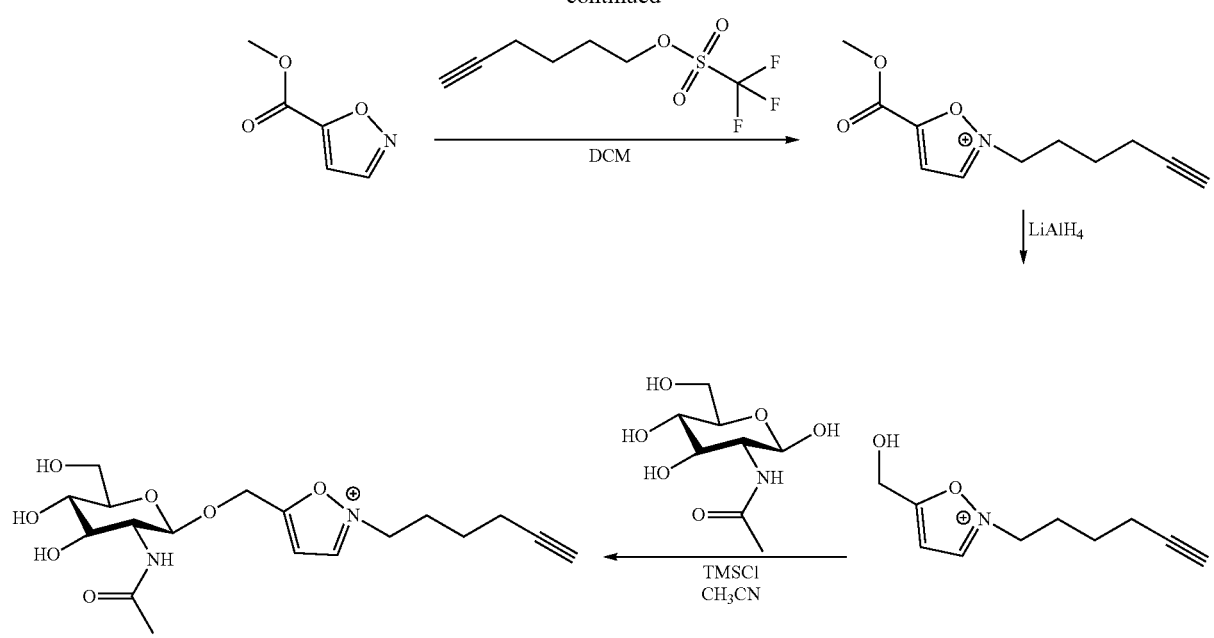
Scheme 9
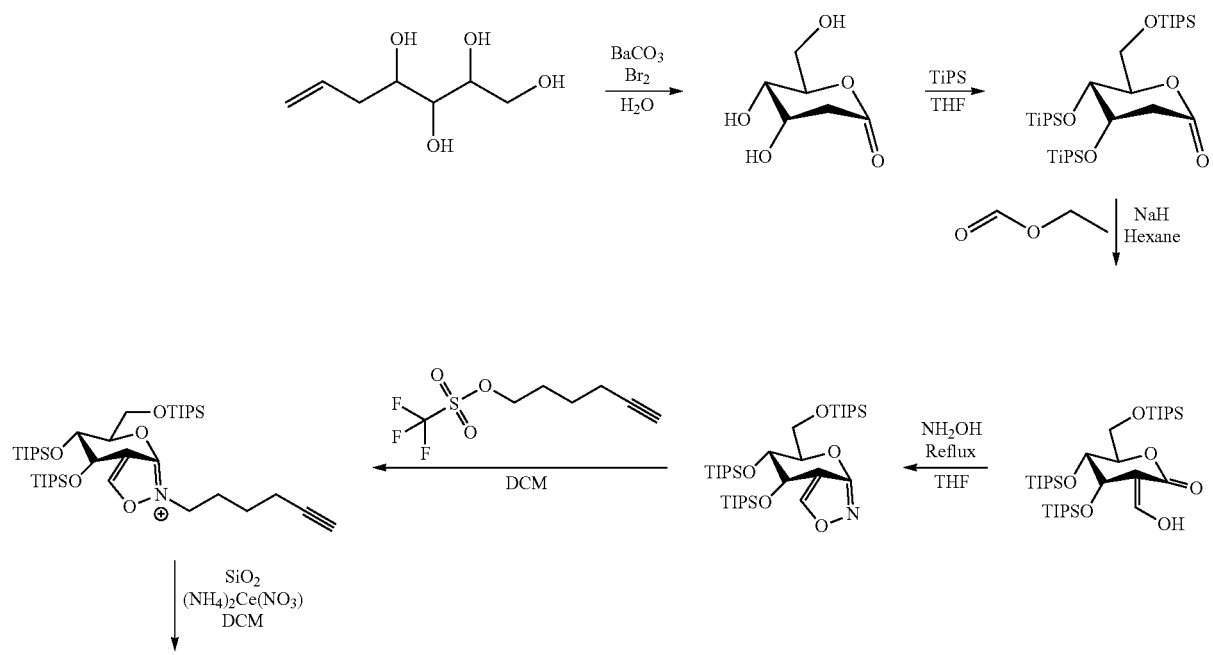
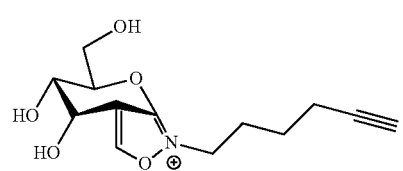

Scheme 10

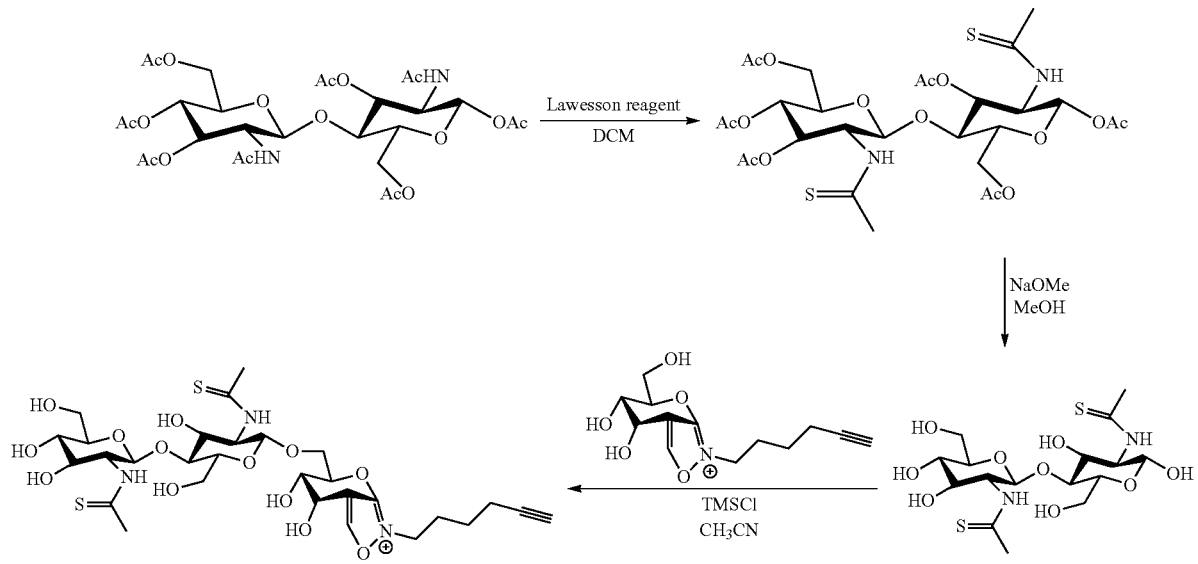

C. Nutrient and Toxin Analysis

Certain probe embodiments disclosed herein can be used to evaluate environment health and productivity, such as water, air, soil, or plant health and productivity. Plants employ critical symbioses through their root structures with microorganisms that enables the acquisition of essential nutrients. The soil microbiome around a plant, such as the microbiome surrounding the plant's roots (known as the rhizosphere) and the microbes that grow directly on the plant's roots (known as endophytes), plays important functional roles that facilitate plant nutrient acquisition of various nutrients (for example, macronutrients like carbon, nitrogen, phosphorous, and sulfur), thereby promoting growth and resistance to environmental perturbations such as wetting and drought. Additionally, other environments, such as the air and/or water, surrounding a plant can be evaluated to access environment health and productivity. At present, understanding the functions that the soil microbes perform, and their relative activities is almost entirely inferred from metagenomic content; however, these inferences are poor, at best. For instance, subtle changes in moisture or pH can dramatically alter enzyme activities, but that cannot be identified or predicted from a genome. As such, there is a need for technologies that rapidly characterize functional soil microbiome activities at native physiological conditions to thereby provide a means for predicting plant growth and response to change/stress. Such measurements can be achieved using probe embodiments disclosed herein and thus these probes can be used to predict plant health and growth. In particular embodiments, the probes predict plant health and growth by determining the activity levels of microbiome functions that provide nutrients to plants. This information can be used, for example, to determine suitable marginal lands for biofuel production, characterize soil microbiome health and thereby plant health due to climate change, and increase crop yield and productivity for agricultural lands. Solely by way of example, probes disclosed herein can be used to profile plant-associated soil microbiome functions for sulfatases (S-acquisition), phosphatases (P-acquisition), ammonia monooxygenases and peptidases (N-acquisition), and glycosidases (C-acquisition).

Probes for soil nutrient and toxin analysis can have any of the structures described below and further include the probes described above for glycoside hydrolase enzymes. In some embodiments, the probe is a sulfatase probe and thus can be used to evaluate sulfur acquisition. In some embodiments, the probe is a phosphatase probe and thus can be used to evaluate phosphate acquisition. In some embodiments, the probe is an ammonia monooxygenase (AMO) probe and/or a peptidase probe, both of which can be used to evaluate nitrogen acquisition. In some embodiments, the probe is a glycoside hydrolase probe and thus can be used to evaluate carbon acquisition.

Sulfatase and phosphatase probe embodiments that can be used can have structures satisfying Formula IX, illustrated below. These probe embodiments comprise a binding group that is first cleaved from the probe by the sulfatase or phosphatase to produce an activated probe comprising a quinone methide group, which can then be bound to the sulfatase or the phosphatase.

Formula IX

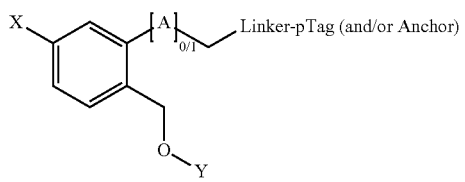

With reference to Formula IX, X can be the binding group of the probe and thus can be a moiety that is targeted by the analyte, such as a sulfatase or a phosphatase; Y can be a Tag moiety or —C(O)NPh-Z, wherein Z is aldehyde, ketone, ester, carboxylic acid, acyl, acyl halide, cyano, sulfonate, nitro, nitroso, quaternary amine, $CF_3$, or alkyl halide; A, if present, is O, $C(R)_2$, or NR (wherein each R independently is hydrogen, aliphatic, heteroaliphatic, or aromatic); the linker can be selected from an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; the pTag group, if present (such as when Y is not a Tag group), comprises a clickable functional group; and the anchor group (if present, such as when a bi-functional linker is used and/or when Y is a Tag group) comprises an activated ester, a halide, a carboxylic acid, or a clickable functional group. In particular disclosed embodiments, X is a sulfate group (for example, —OS(O)$_2$OR, wherein R is hydrogen, aliphatic, or a counterion that balances the negative charge on the corresponding oxygen atom, such as an alkali metal ion like K$^+$, Na$^+$, Li$^+$, or the like; an ammonium ion, or other positively charged ionized organic compounds) or a phosphate group (for example, —OP(O)(OR)$_2$, wherein each R independently is hydrogen, aliphatic, or a counterion that balances a negative charge on each corresponding oxygen atom, such as an alkali metal ion like K$^+$, Na$^+$, Li$^+$, or the like; an ammonium ion, or other positively charged ionized organic compounds). In particular embodiments, Y is 4-methyl-2H-chromen-2-one, —C(O)NPh-NO$_2$, or —C(O)NPh-CF$_3$. In particular disclosed embodiments, the linker group illustrated in Formula IX, is an aliphatic linker group, such as an alkyl, alkenyl, or alkynyl group, with particular embodiments comprising a lower alkyl group, such as —(CH$_2$)$_m$, wherein m is an integer selected from 1 to 10, such as 1 to 8, or 1 to 6, or 1 to 4, or 1 to 3. In yet additional embodiments, the linker group can be a bi-functional linker as described herein. Any such bi-functional linkers can be used with these probe embodiments. In particular embodiments, the pTag or the anchor group is an azide or an alkyne.

Representative probe embodiments that target sulfatases and phosphatases include those illustrated below:

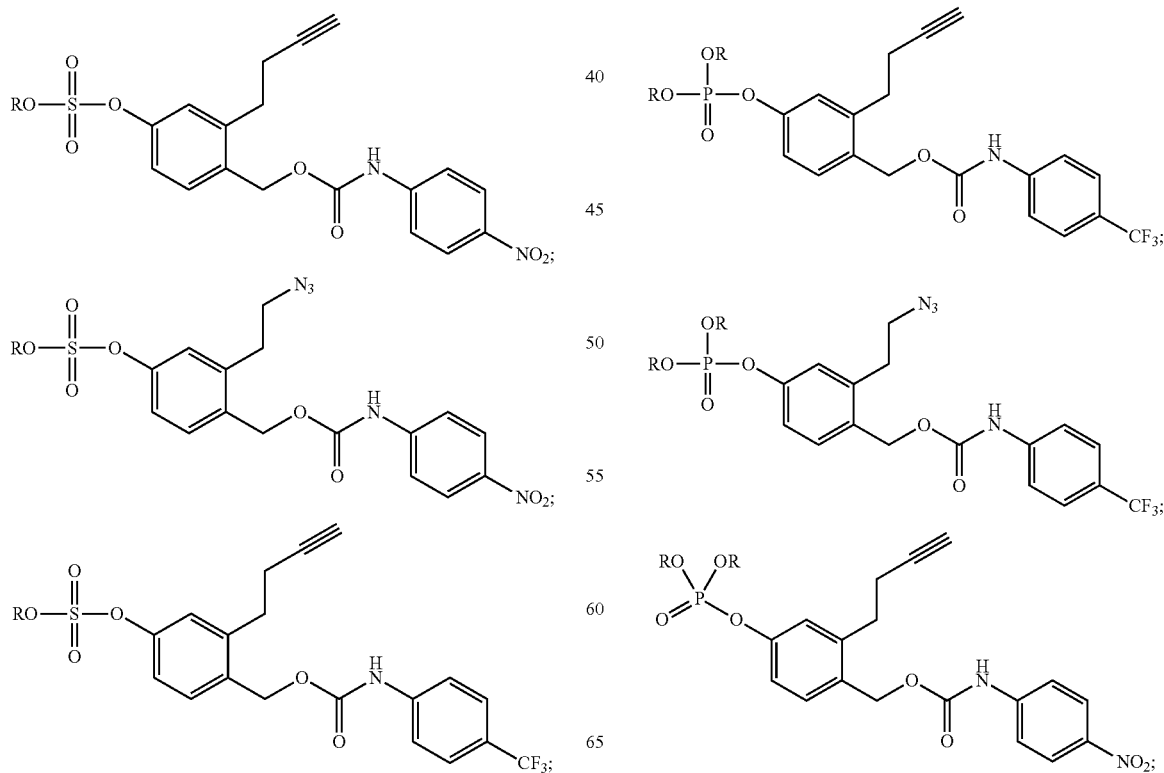

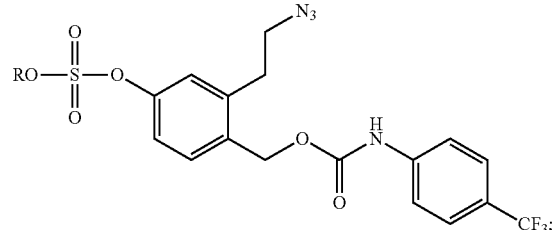

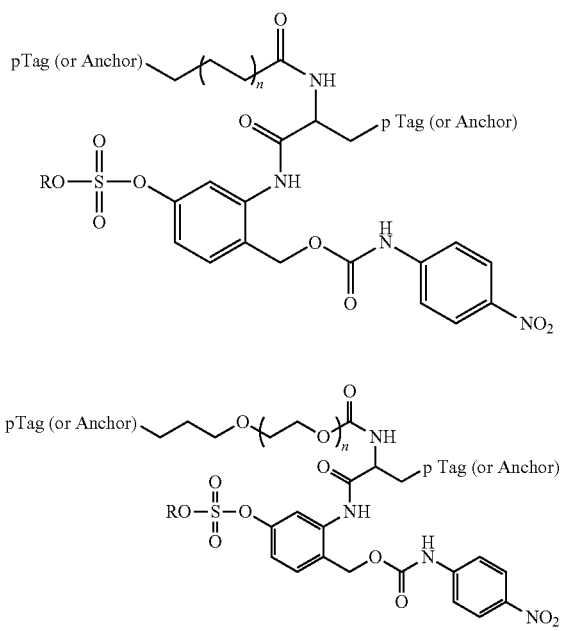

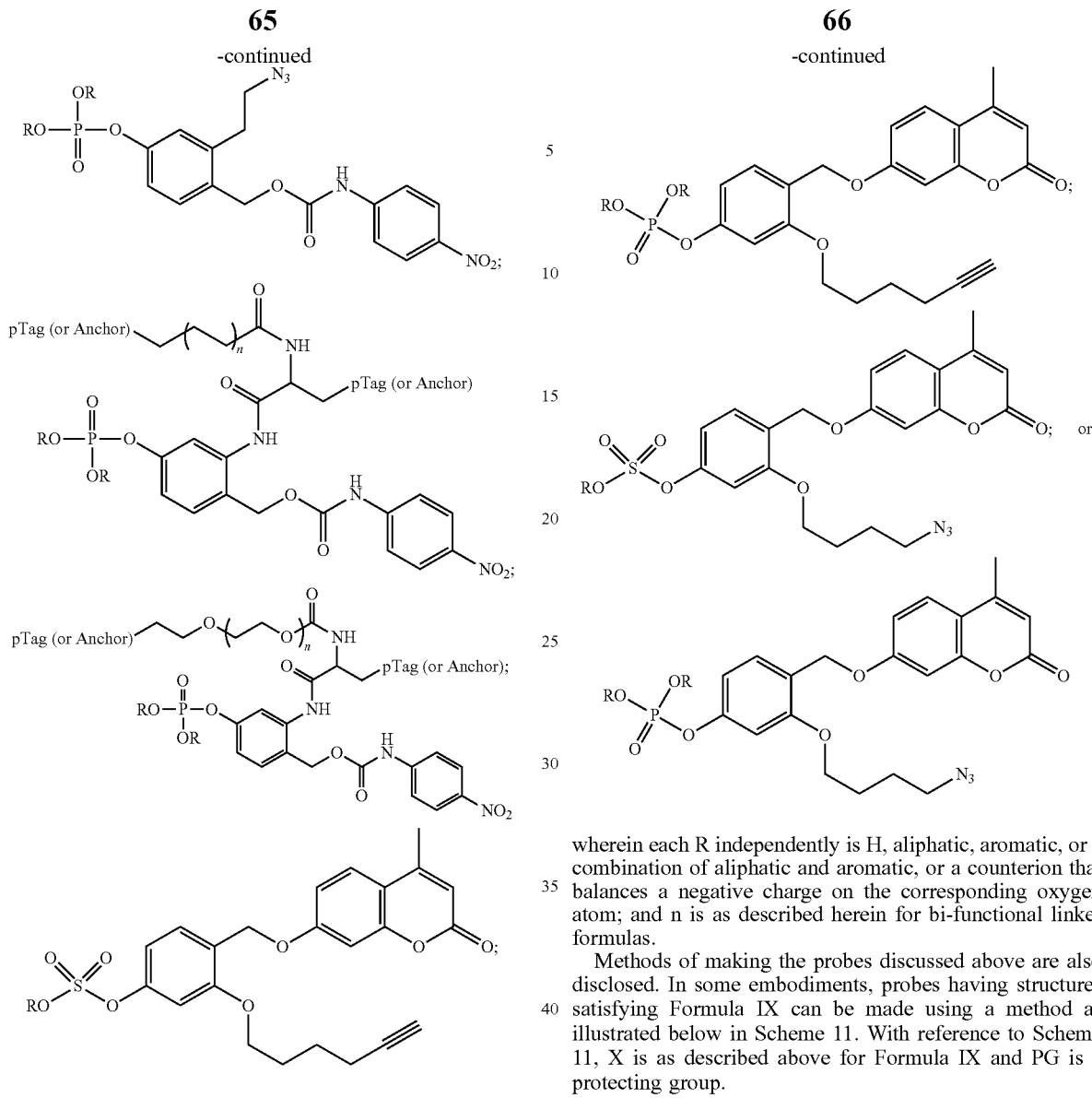

wherein each R independently is H, aliphatic, aromatic, or a combination of aliphatic and aromatic, or a counterion that balances a negative charge on the corresponding oxygen atom; and n is as described herein for bi-functional linker formulas.

Methods of making the probes discussed above are also disclosed. In some embodiments, probes having structures satisfying Formula IX can be made using a method as illustrated below in Scheme 11. With reference to Scheme 11, X is as described above for Formula IX and PG is a protecting group.

Scheme 11

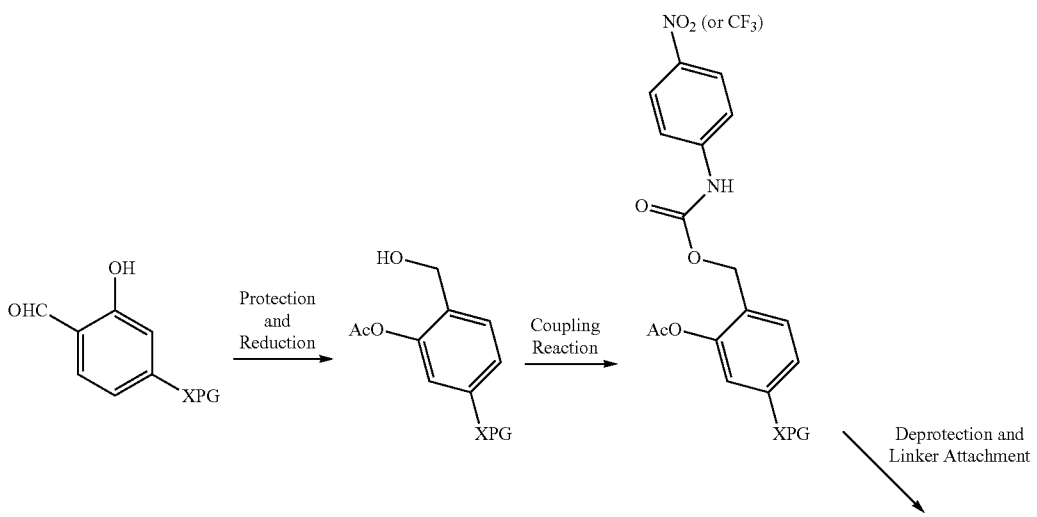

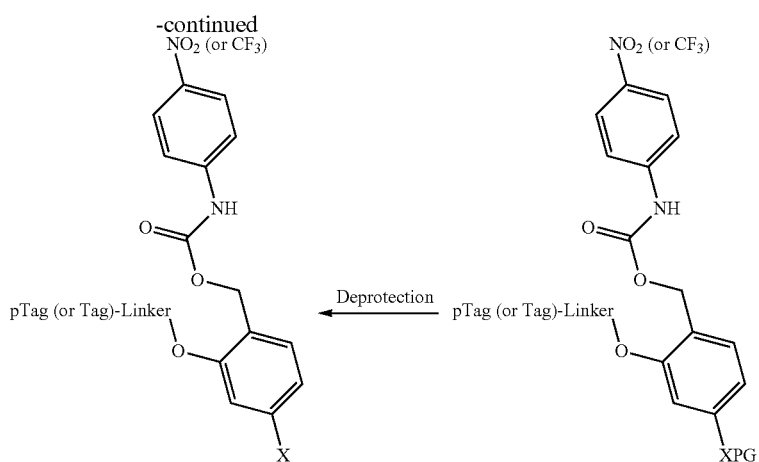
Additional probe embodiments can be made as described below in Schemes 12 and 13.
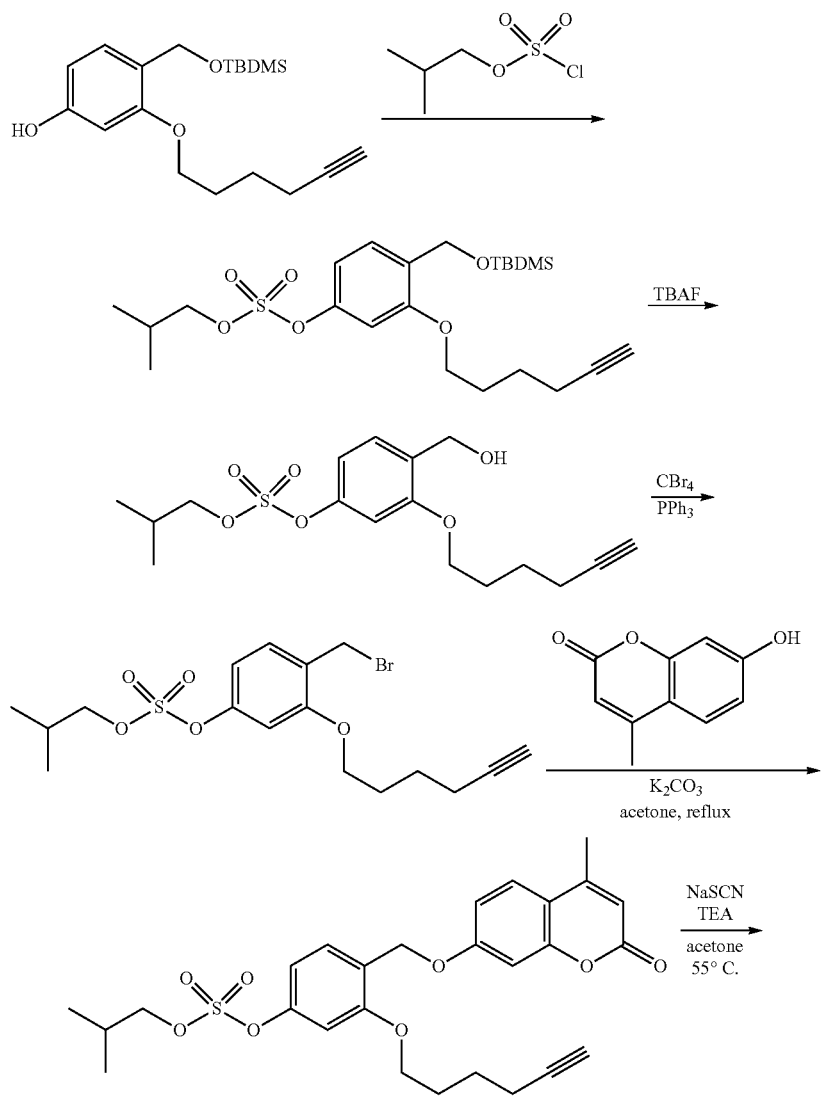

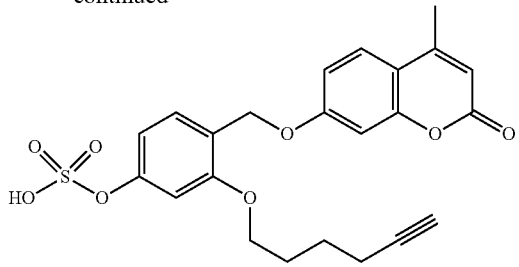

Scheme 13

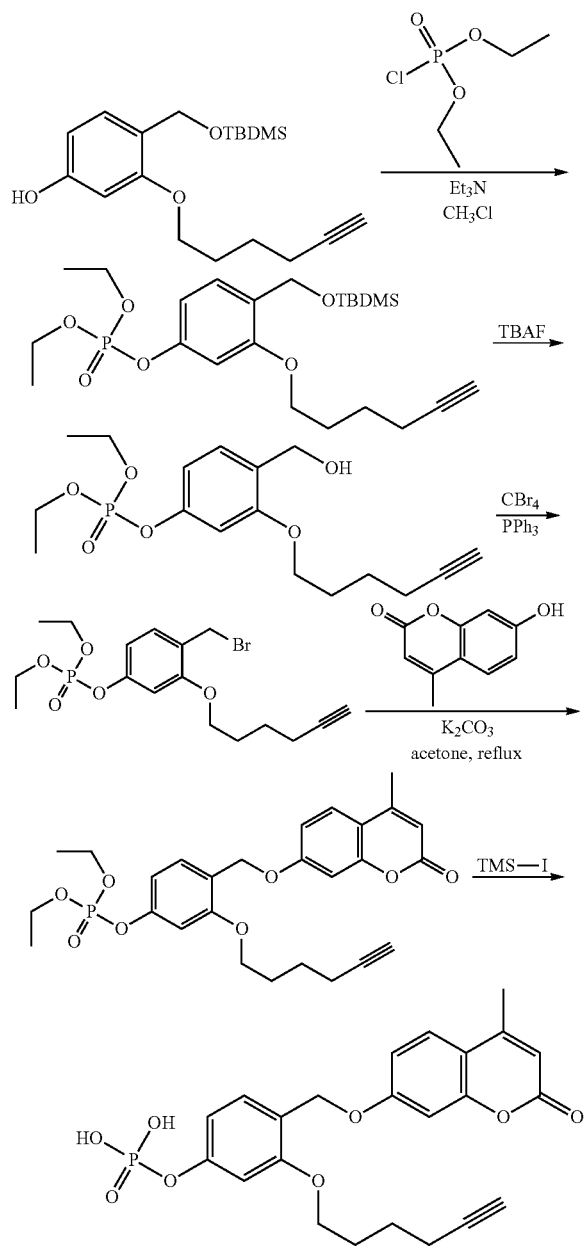

diate that becomes covalently attached to the enzyme. Probes that target AMO can have a structure satisfying Formula X.

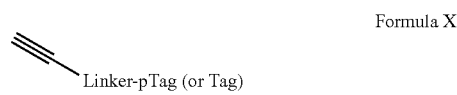

Formula X

With reference to Formula X, the linker can be selected from an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; and the pTag group comprises a click-able functional group. In particular disclosed embodiments, the linker group illustrated in Formula X, is an aliphatic linker group, such as an alkyl, alkenyl, or alkynyl group, with particular embodiments comprising a lower alkyl group, such as $-(CH_2)_m$, wherein m is an integer selected from 1 to 10, such as 1 to 8, or 1 to 6, or 1 to 4, or 1 to 3; or an heteroaliphatic linker, such as an alkylene oxide (for example, PEG). In yet additional embodiments, the linker group can be a bi-functional linker as described above. Any such bi-functional linkers can be used with these probe embodiments. In particular embodiments, the pTag group is an azide or an alkyne.

Representative probe embodiments that target AMO include those illustrated below:

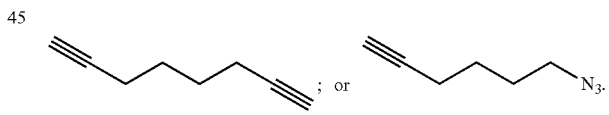

Also disclosed herein are probe embodiments that target serine proteases and peptidases. Such probes can have structures satisfying Formula XI

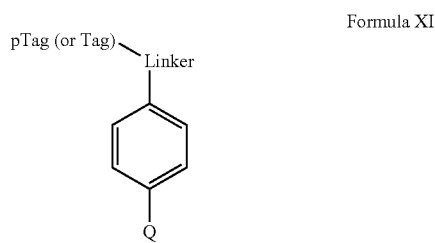

Formula XI

With reference to Formula XI, Q is a cysteine-reactive group, such as a functional group comprising at least one In yet additional embodiments, probes that can target AMO can be used. These probes comprise an alkyne moiety that is activated by the AMO to provide a reactive intermealkene; the linker can be selected from an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; and the pTag group comprises a clickable functional group. In particular disclosed embodiments, Q is —OS(O)$_2$CH=CH$_2$. In an independent embodiment, Q is not —OS(O)$_2$CH=CH$_2$ when pTag is an alkyne and the linker is —CH$_2$OCH$_2$—. In particular disclosed embodiments, the linker group is an aliphatic linker group, such as an alkyl, alkenyl, or alkynyl group, with particular embodiments comprising a lower alkyl group, such as —(CH$_2$)$_m$, wherein m is an integer selected from 1 to 10, such as 1 to 8, or 1 to 6, or 1 to 4, or 1 to 3; or an heteroaliphatic linker, such as an alkylene oxide (for example, PEG). In yet additional embodiments, the linker group can be a bi-functional linker as described above. Any such bi-functional linkers can be used with these probe embodiments. In particular embodiments, the pTag group is an azide or an alkyne.

Representative probe embodiments that target serine proteases and peptidases include those illustrated below:

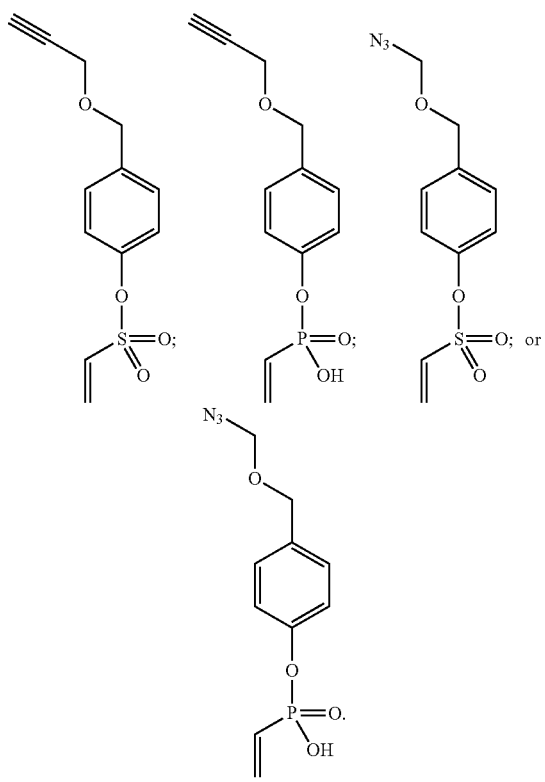

Also disclosed herein are probe embodiments that can be used to evaluate downstream effects of toxins introduced into soil and/or aquatic environments by pesticides or other sources. As such, the metabolism of such compounds can be analyzed and any primary and off targets of such compounds can be identified. Organophosphates are active ingredients in pesticides used in the agricultural community and are toxins that can contribute to environmental contamination and can negatively impact human and animal health. Similarly, organophosphonates can be introduced into soil and/or aquatic environments downstream of industrial sites. As such, it is important to know the mechanistic pathways that organophosphates and organophosphonates take when introduced into soil and/or aquatic microbiomes. Probe embodiments disclosed herein can be used to mimic organophosphates and organophosphonates and thus can used to determine how sources of these compounds impact microbial and plant processes by identifying primary and off targets of any organophosphates and/or organophosphonates present in a soil or water sample.

In some embodiments, the probe is an organophosphate probe and it has a phosphate core structure that comprises an anchor group and a tag moiety (or a precursor thereof) that provides (or can be modified to provide) a detectable signal bound to oxygen atoms of the phosphate core structure. In some such embodiments, the probe has these components and further comprises a functional group that is similar in structure to functional groups of various pesticides or toxins, such as parathion, paraoxon, nibufin, armin, chlorpyrifos, diazinon, metrifonate, dichlorvos, fensulfothion, chlorfenvinphos, prothiophos, profenofos, quinalphos, coumaphos, potasan, demeton, malathion, monocrotophos, pirimiphos-methyl, fenthion, fenitrothion, pyrazophos, triazofos, cresyl saligenin phosphate, and the like. Particular functional groups of such pesticides and toxins are illustrated below:

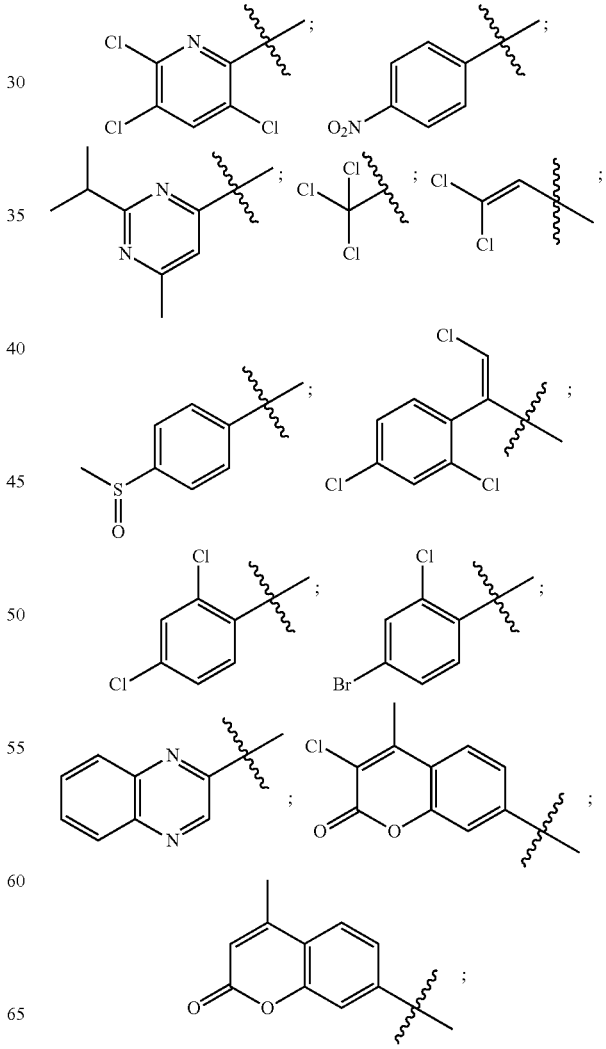

-continued

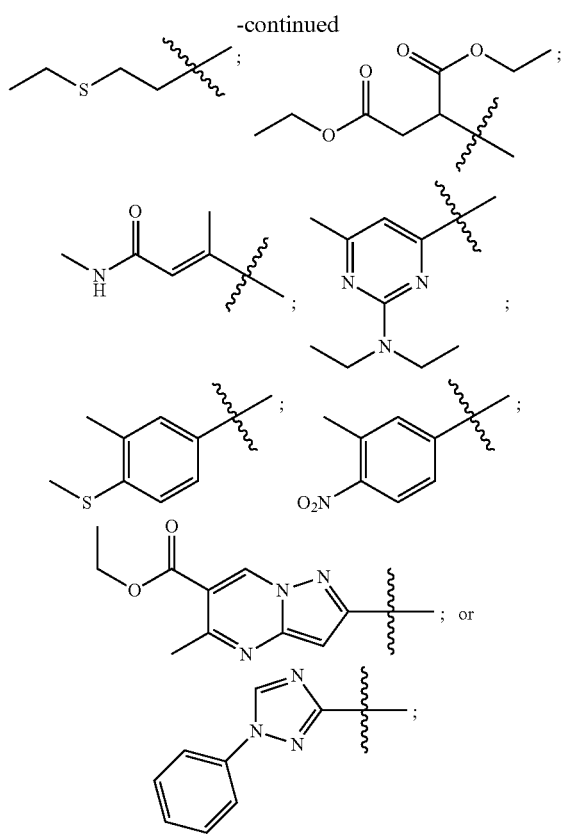

Probes that can be used in such embodiments can have structures satisfying Formula XII.

Formula XII

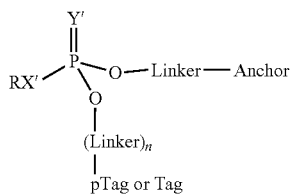

With reference to Formula XII, X' can be —C(H)(OH)—, oxygen or sulfur; Y' can be oxygen or sulfur; R can be hydrogen, aliphatic, heteroaliphatic, haloaliphatic, aromatic, any $^{13}$C-labeled version thereof and/or combinations thereof; each linker independently can be selected from an aliphatic group, a heteroaliphatic group, an aromatic group, an aliphatic-aromatic group, a heteroaliphatic-aromatic group, a heteroaromatic group, an aliphatic-heteroaromatic group, or a heteroaliphatic-heteroaromatic group; the pTag group, if present (such as when a Tag group is not used), comprises a clickable functional group; the Tag group, if present (such as when a pTag group is not used), comprises a detectable moiety, such as a chromogen, a fluorophore, a detectable isotopic moiety (for example, $^{13}$CH$_3$ or $^{13}$CH$_2$$^{13}$CH$_3$) or the like; the anchor group comprises a clickable functional group, such as alkyne or azide; and n is 0 or 1. In particular embodiments, R is any of the pesticide/toxin functional groups illustrated. In particular embodiments, n is 1, the linker group is an alkylene oxide (such as PEG) or lower alkyl (such as —(CH$_2$)$_m$, wherein m is an integer selected from 1 to 10, such as 1 to 8, or 1 to 6, or 1 to 4, or 1 to 3) and a pTag group is present and is alkyne or azide. In particular disclosed embodiments, n is 0 and a Tag group is present and is a fluorophore. In particular disclosed embodiments, the anchor group is an alkyne or an azide.

Representative probe embodiments that can be used to mimic organophosphate compounds are illustrated below.

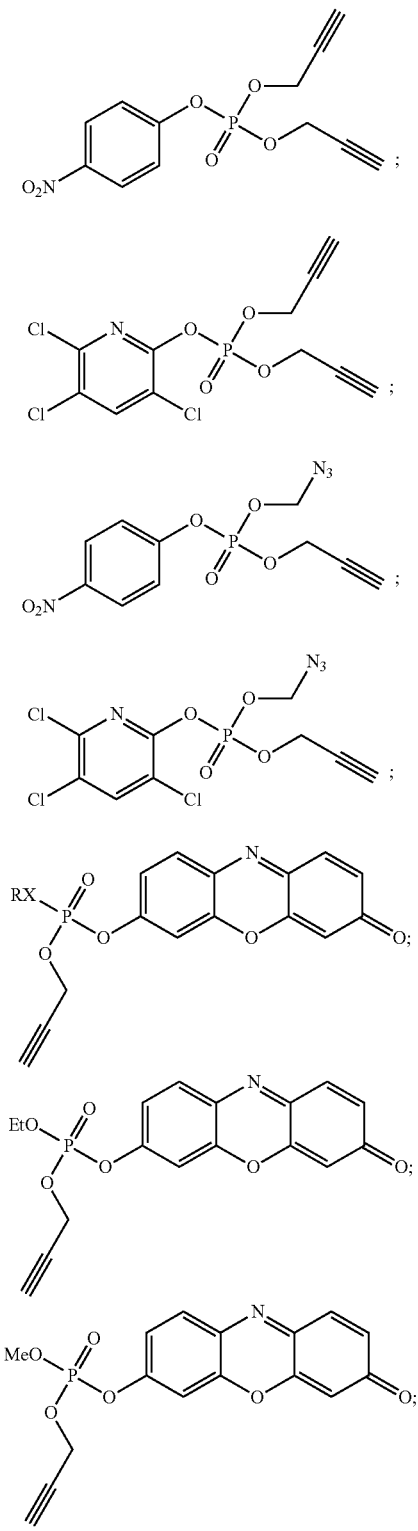

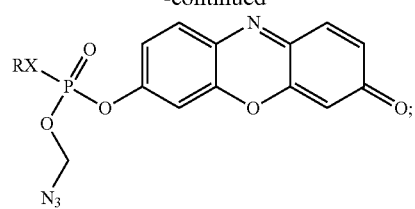
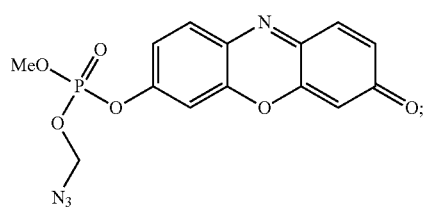
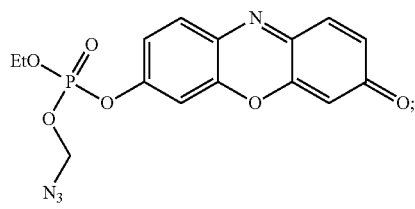
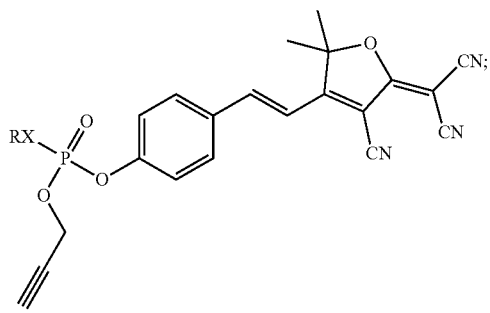
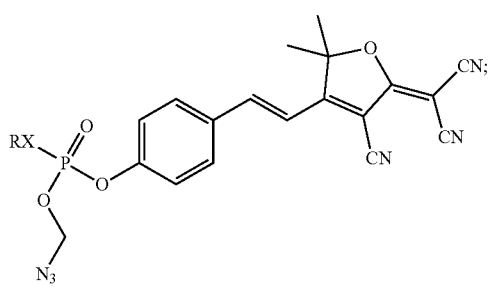
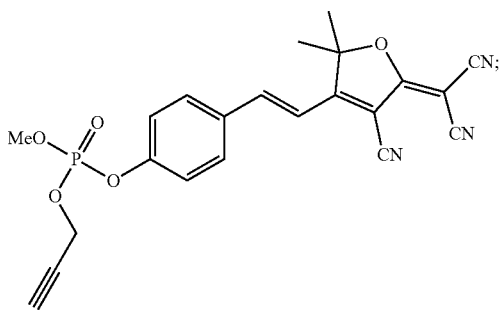
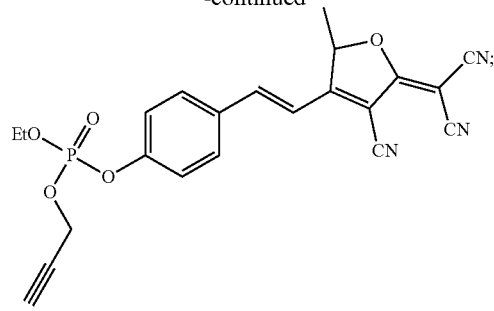
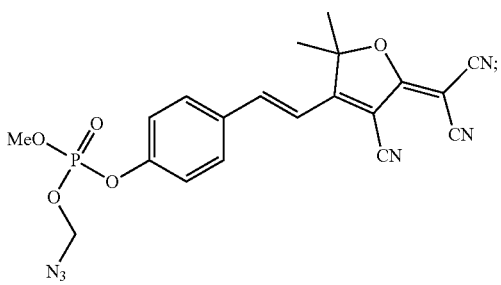
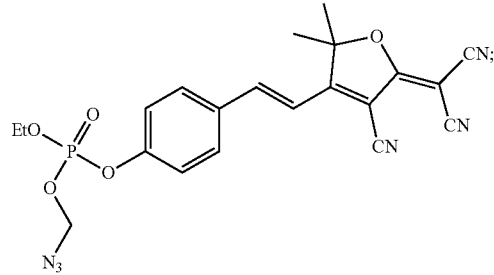
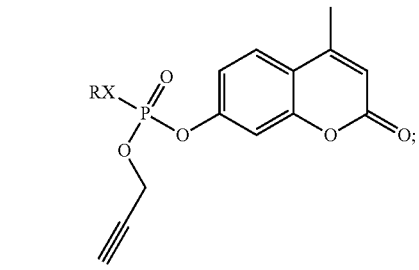
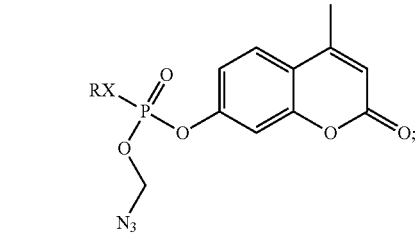
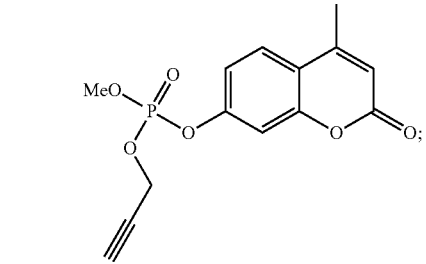

77
-continued
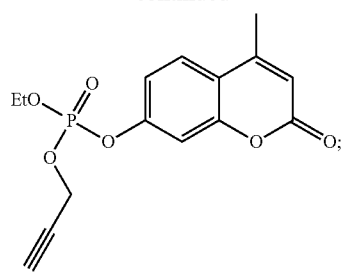
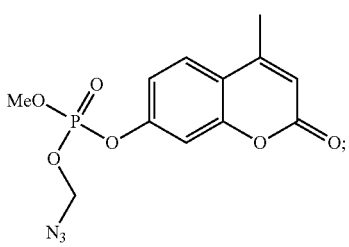
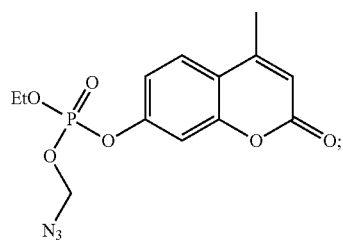
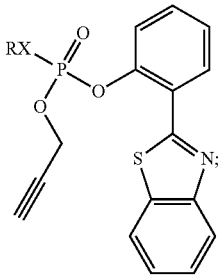 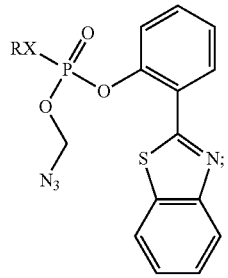
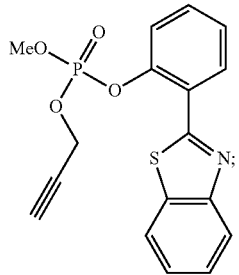 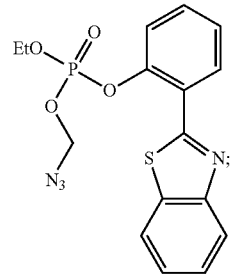
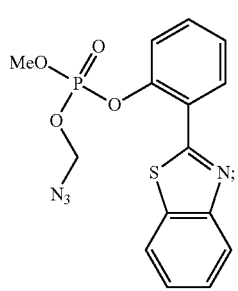 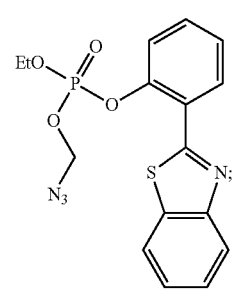
78
-continued
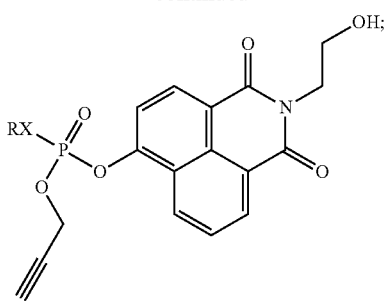
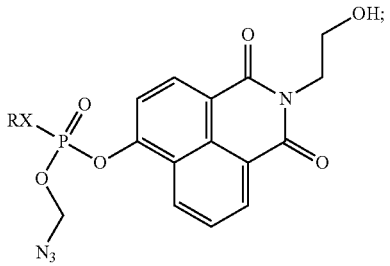
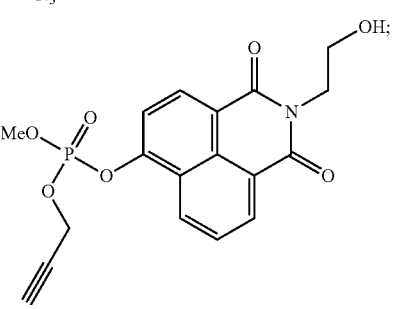
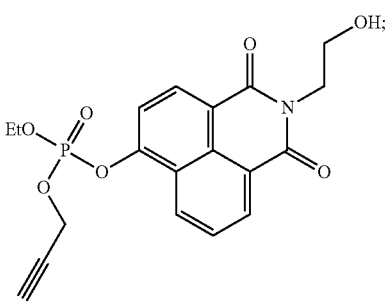
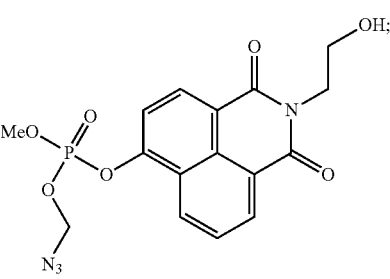
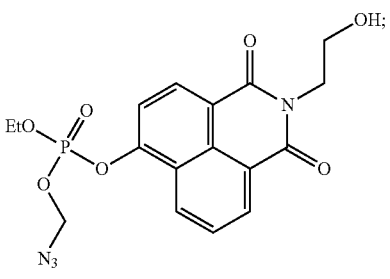

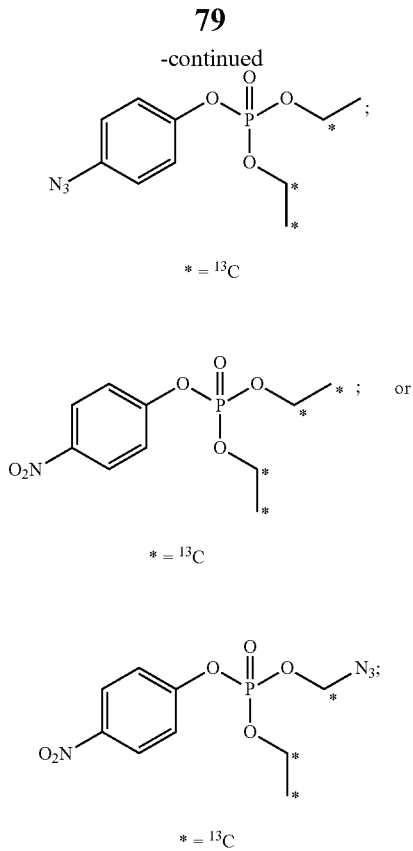

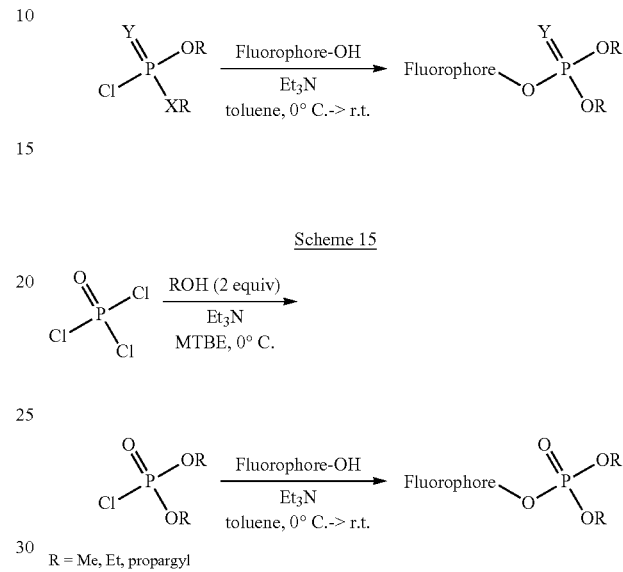

wherein X is —C(H)(OH)—, oxygen, or sulfur and R is a pesticide or toxin functional group as described above.

Probes described above can be made by functionalizing a phosphorus-containing starting compound. In some embodiments, the phosphorus-containing compound can be a phosphoryl trihalide, such as phosphoryl trichloride. The linker-anchor, and (linker)$_n$pTag (or (linker)$_n$Tag) groups can be introduced by exposing the phosphoryl trihalide to a base and a linker-anchor precursor and a (linker)$_n$pTag precursor (or a (linker)$_n$Tag precursor). Such precursors can comprise an —OH terminal group that is deprotonated by the base and then displaces a halide of the phosphoryl halide group. The XR group can be added under conditions sufficient to promote displacement of a halide of the phosphoryl halide by an XR group precursor. Such methods are recognized by those of ordinary skill in the art with the benefit of the present disclosure.

Representative methods of making certain probes are provided below in Schemes 14-17.

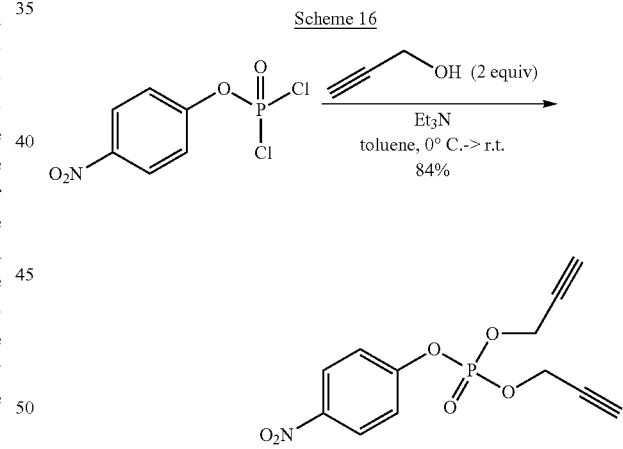

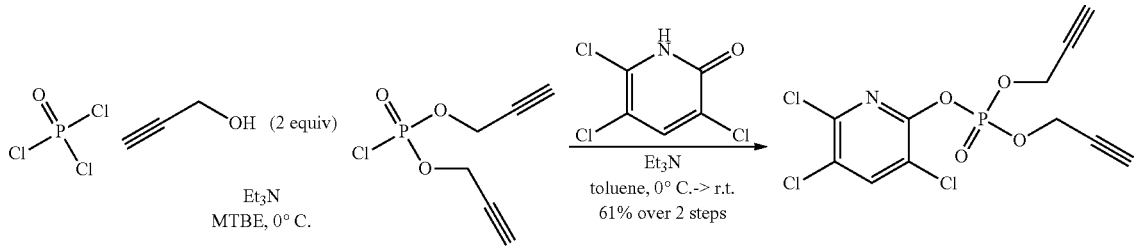

In yet additional embodiments, the probe can mimic an organophosphonate compound. Such probe embodiments comprise a phosphonate core structure (for example, that structurally mimics a particular organophosphonate toxin (for example, sarin, soman, agent VX, diisopropyl fluorophosphates, tabun, cyclosarin, GV, agent VR, cresyl saligenin phosphate, or the like) and further comprises a Tag or pTag moiety attached to the phosphonate core. In some embodiments, the probes can have a structure satisfying Formula XIII.

Formula XIII

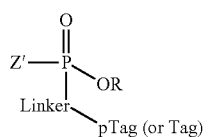

With reference to Formula XIII, the Z' group can be a halogen, a sulfur-containing heteroaliphatic group, a cyano group, or oxygen which is further bound to R when R is a benzyl group; R can be aliphatic or can be a benzyl group and in some embodiments, the benzyl group can further be bound to Z' when Z' is oxygen; the linker can be selected from an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; the pTag group, if present (such as when a Tag group is not used), comprises a clickable functional group; the Tag group, if present (such as when a pTag group is not used), comprises a detectable moiety, such as a chromogen, a fluorophore, a detectable isotopic moiety (for example, $^{13}CH_3$ or $^{13}CH_2{}^{13}CH_3$) or the like. In particular disclosed embodiments, the linker group is an alkylene oxide (such as PEG), aromatic, lower alkyl (such as —(CH$_2$)$_m$, wherein m is an integer selected from 1 to 10, such as 1 to 8, or 1 to 6, or 1 to 4, or 1 to 3) or a combination thereof and a pTag group is present and is alkyne or azide. In particular embodiments, the linker group is a PEG linker, a —CH$_2$Ph-O—CH$_2$-group, a —CH$_2$Ph-CH$_2$— group, or a —CH$_2$Ph(Me)-O—CH$_2$—.

Representative probe embodiments that can be used to mimic organophosphate compounds are illustrated below.

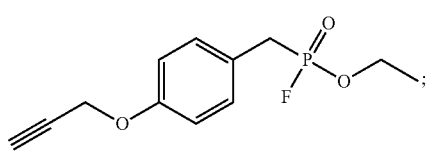

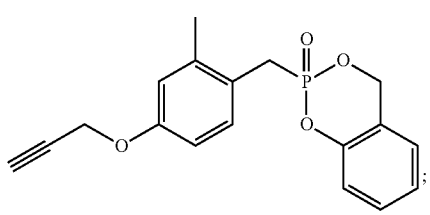

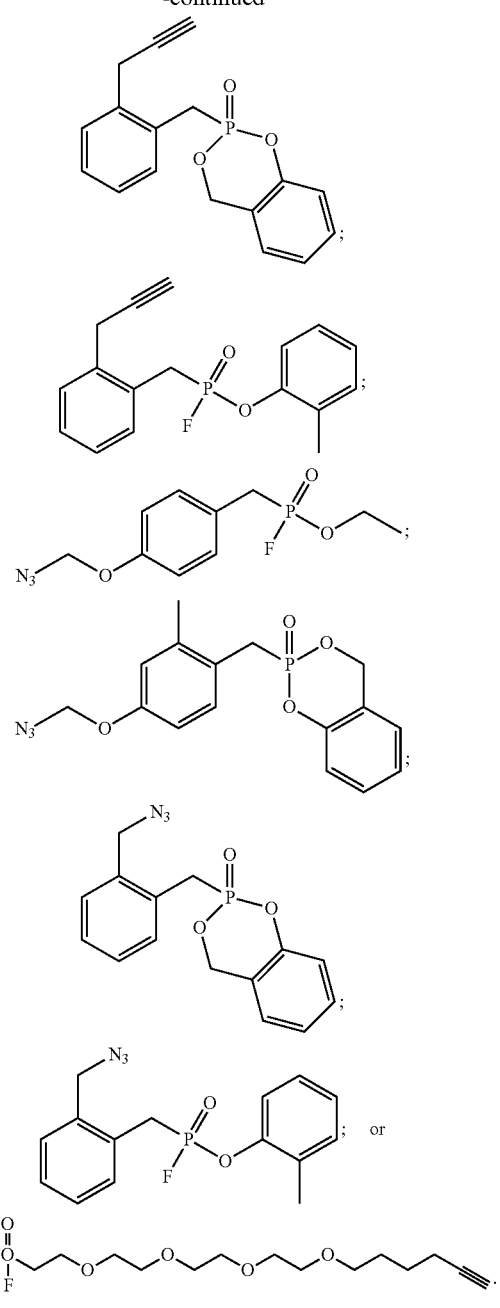

Organophosphonate probes can be made according to methods illustrated below in Schemes 18-20.

Scheme 18

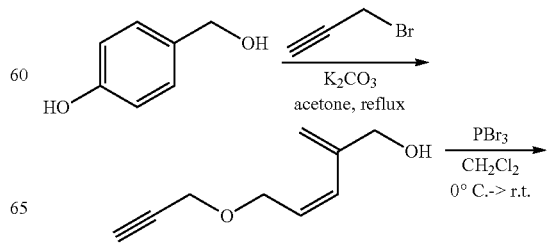

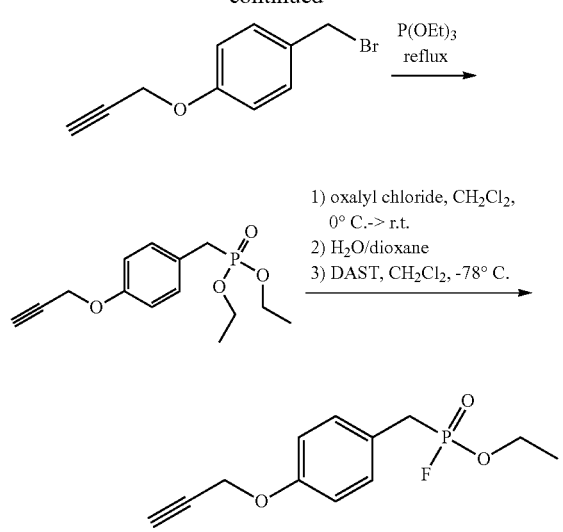
Scheme 19
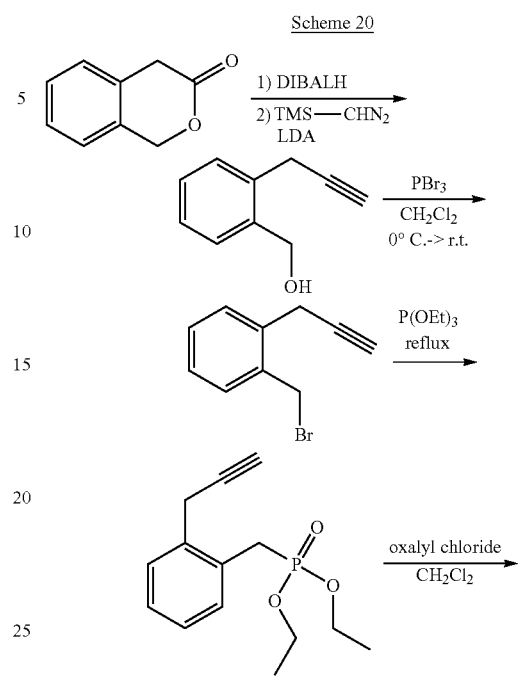
Scheme 20
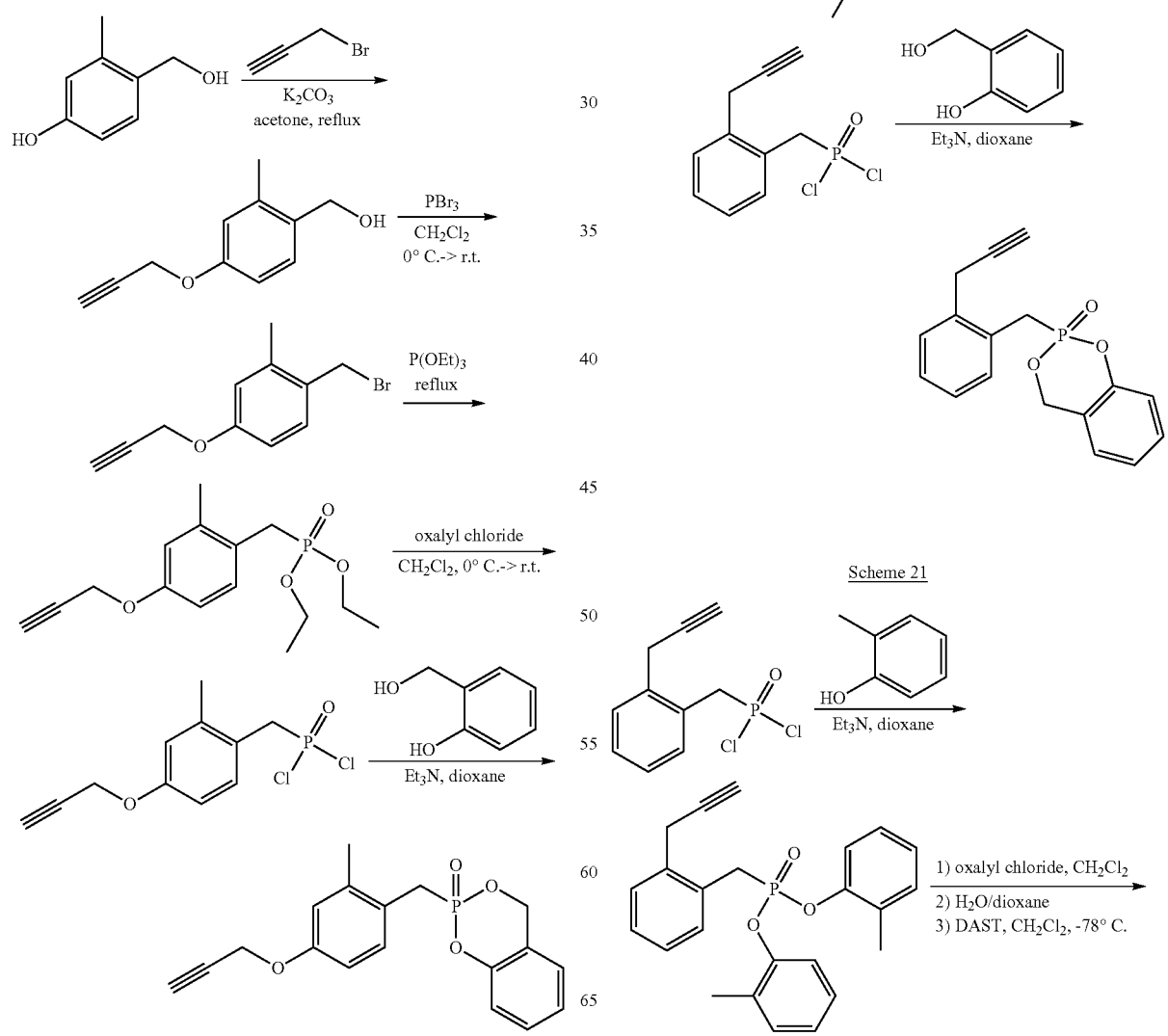
Scheme 21

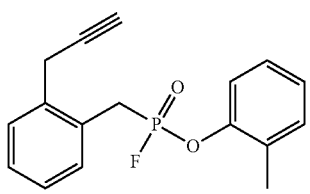
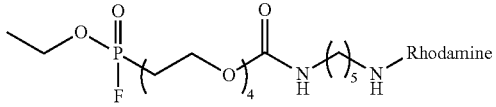

In independent embodiments of certain probe formulas described above, probes having the following structures are excluded from the specified genus; however, the probes illustrated below can be used in combination with substrates described herein to form devices and kits discussed below.

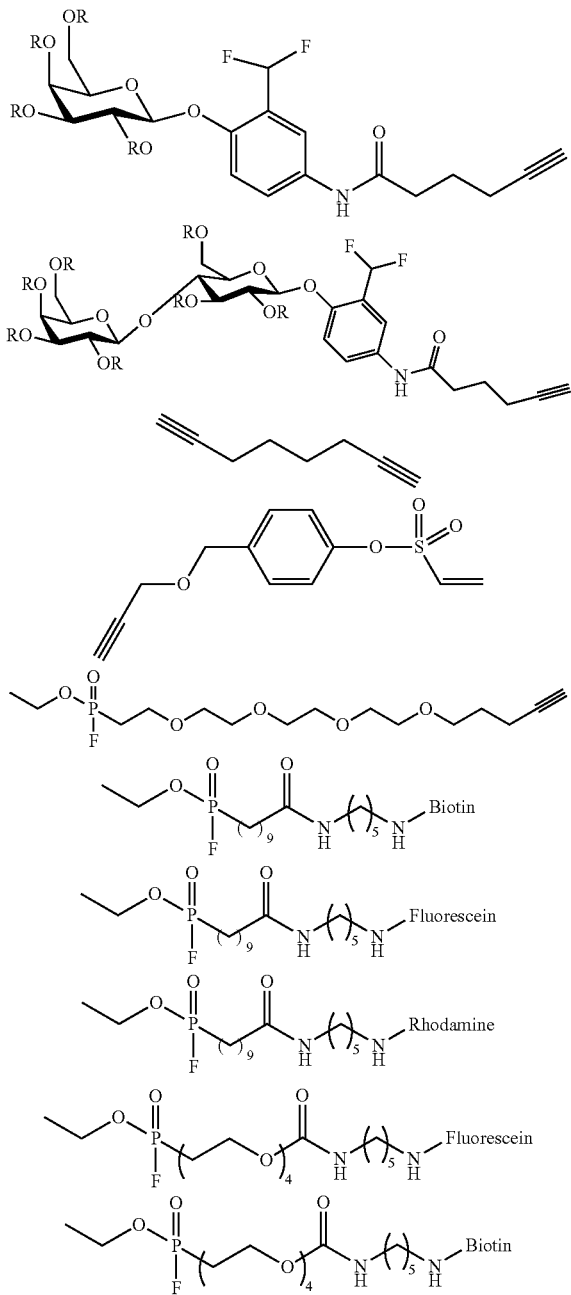

IV. KITS AND DEVICES

Probe embodiments described herein can be configured for use in a device and/or a kit that can be used to analyze soil microbiomes, aquatic microbiomes and other environments (including cellular environments). The device and kit can be used to assess and identify different species present in various environments and also to assess the functions/processes involving such species within the environment. In particular disclosed embodiments, the device can comprise one or more probe embodiments and a substrate, wherein the probe is (or a plurality of probes are) coupled to the substrate prior to exposure to a sample, or wherein the substrate and the probe are capable of being combined after exposure to a sample. The device and kit embodiments are configured to be mobile so that various areas of a field site where testing may occur can be accessed with ease. In additional embodiments, the device and kit embodiments can be used for benchtop analysis and can be used to analyze samples that have been extracted from a particular environment. Additionally, the device and kit embodiments are capable of multiple uses such that many samples can be analyzed with a single device or kit.

Conventional devices and measurements used to evaluate and characterize certain analytes, like microbes, suffer from setbacks, particularly limited sample size and physiological settings that are incompatible with chemical probing strategies. Device and kit embodiments disclosed herein address these fallbacks as they can be used to provide layers of functional resolution including the ability to demonstrate probe functionalization multiplexing. In particular embodiments, the device and kit embodiments can comprise fluorescent glass microsphere substrates that are (or can be) coupled with probe embodiments. Such embodiments provide the ability to multiplex the probe-functionalized microspheres in limited size samples to label target enzymes, and the ability to first quantify the amount of enzyme targets in a given sample using FACS, and subsequently identifying the specific targets and quantifying these targets using mass spectrometry-based proteomics.

In particular embodiments, the substrate component of the device is any suitable substrate that be exposed to an environmental or cellular sample, such as an air, soil, aquatic, a plant sample, or cellular sample, that can be contacted with soil, liquids, or cells extracted from such environments. In particular disclosed embodiments, the substrate is a substrate that can be inserted directly in the soil surrounding a plant or that can be inserted into a soil or liquid sample extracted from soil surrounding a plant. Representative substrates include, but are not limited to, glass-based substrates that can be functionalized with probe embodiments described herein such that the probe is coupled to functional groups present on the surface of the glass-based substrate. In some embodiments, glass plates, glass rods, and/or glass microspheres are used as the substrate component.

Figure 3:
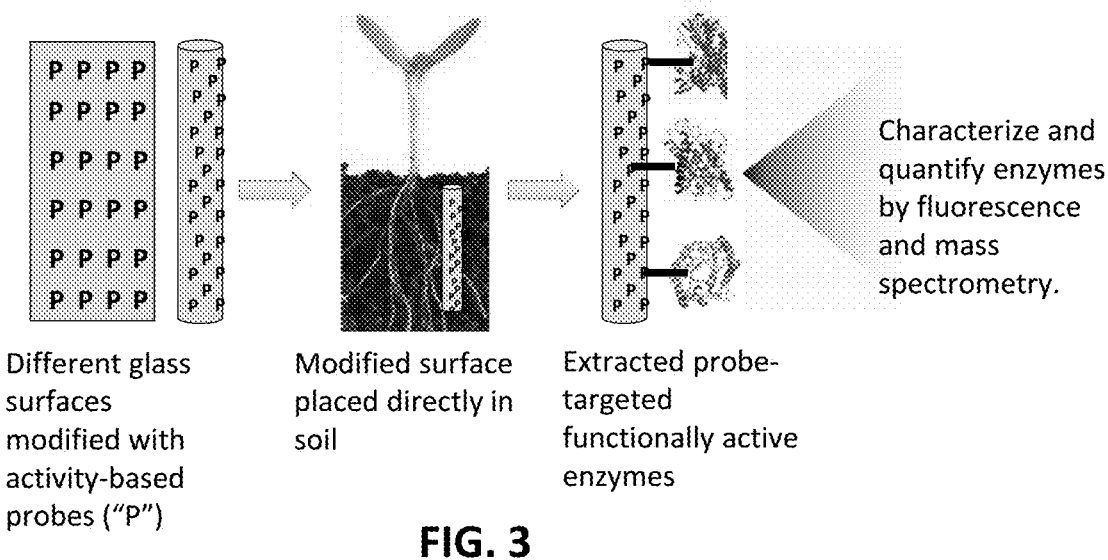
FIG. 3 shows an exemplary schematic of device embodiments disclosed herein comprising function-based probes for nutrient/toxin acquisition and analysis, for example with a soil sample.

In some embodiments, the device comprises a substrate in the form of a rod, plate, or microsphere that can be directly inserted in soil surrounding a plant and that can reach different depths of the soil to facilitate interaction between the probes coupled to the substrate and different species (for example, enzymes, microbes, or the like) present in the soil microbiome surrounding the plant. A schematic illustration is provided by FIG. 3. In additional embodiments, the device comprises a substrate suitable for laboratory analysis, such as a glass well-plate, a glass plate, or glass fluorescent microsphere (or a plurality thereof), wherein a soil and/or liquid sample is extracted from a particular environment and then exposed to the device.

The probes used in the device and/or kit can be selected from any probe embodiments disclosed herein. In some embodiments, the probes comprise or are modified to comprise a bi-functional linker group comprising an anchor group that is capable of anchoring the probe to a substrate component of the device. In particular disclosed embodiments, the anchor group is a clickable functional group that can be reacted with a clickable functional group present on the substrate surface using a click chemistry reaction to thereby covalently anchor the probe to the substrate. In some embodiments, the probe can be pre-coupled to the substrate prior to sample exposure using such techniques. In some additional embodiments, the probe can be post-coupled to the substrate using such techniques after the probe has been exposed to a sample. The pre-coupled or post-coupled probe further comprises a pTag group that is converted to a tag group during use of the device or, in some embodiments, the tag group can be pre-installed on the probe.

In some embodiments, the device is pre-assembled such that the probe embodiments are pre-coupled to the substrate and any additional reagents used in analyzing the soil (or other sample) are pre-contained within the device. In some other embodiments, the device may be provided as part of a kit that comprises a pre-assembled device and any additional reagents used to analyze the soil (or other sample) are provided as separate components of the kit (for example, such as in reagent bottles). These components of the kit can then be combined by the user prior to use. In yet some additional embodiments, the kit can comprise a substrate that can be treated with probe embodiments, which are provided by separate reagent bottles within the kit, using suitable coupling conditions to thereby couple any desired probe embodiments to the substrate to ready the apparatus for use.

Methods of making the device embodiments of the present disclosure are also disclosed. In some embodiments, the device can be made by exposing the substrate to a probe embodiment comprising an anchor group, such as a clickable functional group or other functional group capable of chemically binding to functional groups of the substrate. In embodiments where the probe comprises a clickable functional group, the substrate typically also comprise a clickable functional group on its surface that can react with the clickable functional group of the probe. In some embodiments, the substrate is a glass substrate comprising a surface having hydroxyl groups that can be modified with alkoxysilane molecules to provide a silanized substrate surface. In some embodiments, the silanized substrate surface can further be reacted with a reagent comprising a clickable functional group. In particular disclosed embodiments, the anchor group of the probe forms a covalent bond with functional groups of the substrate surface (for example, hydroxyl groups, alkoxysilane groups, clickable functional groups, or the like). Exemplary alkoxysilane molecules include, but are not limited to, aminosilanes (for example, (3-aminopropyl)-triethoxysilane, (3-aminopropyl)-diethoxy-methylsilane, (3-aminopropyl)-dimethyl-ethoxysilane, (3-aminopropyl)-trimethoxysilane, and the like), glycidoxysilanes (for example, 3-glycidoxypropyl)-dimethylethoxysilane and the like), and mercaptosilanes (for example, (3-mercaptopropyl)-trimethoxysilane, (3-mercaptopropyl)-methyl-dimethoxysilane, and the like). In some embodiments, these representative groups can be further chemically modified to convert one or more functional groups of the alkoxysilane to a functional group capable of coupling with the functional group of the probe. Solely by way of example, an amine group of an aminosilane can be converted to an azide or can be coupled to an azide-containing reagent to provide a clickable group capable of undergoing a click chemistry reaction with an anchor group present on a probe (such as a clickable alkyne). In particular disclosed embodiments, the anchor group of the probe can be selected from a functional group capable of coupling with one or more functional groups present on the silanized substrate surface. For example, the probe can comprise one or more alkyne (or azide) moieties, which can react with any azides (or alkynes) present on the silanized substrate surface; or one or more carboxylic acid groups, which can react with any amines present on the silanized substrate surfaces; or one or more nucleophilic functional groups that can react with any epoxides present on the silanized substrate surface; or one or more alkene moieties that can react with any thiols present on the silanized substrate surface. Additional probe anchor groups that can be coupled to hydroxyl groups present on the substrate surface and/or a silanized substrate surface will be recognized by those of ordinary skill in the art with the benefit of the present disclosure.

In a representative embodiment, a glass plate device is made by functionalizing a glass slide with an alkoxysilane reagent, such as triethoxysilaneamine. Then, a solution of a reagent comprising a clickable functional group, such as NHS-ester-PEG-azide, is added to the glass slide to functionalize the surface of the substrate with azide moieties. The functionalized glass slide is then either exposed to a probe embodiment prior to sample exposure or is exposed to a probe embodiment that has first been exposed to a sample. The probe comprises an anchor group, such as a clickable alkyne, that can react with the azide of the substate. The glass slide and the probe are exposed to reaction conditions that facilitate covalent coupling of the probe to the glass slide through a triazole formed between the alkyne group of the probe and the azide group of the substrate. In this embodiment, the reaction conditions include using DMSO as a solvent and CuI as a catalyst.

Figure 4:
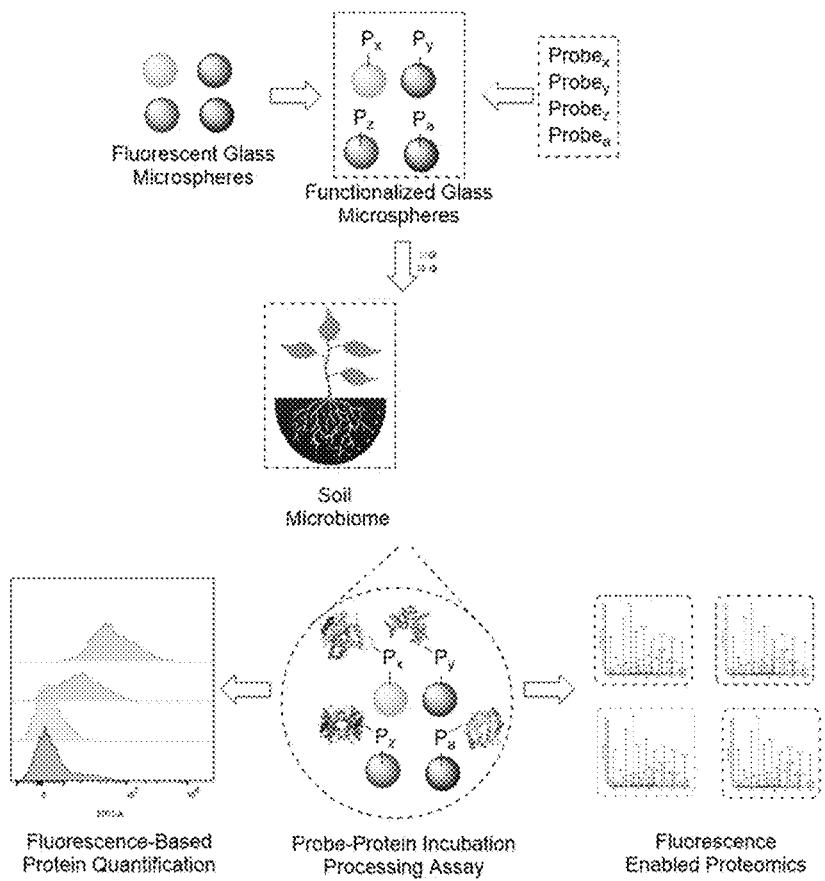
FIG. 4 shows an exemplary method using microspheres for multiplexed probing embodiments, wherein function-based probes ("P") are functionalized on fluorescent glass microspheres to enable flow cytometry, where each fluorophore is matched to a particular probe; the microspheres can be mixed and added to samples for multifunctional characterization of complex biological samples, such as soil microbiomes and after labeling, protein-probe-microspheres can be sorted further analysis (for example, determining the overall functional activity quantified based on their fluorescence emission and/or proteomics analysis of each sorted sample to yield identification of functionally active enzymes and their relative contribution to the overall functional activity).

In another example, probe embodiments can be coupled to fluorescent glass microspheres to provide a device for use in methods described herein. In such embodiments, a single probe embodiment can be coupled to a single microsphere. A plurality of microspheres can be made wherein each microsphere of the plurality is coupled to the same type of probe embodiment or wherein each microsphere of the plurality is coupled to different types of probe embodiments. Similar chemistry as described above can be used to couple the probe to the microsphere. Device embodiments comprising probes coupled to fluorescent glass microspheres enables the using various probes for several different enzyme targets in a single limited-size sample. Additionally, these device embodiments facilitate tandem direct quantification of target enzymes using Fluorescence-Activated Cell Sorting (FACS) and proteomics as depicted schematically in FIG. 4. In particular embodiments, the protein-probe-fluorescent microspheres are sorted and quantified by FACS. Then flow cytometry instruments can be used to provide quantitative fluorescence profiles, or full FACS systems can be used to sort by probe type and make subsequent proteomics measurements to enhance the measurement resolution.

In another representative example, a device comprising a well-plate having wells that are surface-modified with clickable functional groups (for example, azides) are exposed to probe embodiments that each comprise at least one anchor group (for example, an alkyne) that can react with the clickable functional group of the surface-modified wells to covalently attach the probe to an individual well. In some embodiments, a single well can comprise a plurality of probes covalently bound thereto. In some embodiments, different wells of the well-plate can be functionalized with different probe embodiments.

V. METHODS

Disclosed herein are embodiments of methods of using the disclosed probes and devices and/or kits comprising the probes. The probe and device/kit embodiments disclosed herein can be used to inform users about xenobiotic effects, metabolite recruitment, elemental sourcing (carbon, nitrogen, phosphorus, and sulfur), and other important functions involved in microbiomes, such as those in air, soil, water, plants, or cells. Because probes disclosed herein are designed to specifically interact with particular analyte targets in the presence of other analytes with which the probe does not interact, the probe embodiments to be used with certain device embodiments can be selected based on the particular type of analyte being targeted during use. Solely by way of example, a probe capable of interacting with a sulfatase can be used to determine whether there are any sulfatases present in a soil sample and further whether there is any deficiency or overabundance of the sulfatase species and/or whether the sulfatase species are not performing their proper function.

In some embodiments, the method comprises exposing a sample, such as a soil sample, a liquid sample (for example, form an aquatic source, such as a river, stream, ocean, lake, or tap), a plant sample, or a cellular sample to a probe embodiment described herein. Samples can be used directly, concentrated, or diluted. This step of the method can be carried out by using a device embodiment disclosed herein and exposing the device to the sample so that probes coupled to the substrate component of the device are in contact with the sample. In some embodiments, the device is contacted with soil or liquid from an area wherein a plant is planted or will be planted. In some embodiments, the contacting step can be an in situ contacting step whereby the device is inserted into soil in which a plant is planted such that the device is allowed to contact, or become positioned near, roots of the plant. The device can be inserted to any depth along the plant's root system. In some other embodiments, the contacting step can involve exposing the device to a sample, such as a soil or liquid sample, that has been extracted from a plant site. In such embodiments, the sample can be added to the device that comprises a substrate covalently coupled to probe embodiments, or the sample can first be combined with free probes that are then subsequently coupled to the substrate after forming a probe-analyte conjugate.

The sample typically is exposed to the probe embodiment(s) for a period of time that is sufficient to allow any analytes of interest that may be present in the sample to identify and interact with the probe embodiments. In some embodiments, the analyte of interest is allowed to interact with the probe such that it forms a covalent bond with the probe. In some embodiments, additional steps may be performed to facilitate binding the analyte to the probe, such as an energy exposure step whereby the sample and the probes are exposed to an energy source (for example, a light source, such as a light source that provides light at wavelengths ranging from 10 nm to 400 nm, or from 10 nm to 370 nm, or from 10 nm to 365 nm) that activates a functional group on the probe, which then forms a covalent bond with the analyte. For example, certain probe embodiments disclosed herein can comprise a diazirine or benzophenone functional group that can be activated by light to form a covalent bond with the analyte. In additional embodiments, the probe and the analyte can be exposed to conditions sufficient to facilitate analyte-based activation of a functional group on the probe whereby the functional group is converted to a reactive species that forms a covalent bond with the analyte. For example, certain probe embodiments disclosed herein can comprise an alkyne moiety and/or an isoxazolium moiety that can be activated by certain enzymes (for example, AMOs, LPMOs, and chitinases) to produce reactive species that bind with certain functional groups of the enzyme (for example, a carboxylic acid and/or a nucleophilic group of the enzyme).

In some embodiments, the method also can further comprise exposing the probe to conditions sufficient to convert any pTag moieties present on the probe to Tag moieties that can produce a detectable signal. In some such embodiments, the probe can be bound to an analyte of interest prior to converting the pTag moiety. Conditions suitable for converting the pTag group can include combining the probe with a reagent comprising a detectable moiety under click chemistry reaction conditions that promote forming a triazole moiety between the pTag moiety and a clickable functional group present on the detectable moiety of the reagent. This click chemistry based coupling covalently bonds the detectable moiety to provide a Tag group on the probe. In some embodiments, the Tag group can be a fluorophore or other visually-detectable moiety, such as a chromogen. In yet additional embodiments, the Tag group can be a moiety that facilitates enrichment of the analyte bound to the probe. A representative example of such a Tag group is biotin.

Once the Tag group is generated, probes bound to analytes can be detected, identified, and quantified using a suitable detection method, such as fluorescent detection in SDS-Page methods, affinity chromatography, tryptic digestion, mass spectrometry, flow cytometry, and any combinations thereof. In some embodiments, a plurality of different probe embodiments can be used and the user is able to then identify the particular analytes present in the soil based on signals generated during use. Solely by way of example, a soil sample can be exposed to a device comprising any combination of the probe embodiments disclosed herein and if any species capable of binding to or otherwise interacting with such probes are present in the soil sample, they will interact with the corresponding probe embodiment to form an conjugate which can then be visualized and/or enriched after modifying the conjugate to comprise a Tag group. For example, fluorescent Tag moieties provide a detectable signal that the user can use as confirmation that the soil sample contains an analyte species that has been bound to the probe. In some additional embodiments, the device can provide qualitative results that allow the user not only to determine the presence or absence of particular analytes within the soil microbiome, but also that allow the user to determine how much of a particular analyte is present. The user can then utilize the results obtained from analyzing the soil sample with the device to determine whether the soil should be treated or otherwise modified to promote plant productivity and health.

In some embodiments, methods of assaying for microbial protein function are described. In some embodiments, the methods include labeling at least one microbial protein (for example, a microbial enzyme, such as a glycoside hydrolase, for example, an endoglucanase, an exoglucanase, a β-glucosidase, a xylanase, a xylosidase, a glucuronidase, a mannanase, or an arabinosidase; a chitinase; a cellulase; a cellobiohydrolase; a xylanase; a heme or lignin peroxidase; a laccase; a nutrient metabolizing enzyme, such as carbon-, nitrogen-, sulfur-, or phosphorus-metabolizing enzymes [for example, sulfatases, proteases, glucosidases, or phosphatases]; hydrogenase; nitrogenase; isoprene or terpene synthase; ammonia monooxygenase; catechol dioxygenase; alkane hydroxylase; dioxygenase; peroxidase; glucosidases; vitamin b transporters or metabolizers, such as transporters or metabolizers of vitamin b1, b2, b3, b5, b7, b9, and b12; transporters, synthesizers, or metabolizers of amino acids, such as ala, arg, asn, asp, cys, gln, glu, gly, his, ile, leu, lys, met, phe, pro, ser, thr, trp, tyr, and val, for example, proteases [for example, serine or cysteine proteases], glutamine synthetase, glutamate synthase, and glutamate dehydrogenase for example, with a probe embodiment described herein. The at least one microbial protein can include at least one specific metabolic function (for example, bioprocessing, such as biofuel or bioenergy production, nutrient cycling, or bioremediation). Any protein can be labeled or targeted for labeling (for example, intracellular, extracellular, or transmembrane enzymes of proteins or proteins in which the at least one specific metabolic function is an enzymatic activity and/or metabolite uptake or sensing). In some examples, the method includes determining the presence of the at least one microbial protein in a sample (for example, a sample from a bioreactor, a cellular or plant, a soil, or an aqueous environment) by detecting a detectable signal produced by the probe attached to the microbial protein. In some examples, the methods can also include sorting or isolating the at least one microbial protein or microbes that include the at least one labeled microbial protein. In some examples, the methods further include identifying the microbes with the at least one labeled microbial protein.

Method embodiments of altering microbial metabolism in an environment are also described herein. In some examples, the methods include labeling at least one microbial protein, such as those described above. In some examples, the method further includes selecting an environment for alteration of the at least one specific metabolic function (for example, a bioreactor, a plant, a cellular, an air, a soil, or an aqueous environment). In some examples, the method includes altering the microbial metabolism in the environment, for example, by enriching the environment with the identified microbes, reducing the amount of the identified microbes in the environment, or increasing or reducing the at least one specific metabolic function.

Any of the method embodiments described herein can include performing genomic or proteomic assays using the at least one labeled microbial protein or microbes comprising the at least one labeled microbial protein. Any genomic assays can be used, including whole genome and/or whole exome sequencing (WGS and WES, respectively); sequencing for single nucleotide variants, insertions, and/or deletions (indels), copy number variations; RNA sequencing (for example, RNA-seq or whole transcriptome shotgun sequencing), such as 16S sequencing; assaying interactions between nucleic acids and ligands and/or macromolecules (for example, molecules typically with a mass of at least 2 kDa, such as nucleic acids with at least 10 nucleotides, polynucleotides, polypeptides, proteins, enzymes, and complexes with plurality of macromolecules); and metagenomics (for example, Sharma and Lal, *Indian J Microbiol*, 57(1):23-38, 2017, incorporated herein by reference). Genomics assays can include sequencing and sequence assembly and annotation, such as using de novo techniques, for example, shotgun sequencing or PCR, or next generation techniques (for example, "next gen" or high-throughput), for example, real-time single-molecule, ion torrent, pyro, synthesis, combinatorial probe anchor, ligation (for example, oligonucleotide ligation and detection or SOLiD), nanopore or Sanger sequencing; chromatin or cross-linking immunoprecipitation (for example, ChI and CLIP, respectively); and bioinformatics and computational biology. In some embodiments, performing genomic assays includes performing 16S sequencing and/or single cell genome sequencing.

Any proteomics assays can be used, including techniques for separating, identifying, and analyzing proteins (for example, analyzing intermolecular or intramolecular interactions, such as protein structure, protein-protein interactions, or protein-ligand interactions; Lee, *Trends Biotechnol.*, 19(6):217-22, 2001, incorporated herein by reference in its entirety). The proteomics assays can include using any tools available for proteomic analysis, for example, mass spectrometry (for example, using hard or soft ionization techniques, including matrix-assisted laser desorption/ionization or electrospray ionization, for example, with mass analyzers, such as time of flight, quadrupole filter, or ion trapping, as well as other techniques, such as liquid chromatography, capillary electrophoresis, tandem mass spectrometry, or fragmentation techniques, for example, collision-induced dissociation); electrophoresis (for example, 1D- or 2D-gel electrophoresis or western blotting), immunological assays (for example, immunological microarray assays or enzyme-linked immunosorbent assays, ELISAs), protein microarray assays (for example, functional protein or target protein array assays), chromatography (for example, affinity, size-exclusion, ion-exchange, or reverse-phase), tools for analyzing protein structure or electrochemistry (for example, x-ray crystallography or nuclear magnetic resonance), computational or bioinformatics tools (for example, protein identification, structure, or interaction modeling tools), or any combination thereof. In some embodiments, mass spectrometry (MS), such as liquid chromatography MS (LC-MS), and/or ELISA is used.

Any of the methods described herein can include labeling in any environment (for example, natural or artificial environments). Environments can vary relative to an organism and community and include, for example, a bioreactor, an air, a plant or cellular (for example, a plant endosphere or endophytic microbiome), a soil (for example, a plant rhizosphere or exophytic microbiome, agricultural fields, or marginal lands), or an aqueous environment. In some examples, the methods include labeling in the native habitat of microbes that include the at least one microbial protein (for example, a plant or cellular, a soil, or an aqueous environment). In some examples, the methods include labeling a microbial protein or microbe in which the microbe is uncultured.

Methods of bioprocessing related to microbial metabolism also are described herein. In some examples, the methods include labeling at least one microbial protein (for example, a glycoside hydrolase, for example, an endoglucanase, an exoglucanase, a β-glucosidase, a xylanase, a xylosidase, a glucuronidase, a mannanase, or an arabinosidase; a chitinase; cellulase; cellobiohydrolase; heme or lignin peroxidase; laccase; fatty acid synthases, such as synthases involved in acetyl-coA- or malonyl-coA-mediated fatty acid synthesis; nutrient metabolizing enzymes, such as carbon-, nitrogen-, sulfur-, or phosphorus-metabolizing enzymes, for example, sulfatases, proteases [such as serine or cysteine proteases], glucosidases, phosphatases; hydrogenase; nitrogenase; isoprene or terpene synthase; ammonia monooxygenase; catechol dioxygenase; alkane hydroxylase; dioxygenase; peroxidase; glucosidases; vitamin b transporters or metabolizers, such as transporters or metabolizers of vitamin b1, b2, b3, b5, b7, b9, and b12; transporters, synthesizers, or metabolizers of amino acids, such as ala, arg, asn, asp, cys, gln, glu, gly, his, ile, leu, lys, met, phe, pro, ser, thr, trp, tyr, and val, for example, glutamine synthetase, glutamate synthase, glutamate dehydrogenase), for example, with a probe embodiment described herein.

The methods described herein can include labeling in any environment (for example, natural or artificial environments). Environments can vary relative to an organism and community and include, for example, a bioreactor, an air, a plant or cellular (for example, a plant endosphere phyllosphere, or endophytic microbiome), a soil (for example, a plant rhizosphere or exophytic microbiome, agricultural fields, or marginal lands), or an aqueous environment. In some examples, the methods include labeling in the native habitat of microbes that include the at least one microbial protein (for example, a plant or cellular, a soil, or an aqueous environment). In some examples, the methods include labeling a microbial protein or microbe in which the microbe is uncultured.

The methods include any process that uses complete living cells or their components (for example, microbes, such as bacteria and fungi; cells, such as cells from plants, insects, birds, fish, reptiles, and mammals; proteins, such as enzymes (for example, enzymes involved in energy and/or product generation); and recombinant DNA; National Research Council (US) Committee on Bioprocess Engineering, *Putting Biotechnology to Work: Bioprocess Engineering*, Washington D.C., National Academies Press (US), 1992, incorporated by reference herein in its entirety) to obtain desired products. Bioprocessing applications vary and include the production of fuels and energy (for example, renewable and/or clean energy); agriculture and/or aquaculture (for example, damage control and nutrient production, such as microbes to reduce damage from temperature, pests, and chemicals, such as metals, or to enhance nutrient availability and/or uptake); and product manufacture (for example, chemicals, such as organic acids, oxygenated chemicals, fuel additives, and low-molecular-weight chemical and biological tools, such as biopharmaceutical tools; biopharmaceuticals, such as therapeutic proteins, polysaccharides, and antibiotics; food products, such as additives and processing aids; pesticides, such as biodegradable and environmentally compatible pesticides; fiber, such as from renewable sources; bioremediation or environmental-management aids, such as for controlling or remediating toxic wastes).

In some examples, bioprocessing can occur in a specific environment (for example, a bioprocessing environment). For example, bioprocessing can occur in a bioreactor (for example, any system, device, apparatus, or vessel in which processing, such as a chemical or biological process, involving biological substances or organisms, such as microbes, is carried out; Tapia et al., *Appl Microbiol Biotechnol,* 100: 2121-2132, 2016; Xie, *Front Bioeng Biotechnol,* 5:65, 2017; Sharma and Arya, Biotechnology Reports, 156:3-69, 2017, all of which are incorporated herein by reference in their entireties) or a plant or cellular (such as a plant endosphere, phyllosphere, or endophytic microbiome), air, soil (such as a plant rhizosphere or exophytic microbiome, agricultural fields, or marginal lands), or aqueous environment.

In some examples, the at least one microbial protein includes at least one specific metabolic function. Any protein can be labeled or targeted for labeling (for example, intracellular, extracellular, or transmembrane enzymes of proteins or proteins in which the at least one specific metabolic function is an enzymatic activity and/or metabolite uptake or sensing). In some examples, the methods include determining the presence of the at least one microbial protein in a sample (for example, a sample from a bioreactor; air; soil, such as a plant rhizosphere or exophytic microbiome; an aqueous environment; or a plant or cellular environment, such as a plant endosphere, phyllosphere, or endophytic microbiome).

In some examples, the methods include sorting or isolating microbes comprising the at least one labeled microbial protein or the at least one microbial protein. In some examples, the methods include identifying the microbes comprising the at least one labeled microbial protein. In some examples, the methods include selecting a bioprocessing environment (for example, a bioreactor, a soil, an aqueous, or a cellular or plant environment) for alteration of the at least one specific metabolic function (for example, fuel or energy production, bioremediation, or nutrient cycling). In some examples, the methods include altering microbial metabolism in the selected bioprocessing environment, for example, by enriching the selected bioprocessing environment with the identified microbes, reducing the amount of the identified microbes in the selected bioprocessing environment, or increasing or reducing the at least one specific metabolic function in the selected bioprocessing environment.

In some examples, the bioprocessing includes or the specific metabolic function is related to nutrient cycling (for example, carbon, nitrogen, sulfur, or phosphate cycling), bioremediation, or producing energy from biomass. In some embodiments, the specific microbial function is related to nutrient cycling (such as nutrient cycling under conditions of stress or environmental change, for example, in a soil or an aqueous environment, such as in response to stress or environmental change).

Nutrient cycling includes processes by which nutrients, such as carbon, nitrogen, phosphorus, and sulfur, are exchanged among different environments and ecosystems, such as biosphere, pedosphere, geosphere, hydrosphere, atmosphere, lithosphere, and terrestrial and marine ecosystems. In some examples, the nutrient cycling includes transport, synthesis, or metabolism of carbon, nitrogen, phosphorus, or sulfur. In some examples, proteins and enzymes (for example, microbial enzymes) or microbes with the protein or enzyme function (e.g., the labeled proteins, enzymes, or microbes) are used for nutrient cycling. In some examples, nutrient cycling includes nitrogen or carbon cycling, which can include glucosidases or proteases (for example, Almeida et al., *Glob. J. Agric. Res. Rev,* 3(2):146-150, 2015; Berges and Mulholland, Nitrogen in the Marine Environment, ch. 32, 1385-1444, 2008, incorporated by reference herein in their entireties) or proteins or enzymes that directly or indirectly interact with vitamin b (for example, for transport or metabolism of vitamin b1, b2, b3, b5, b7, b9, and b12; Bertrand and Allen, *Front Microbiol,* 3:375, 2012, incorporated herein by reference in its entirety); amino acids (for example, for transport, assimilation, or metabolism of amino acids, such as glutamine synthetase, glutamate synthase, glutamate dehydrogenase, or proteases, such as cysteine or serine proteases; Moe, *Am J Bot,* 100(9):1692-705, 2013; van Heeswijk et al., *Microbiol Mol Biol Rev,* 77(4):628-95, 2013; Mora, *Microbiol Rev,* 54(3):293-304, 1990, all of which are incorporated herein by reference in their entireties), including ala, arg, asn, asp, cys, gln, glu, gly, his, ile, leu, lys, met, phe, pro, ser, thr, trp, tyr, and val; sugars or starches (for example, metabolism of sugars and starches, such as xylanose, glucose, or cellobiose); lignins (for example, metabolism or transport of p-hydroxyphenyl, guaiacyl, and syringyl monomers); or chitin (for example, chitinases or lytic polysaccharide monooxygenases, LPMO). In some examples, nutrient cycling includes sulfur or phosphorus cycling, such as using sulfatases or phosphatases (for example, Nannipieri et al., Phosphorus in Action, Soil Biology, ch 9, 215-243, 2011; Kertesz, *FEMS Microbiology Reviews,* 24:135-175, 1999; Kertesz et al., *FEMS Microbiol Rev,* 24(2):135-75, 2000; Korstee et al., Biochemistry (Mosc), 65(3):332-40, 2000, incorporated herein by reference in their entireties).

In some examples, the nutrient cycling proteins, enzymes, or microbes are labeled, such as with a probe embodiment described herein. In some embodiments, nutrient cycling proteins, enzymes, or microbes are labeled with at least one of the probes described by Formulas I, IA, II, IIA, IIB, III, IIIA, IIIB, IIIC, IV, V, VI, VII, VIII, IX, X, or XI (such as at least 1, 2, 3, 4, 5, 6, 7, 8, 9, 10, 11, 12, 13, 14, 15, or 16 of the probes described by Formulas I, IA, II, IIA, IIB, III, IIIA, IIIB, IIIC, IV, V, VI, VII, VIII, IX, X, or XI).

In some examples, plants experience stress when they are not growing under ideal conditions, including access to ideal nutrient levels, water levels, temperature, microbes, or light levels or upon exposure to pests (for example, a living organism that occurs where it is not wanted or that causes damage to plants, animals, or ecosystems), pathogens (for example, any organism that can produce disease), or pollutants (for example, contaminants, such as a substance or energy, including light or radiation, that causes adverse, undesired, harmful, or poisonous effects). In some examples, microbes associated with plants can affect plant stress, such as increase or decrease plant stress, for example, depending on the stress (for example, change in $CO_2$ level, temperature, or water level) or microbe (for example, bacteria, fungi, or algae, such as microbes that interact with plants and inhabit the plant or surrounding soil). In some examples, the methods include predicting a response to stress or environmental change, such as plant's response to stress or environmental change (for example, a response to stress or environmental change related to nutrient cycling, such as transport, synthesis, or metabolism of carbon, nitrogen, phosphorus, or sulfur), for example, based on the identified microbes or microbial proteins or enzymes, such as using at least one probe embodiment described herein (e.g., at least one of the probes described by Formulas I, IA, II, IIA, IIB, III, IIIA, IIIB, IIIC, IV, V, VI, VII, VIII, IX, X, or XI, such as at least 1, 2, 3, 4, 5, 6, 7, 8, 9, 10, 11, 12, 13, 14, 15, or 16 of the probes described by Formulas I, IA, II, IIA, IIB, III, IIIA, IIIB, IIIC, IV, V, VI, VII, VIII, IX, X, or XI).

In some embodiments, the bioprocessing includes or the specific metabolic function is related to bioremediation, such as treating a contaminated environment or media (for example, an aqueous or soil environment, such as agricultural fields, or marginal lands). In some examples, bioremediation includes processes for treating a contaminated environment or media (for example, water, soil, subsurface material, or air). In some examples, bioremediation includes supporting, stimulating, or initiating microbe growth or habitation of a contaminated environment or media, for example, to treat waste (for example, wastewater, industrial waste, or solid waste) or degrade pollutants or contaminants (for example, reduced pollutants, such as hydrocarbon, phenol, aliphatic, alicyclic, or aromatic compounds; oxidized pollutants, such as chlorine-containing compounds, energetics or explosives, or nitrates; or heavy metals).

In some examples, bioremediation includes treating a contaminated environment or media using proteins, enzymes, or microbes (e.g., proteins, enzymes, or microbes labeled using the methods disclosed herein) with at least one specific metabolic function, such as at least one specific metabolic function of enzymes, proteins, or microbes (for example, microbial enzymes or proteins or microbes expressing at least one enzyme or protein). In some embodiments, the contamination includes an organophosphate, an organophosphonate, a polycyclic hydrocarbon or petroleum hydrocarbon (for example, benzene, toluene, ethyl benzene, or xylene); an alkane hydrocarbon (for example, methane, ethane, propane, butane, pentane, hexane, heptane, octane, nonane, decane, undecane, dodecane, tridecane, tetradecane, pentadecane, hexadecane, heptadecane, octadecane, nonadecane, or eicosane); or a chlorohydrocarbon (for example, chlorinated hydrocarbons, such as methyl chloride, methylene chloride, chloroform, ethyl chloride, or methylchloroform). In some embodiments, the at least one protein or enzyme (for example, a protein or enzyme, such as a microbial enzyme, labeled using the methods and probe embodiments disclosed herein) is ammonia monooxygenase, catechol dioxygenase, alkane hydroxylase, dioxygenase, or peroxidase. In some examples, the at least one contaminant is an organophosphate, an organophosphonate, an aromatic hydrocarbon, an alkane hydrocarbon, or a chlorohydrocarbon. In some examples, the methods include for example, labeling proteins, enzymes, or microbes using at least one probe embodiment described herein (e.g., at least one of the probes described by Formulas VII or VIII, such as at least 1 or 2 of the probes described by Formulas VII or VIII).

In some examples, the bioprocessing includes, or the specific metabolic function is related to, producing biofuel or bioenergy, such as producing energy from biomass (for example, an organic substance that can be used to obtain energy, for example, biofuel; Liao et al., *Nat Rev Microbiol,* 14(5):288-304, 2016, incorporated by reference herein in its entirety), including matter from any living organism, including plants, animals, or microbes, such as algae; examples of biomass include direct sources, such as plants and algae, and indirect sources, such as waste from living organisms, for example, biomass from arable crops or products thereof (for example, sugarcane, corn, soybean, canola, or sugar, starch, or oil derived therefrom), lignocellulosic or woody biomass (for example, plant dry matter, such as plant matter with lignins, cellulose, and/or hemicellulose, for example, from terrestrial plants, including trees, such as poplar trees, bushes, and grass, such as switch grass and elephant grass, or agricultural waste or byproducts, including from corn, sugarcane, straw, and forestry), agricultural residues (for example, field and process residues, such as stalks, stems, leaves, seed pods, husks, seeds, molasses, roots, and bagasse), or plant, animal, or microbial waste (e.g., chitin), or products therefrom).

In some embodiments, proteins and enzymes (for example, microbial enzymes) or microbes with the protein or enzyme function that are used for biofuel or bioenergy production are labeled using the methods described herein, for example, glycoside hydrolases, for example, endoglucanases, exoglucanases, β-glucosidases, xylanases, xylosidases, glucuronidases, mannanases, or arabinosidases; chitinases; LPMOs; cellulase; cellobiohydrolase; xylanases; heme or lignin peroxidases; laccases; fatty acid synthases, such as synthases involved in acetyl-coA- or malonyl-coA-mediated fatty acid synthesis; nutrient metabolizing enzymes, such as carbon-, nitrogen-, sulfur-, or phosphorus-metabolizing enzymes, for example, sulfatases, proteases (such as serine or cysteine proteases), glucosidases, phosphatases; hydrogenase; nitrogenase; or isoprene or terpene synthase, such as using a probe embodiment described herein. In some examples, the identified microbe can include *Streptomyces viridosporus*. In some embodiments, the proteins, enzymes, or microbes are labeled using at least one probe embodiment described herein (e.g., at least one of the probes described by Formulas I, IA, II, IIA, IIB, III, IIIA, IIIB, IIIC, IV, V, VI, VII, VIII, IX, X, or XI, such as at least 1, 2, 3, 4, 5, 6, 7, 8, 9, 10, 11, 12, 13, 14, 15, or 16 of the probes described by Formulas I, IA, II, IIA, IIB, III, IIIA, IIIB, IIIC, IV, V, VI, VII, VIII, IX, X, or XI).

In some examples, producing biofuel or bioenergy includes processes for producing energy or fuel derived (for example, directly, such as from plants or algae, or indirectly, such as from plant waste or byproducts, for example, from agricultural, commercial, domestic, or industrial use; Meadows et al., *Biotechnol J*, 13(1), 1-13, 2018; Jiang et al., *Bioresour Bioprocess*, 4(1):11, 2017, both of which are incorporated by reference herein in their entireties) from biological processes, such as agriculture or anaerobic digestion. Biofuel can be non-renewable or renewable (for example, biofuel derived from photosynthetic processes, such as in algae or plants, or conversion of biomass into usable energy, such as thermal, chemical, and biochemical conversion). Any form of biofuel is included, such as biofuel in liquid, gas, or solid form, for example, first generation (for example, biofuel derived from food crops or crops grown on arable land), second generation (for example, biofuel derived from biomass), third generation (for example, biofuel derived from algae or algae products), or fourth generation biofuels (for example, biofuels derived using non-arable land, such as electrofuels, photobiological solar fuels, and carbon-neutral fuels, for example, using transesterification).

The methods described herein can include performing genomic or proteomic assays using the at least one labeled microbial protein or microbes comprising the at least one labeled microbial protein. Any genomic assays can be used, including whole genome and/or whole exome sequencing (WGS and WES, respectively); sequencing for single nucleotide variants, insertions, and/or deletions (indels), copy number variations; RNA sequencing (for example, RNA-seq or whole transcriptome shotgun sequencing), such as 16S sequencing; assaying interactions between nucleic acids and ligands and/or macromolecules (for example, molecules typically with a mass of at least 2 kDa, such as nucleic acids with at least 10 nucleotides, polynucleotides, polypeptides, proteins, enzymes, and complexes with plurality of macromolecules); and metagenomics (for example, Sharma and Lal, *Indian J Microbiol*, 57(1):23-38, 2017, incorporated herein by reference). Genomics assays can include sequencing and sequence assembly and annotation, such as using de novo techniques, for example, shotgun sequencing or PCR, or next generation techniques (for example, "next gen" or high-throughput), for example, real-time single-molecule, ion torrent, pyro, synthesis, combinatorial probe anchor, ligation (for example, oligonucleotide ligation and detection or SOLiD), nanopore or Sanger sequencing; chromatin or cross-linking immunoprecipitation (for example, ChI and CLIP, respectively); and bioinformatics and computational biology. In some embodiments, performing genomic assays includes performing 16S sequencing and/or single cell genome sequencing.

The methods can include using any proteomics assays, for example, techniques for separating, identifying, and analyzing proteins (for example, analyzing intermolecular or intramolecular interactions, such as protein structure, protein-protein interactions, or protein-ligand interactions; Lee, *Trends Biotechnol.*, 19(6):217-22, 2001, incorporated herein by reference in its entirety). The proteomics assays can include using any tools available for proteomic analysis, for example, mass spectrometry (for example, using hard or soft ionization techniques, including matrix-assisted laser desorption/ionization or electrospray ionization, for example, with mass analyzers, such as time of flight, quadrupole filter, or ion trapping, as well as other techniques, such as liquid chromatography, capillary electrophoresis, tandem mass spectrometry, or fragmentation techniques, for example, collision-induced dissociation); electrophoresis (for example, 1D- or 2D-gel electrophoresis or western blotting), immunological assays (for example, immunological microarray assays or enzyme-linked immunosorbent assays, ELISAs), protein microarray assays (for example, functional protein or target protein array assays), chromatography (for example, affinity, size-exclusion, ion-exchange, or reverse-phase), tools for analyzing protein structure or electrochemistry (for example, x-ray crystallography or nuclear magnetic resonance), computational or bioinformatics tools (for example, protein identification, structure, or interaction modeling tools), or any combination thereof. In some embodiments, mass spectrometry (MS), such as liquid chromatography MS (LC-MS), and/or ELISA is used.

VI. EXAMPLES

Example 1

In this example, a representative device embodiment was made using the following steps. Fisherbrand microscope slides were cleaned by submerging the slides in ~100 mL of 20% nitric acid at 85 C for 2 hours. Slides were then removed and placed in a beaker full of milliQ $H_2O$. After soaking for 1 minute, slides were moved to a new beaker of milliQ $H_2O$ and allowed to sit for 5 mins. Slides were then transferred to a 35% $H_2O_2$ solution at 75 C for 1 hour. Slides were then removed and placed in a beaker full of milliQ $H_2O$. After soaking for 1 minute, slides were moved to a new beaker of milliQ $H_2O$ and allowed to sit for 5 mins. Slides were moved to a beaker of methanol and allowed to sit for 5 mins. Slides were dried in 110 C oven for 1 hour (at least). A well cover was wetted with milliQ and attached to the surface of the slide. The well-attached slide was then placed back in the oven for 30 minutes to allow for drying. The device was tested for leaks by adding 1.6 mL milliQ to the surface. If no leaks are present after 10 minutes, discard the milliQ $H_2O$, place back in oven for ~15 mins, and proceed directly to functionalization. Each slide was functionalized with 32 uL of triethoxysilaneamine in 1.568 mL (1.6 mL total) of a 3:1 milliQ:MeOH solution at pH ~=4.5 (with acetic acid) overnight with rocking at r.t. The slide was washed with DMSO 2×, ethanol 2×, then placed in the oven for 1 hour. A solution of 5 mg NHS-ester-PEG-azide in 1.5 mL DMSO+100 uL TEA was added to the slide and allowed to rock overnight at r.t. The slide was washed with DMSO 3×. Click chemistry was performed for an individual slide with 1.6 mL total volume with DMSO as the solvent, 100 uM probe (FP2-ABP), and 20 uM CuI. The reaction was allowed to proceed overnight with rocking at r.t. The slide was washed with DMSO 3×.

Example 2

In this example, a representative device was used to analyze a sample. In particular, the device (such as the functionalized substrate from Example 1 above) was washed 2× with an aqueous solution containing the biological sample (for example, PBS). The sample was applied to the functionalized device surface for 3 hours with rocking (r.t. or desired temperature). The slide was washed 1× with PBS. Then, the slide washed 1× with 4% SDS with rocking at r.t. (5 mins). Then, the slide was washed 2× with DMSO (5 mins, then 30 mins with rocking). Next, the slide washed 1× with PBS, followed by washing 2× with PBS with 0.5% BSA with rocking at r.t. (first wash for 5 mins, second wash for 30 mins). Then the slide was washed 2× with 4% SDS with rocking at r.t. (first wash for 5 mins, second wash o/n). Then the slide was washed 1× with PBS, 1× with milliQ. Then the slide was washed with 6M urea with rocking at r.t. (1 hour). Then the slide was washed 2× with 1M NaCl 2× (1 min each). Then the slide was washed 2× with milliQ (1 min each). Then the slide was washed 1× with 2.5 mM NH4HCO3 (pH 8) (5 mins with rocking). Next, 1.59 mL 2.5 mM NH4HCO3 (pH 8) was added to each well. Dilute 20 ug trypsin (in vial) with 100 uL 2.5 mM NH4HCO3 (pH 8) was prepared and 10 uL trypsin solution (0.2 ug/uL) was added to each well surface (total 2 ug). The device was allowed to rock at r.t. overnight. The sample was collected and put in eppendorf tube. The sample was frozen and lyophilized and then resuspend in 50 uL 2.5 mM NH4HCO3 (pH 8). 10 uL was used for Quant-IT assay to determine protein concentration. Also, 40 uL of sample was transferred into glass ultracentrifuge tubes, which were spun down at 53,000 rpm in the TLA 120.1 rotor for 20 min. 25 uL of supernatant was collected and transferred into MS vial inserts for analysis.

Example 3

In this example, glass microspheres are used to provide a multiplexing device. To solution of lysate or pure protein (50 uL, typically 1 mg/mL) in Eppendorf tubes (1.5 mL best), is added bifunctional probe (100 uM) and incubated at 37° C. for 1 h with no agitation. To this solution is added DBCO-Rhodamine545 (100 uM) and incubated at 37° C. for 1 h with 500 rpm agitation. Washing with cold (−20° C.) MeOH (500-1000 uL) and centrifugation at 16×g for 2 m at 4° C. are performed. Supernatant (will be bright pink, based on fluorophore used) is removed and repeat these three steps are repeated two times. Walls of the Eppendorf may be pink, this is normal. The sample is allowed to dry. Then, 5-10% suspension of functionalized azide microspheres in MeOH are added to protein-containing Eppendorfs. MS is pipetted into the bottom of the tubes and allow to dry completely (~30 m, depending on volume). 100 uL 0.4% BSA in PBS is added back, microspheres are resuspended by sonication, and then vortexing and manual agitation (tapping bottom of tube on the benchtop works well) are performed. After resuspending microspheres, click chemistry conditions (per 50 uL, NaAsc 250 mm, 0.5 uL, THPTA 200 mm, 0.25 uL, CuSO4 100 mm, 1 uL) are used and the samples are allowed to incubate at 37° C. for 1 h with 1500 rpm agitation. Microspheres at this stage are washed (only really need 0.4% BSA with PBS 2×) and used for fluorescence based readings. Once complete, samples are washed as follows: 1×0.4% BSA in PBS, 4% SDS in PBS, 6M Urea, 2M NaCl, then return to volume (100 uL) 25 mM NH4HCO3, pH 8. The samples can be prepared for proteomics with fresh trypsin (1 ng/uL), incubate 12-24h at 37° C. no agitation. BCA can be performed to determine protein amount before preparing mass-spec samples.

Example 4

Figure 5:
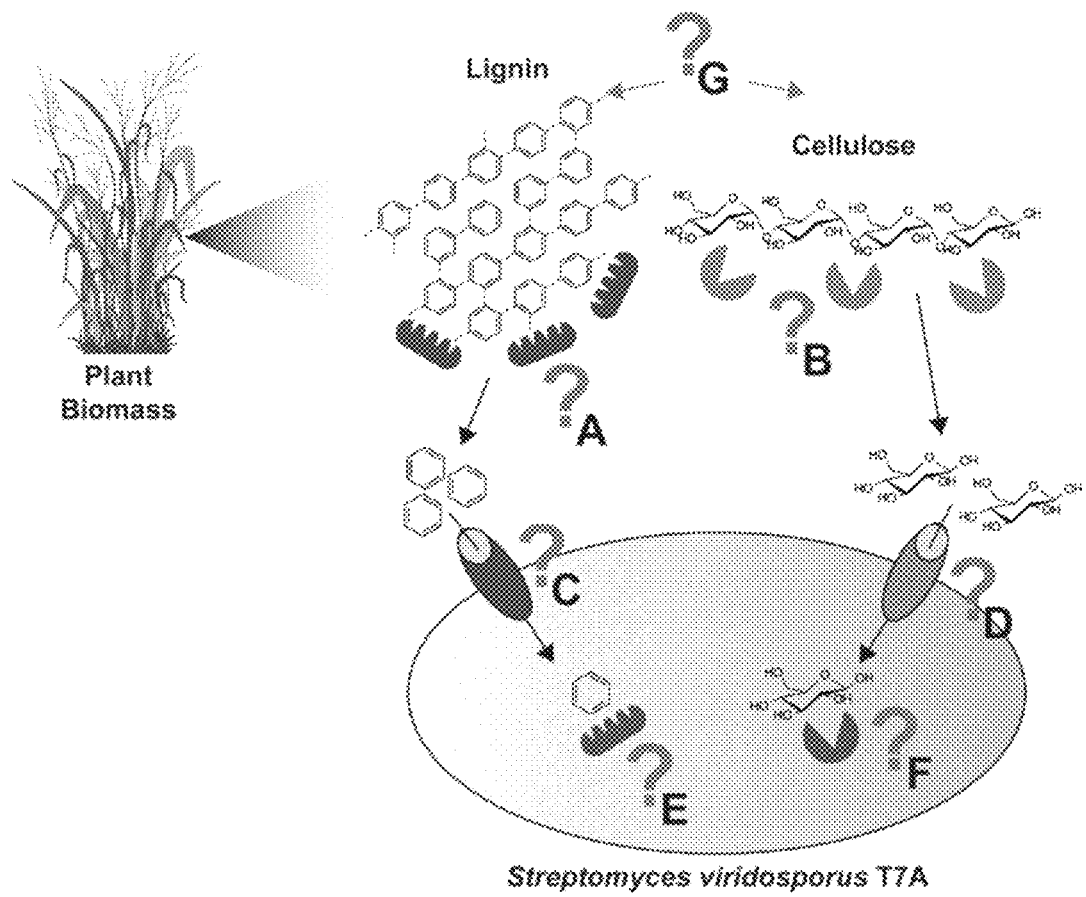
FIG. 5 shows a schematic illustration of the lignocellulose deconstruction, catabolite transport, and intracellular metabolic activities in *Streptomyces viridosporus* T7A, which can be evaluated with probe embodiments described herein; wherein extracellular oxidative lignin depolymerizing enzymes are involved in step A; cellulose degrading enzymes are involved in step B; step C represents the transport mechanisms for aromatic catabolites; step D represents the transport mechanism for carbohydrate catabolites; step E represents the intracellular metabolic activities associated with aromatic catabolites; step F represents the intracellular metabolic activities of carbohydrate catabolites; and the associations between lignin depolymerization and cellulose degradation are represented by step G.

In this example, the in vivo function-based protein profiling of the actinomycete, Streptomyces viridosporus T7A is evaluated to provide a complete understanding of microbial lignocellulose deconstruction by characterizing the interplay between lignin and cellulose degradation, and by evaluating the individual protein activities occurring throughout extracellular catabolic processes all the way to lignocellulosic catabolite transport and intracellular metabolism. As illustrated in FIG. 5, this example involves elucidating and annotating the concert of lignocellulose deconstruction, catabolite transport, and intracellular metabolic activities in S. viridosporus T7A. S. viridosporus is grown in liquid culture, consistent with industrial refinery/fermentation platforms. Liquid culture generally does not lead to sporulation; instead, growth first involves a young, compartmentalized mycelium (MI) followed by differentiation into a multinucleated second mycelium (MII).

The following are characterized: extracellular oxidative lignin depolymerizing enzymes (step A in FIG. 5) and cellulose degrading enzymes (step B in FIG. 5), the transport mechanisms for aromatic (step C in FIG. 5) and carbohydrate (step D in FIG. 5) catabolites, and the intracellular metabolic activities associated with aromatic (step E in FIG. 5) and carbohydrate (step F in FIG. 5) catabolites. Associations (step G in FIG. 5) between lignin depolymerization and cellulose degradation also are evaluated by growing S. viridosporus on various lignocellulosic plant biomass substrates, and the alterations to the functional associations are compared in compartmentalized mycelium (MI) versus multinucleated second mycelium (MII) growth phases. With reference to FIG. 5, the pill and "Pac-Man" shapes indicate proteins and enzymes.

To functionally study S. viridosporus, function-based probe embodiments described herein are used for proteomics, imaging, and cell sorting. For example, probes for glycoside hydrolases and lignin peroxidases are used, and probes that mimic lignocellulosic catabolites (such as the cellobiose or β-aryl ether-based probe embodiments described herein) are used to elucidate the extra- and intracellular protein interactions involved in the transport and metabolic fate of these small molecules. In particular examples, probes of Formula I will exhibit selectivity toward cellulosic endo- and exoglucanases. These probes comprise an activated phenylmethyl aglycone as a binding group that can react with both retaining and inverting functional GHs in a mechanism-based fashion. These binding groups mimic the long-chain polymeric saccharides native to plant cell wall lignocellulose and thus can reveal a wide complement of functionally active cellulases and hemicellulases in S. viridosporus. Probes of Formula I and Formula II are evaluated for their selectivity and reactivity by labeling of purified endoglucanases (GH families 5 and 9), an exoglucanase (GH family 48), xylanases (GH families 10 and 11), and a mannanase (GH family 26) obtained from commercial sources. Probe labeling of the pure enzymes with excess native substrate also is conducted to confirm probe labeling at the active site. Recombinant proteins are spiked into a cell extract of E. coli, which expresses very few GHs, to identify probe selectivity by fluorescent gel analysis. This is performed by adding a probe to the lysate, followed by CC attachment of Alexafluor$_{488}$ and separation of proteins by SDS-PAGE. The spiked lysate studies also are used to perform concentration-dependence and labeling time studies.

Figure 6:
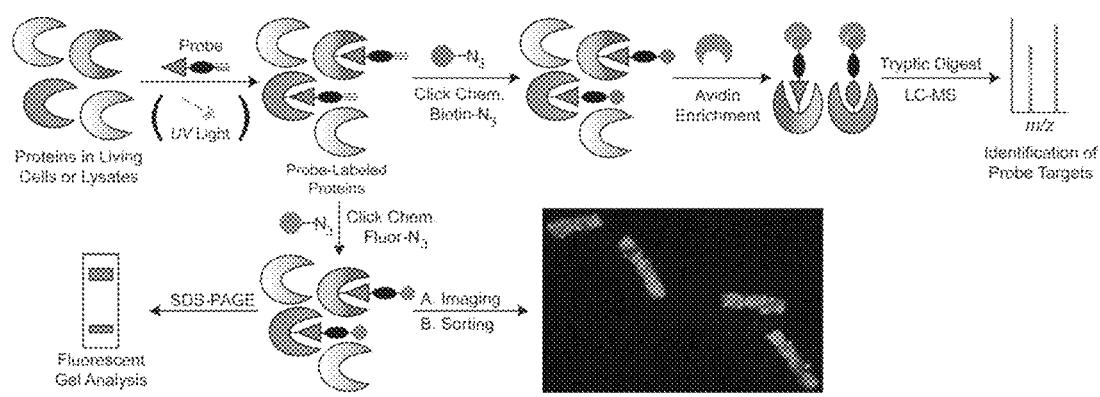
FIG. 6 shows multimodal measurements that can be achieved using function-based probe embodiments described herein, wherein the function-based probes are added directly to living cells or cell lysates and form irreversible bonds to target proteins and wherein click chemistry enables adding biotin for enrichment and quantitative liquid chromatography-mass spectrometry (LC-MS) of probe targets; or wherein fluorophores are added by click chemistry for gel analysis of target proteins, imaging to quantify uptake and distribution of labeling, and/or cell sorting to quantify uptake.

Tag groups (for example, fluorophore or biotin) are directly attached to the probe via the copper-catalyzed bio-orthogonal click chemistry reactions, thereby attaching a tag group to a pTag alkyne or azide group on the probe after it has bound its target. This allows the probe size to be small, thereby minimizing undesirable impacts on reactivity with the target proteins, and maximizing transport and cell permeability. Furthermore, it permits the facile exchange of the type of tag group that is applied to probed targets based on the desired application and outcome of the study, and properties of the sample being assayed. In some examples, biotin is used as the tag moiety to enrich probe-labeled targets for downstream characterization using proteomics and various dyes (for example, AlexaFluor® dyes) are used for super-resolution cellular imaging and flow cytometry. See FIG. 6. Also, the combination of high-resolution, high-sensitivity mass spectrometry (MS) with the probe embodiments is used as a parallel annotation tool to identify functional activities of known and unknown enzymes and potentially all members of an enzyme family simultaneously. Because the disclosed probe technology is independent from sequence-based inference of function, probing S. viridosporus using disclosed probe embodiments is unbiased and can explore even the most divergent enzyme space.

The probe results are coupled to global proteome, RT-PCR, and traditional biochemical activity assays to functionally map and annotate the unique lignocellulolytic mechanism(s), functional associations, and differential functional activity responses to varying feedstock substrates employed by S. viridosporus. Live cell labeling will take into account the concomitant effects of lignin and cellulose catabolites in the extracellular milieu and the dynamics and concerted activities of enzymes and transporters involved in catabolism of lignocellulose and subsequent transport and intracellular metabolism. The exemplary in vivo approach is also highly sensitive and responsive to the differential functional responses of a target enzyme caused by altered growth conditions.

Figure 7A:
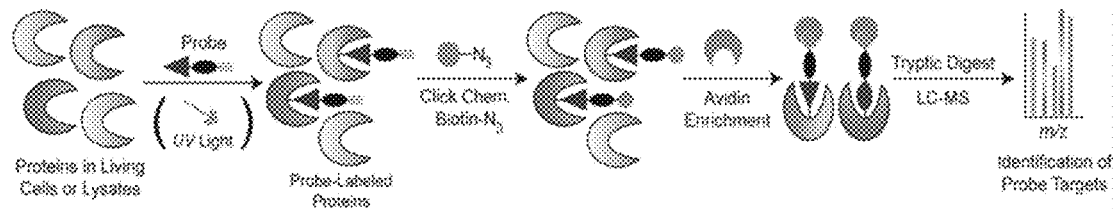
FIGS. 7A-7D show results from method embodiments using certain probe embodiments disclosed herein to conduct function-based probe labeling and further illustrates representative control methods that can be used.
Figure 7B:
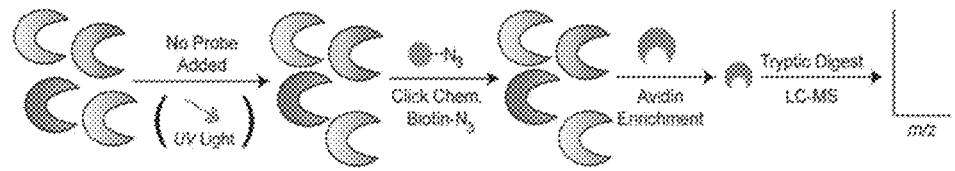
Figure 7C:
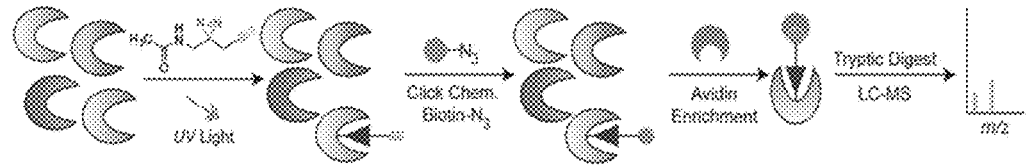
Figure 7D:
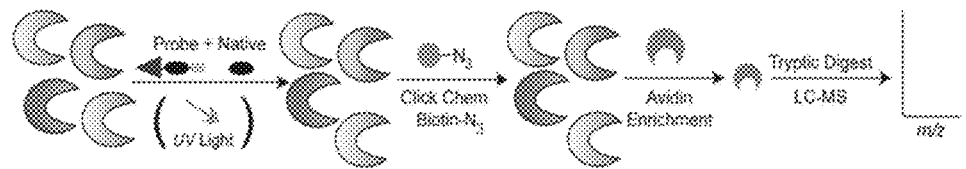

The functionally active cellulases and hemicellulases in S. viridosporus are evaluated at both the compartmentalized (MI) and multinucleated (MII) phases in liquid culture at 37° C. when grown on substrates of increasing complexity. Conditions for growth are adapted from many of the prior studies of S. viridosporus. Six independent replicates are analyzed for cultures on cellobiose, Avicel-PH101 (crystalline cellulose, 50 μm particle size), and untreated switchgrass (20/80 mesh fraction with 18 h of washing at 78° C., courtesy of Dr. Steve Singer, Joint BioEnergy Institute). Optical densities and cell morphology are measured to determine MI and MII growth phases. Probes are directly added into cell culture for short times (5-30 min), and, in some examples, UV-induced cross-linking for diazirine-containing probes is conducted. Click chemistry coupling to a fluorophore (for example, Alexa$_{488}$) is also performed. Separation and visualization of probed proteins by fluorescent SDS-PAGE reveals the efficiency of probe labeling and target overlap by varying probes. Live cell probe labeling with LC-MS proteomic measurements is performed to characterize the specific intra- or extracellular targets of each probe by enriching biotinylated (via CC) probe-labeled proteins by affinity immobilization on streptavidin beads, followed by on-bead trypsin digestion to create peptides amenable to LC-MS analysis (FIG. 7A). Control experiments for LC-MS are conducted for each probe: 1) CC reagents and enrichment is performed in the absence of probe to quantify ABP-independent background binding to the streptavidin resin (FIG. 7B) a "probe" that contains only the diazirine (as appropriate) moieties is added to live cells to assure ABP-identified proteins are not simply a result of the "linker" portion (FIG. 7C) for the sugar probes, which are developed directly from the natural compounds, competitive experiments are employed in which 20-50× native compound is added concomitant with the corresponding probe (FIG. 7D). Thereby, probe targets are out-competed by the native compound resulting in a reduction in probe labeling confirming that the probe targets are true targets of the natural compounds. Blobal proteomics also is used to quantify total protein abundance.

Tryptic peptides generated from post-streptavidin enrichment of probe-labeled control and treated samples are measured by LC-MS/MS. For quantitation, accurate mass and time (AMT) tag approach is used for detection of probe-labeled proteomes. The AMT tag approach is an isotopic label-free method that provides high-sensitivity, dynamic range, comprehensive protein coverage, and high-throughput analysis compared to conventional shotgun proteomic methods relying on MS/MS with inherent under-sampling. High-resolution, high mass accuracy, and high-throughput proteomics also is used for simultaneous identification and accurate quantification of probe targets. LC-MS/MS measurements can be made on Orbitrap Velos instruments. Liquid chromatography options, including long and very small internal diameter columns and constant flow or pressure systems, can be used to provide high sensitivity and improved separations. Data analysis involves using a Proteomics Research Information Storage and Management (PRISM) system, which enables high-throughput proteomic analysis by coupling internally developed databases and analysis tools, including Decon2LS, MutliAlign, VIPER, and DAnTE for statistical analysis. MS function-generating software is used to characterize spectra. This approach can limit false discovery rates to ~1% or less. Data will be normalized.

Example 5

Figure 8:
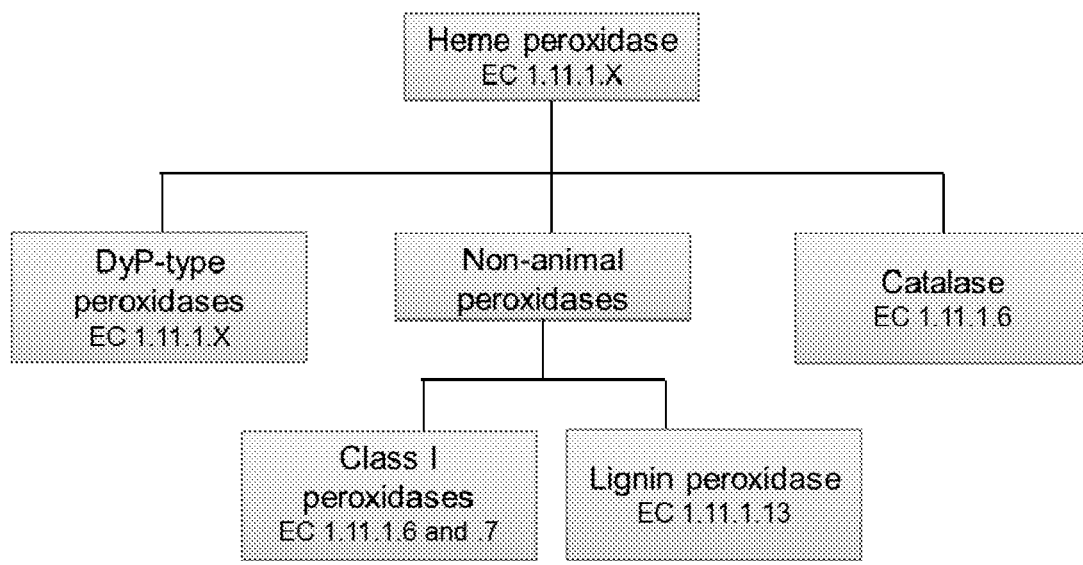
FIG. 8 shows a schematic of the order of various bacterial heme peroxidases.

In this example, probes of Formulas III, IIIA, IIIB, VI, and V are evaluated to characterize lignin degradation and aromatic monomer transport and metabolism. Probes embodiments are tested by reaction with commercially available bacterial peroxidases representing the EC numbers in FIG. 8. Pure proteins are spiked into an E. coli lysate and then labeled to confirm selectivity of the probes. The probes also are evaluated by demonstrating inhibition of a classic peroxidase assay, in anticipation of concentration-dependent inhibition. In particular examples, probes of Formula V are used because their alkyne/diazirine moieties can be attached through an acid off the benzene ring of each lignin monomer. Functionally active heme peroxidases and lignin aromatic monomer transport and metabolism in S. viridosporus is evaluated at both MI and MII growth phases at 37° C. Six independent replicates for cultures on untreated switchgrass are prepared, and standard commercial peroxidase assays are measured to determine the combined activity levels. Cell morphology and optical densities are measured to determine MI and MII growth phases. Optimal probe labeling times and concentrations are determined by labeling cell lysate of *S. viridosporus*, and evaluating the number and intensity of targets by fluorescent SDS-PAGE. Competition studies in the lysate are conducted with native or model compounds that represent each of the probe types. These lysate experiments can provide greater confirmation that each probe is selective and reactive at concentration levels that will not completely skew the physiology of the cell. To characterize the specific intra- or extracellular targets of each probe, live cell labeling is performed followed by LC-MS proteomic measurements at MI and MII growth phases, including controls. Measurement and informatics approaches will be applied as described above in Example 4.

In another example, probes are assayed by reaction with commercially available bacterial peroxidases, and probe selectivity is assayed by spiking pure proteins into *E. coli* lysate and then labeling. The probes are further validated by demonstrating inhibition of a classic peroxidase assay. Lignin-degrading enzymes are typically extracellular, but they can also be tethered to an extracellular surface, consistent with data showing cell sorting within a soil microbial community with a cellulase probe. Microbes (for example, Novosphingobium) that contain transport functions for lignin catabolites are assayed.

Also, series of probes were constructed based on amino acids, including Phe, Trp, Val, Ile, and Met. Each probe contains a photoreactive diazirine to irreversibly label transporters or intracellular proteins and an alkyne to enable click chemistry to attach fluorophores or enrichment moieties. In addition, rapid solid-phase resin synthesis can be used for synthesis of new amino acid probes in as little as one day. A method for validating cell permeability and target selectivity of new amino acid probes in *E. coli* mutants can also be used.

In one example, "standard" fluorescent dyes (for example, ALEXAFLUOR488® or other members of the ALEXAFLUOR series; tetramethylrhodamine; Atto633, and the like) are used to sort probe-labeled microbial cells from complex communities. Where small cell size or low copy number of proteins result in low fluorescence signal or a low signal:noise ratio is exceedingly low and sufficient gate cannot be set on the flow cytometer, reporter tags were chemically synthesized to maximize signal. Fluorescence signal is also enhanced by increasing the number of fluorophores available for detection. In one example, signal is enhanced by synthesizing reporting groups as polymeric fluorophores that contain an azide moiety to enable click chemistry, and a PEG spacing group is used to impart cell permeability and separation of fluorophores, mitigating quenching. The synthesis is performed rapidly using solid-phase combinatorial chemistries, and spacing between fluorophores is tunable by changing the number of ethylene glycol units. Fluorophores are obtained as N-hydroxysuccinimidyl esters for rapid and facile conjugation to the lysine residues in the backbone of the polymer. In addition, dyes (for example, eFluor450, ALEXAFLUOR488®, Ethidium Homodimer) that excite at wavelengths matching the lasers present on the BD® FACSAriall sorter (405 nm, 488 nm, 633 nm) can be utilized. Application of the present proves and methodologies can be used to identify and characterize various microbial community types.

In Table 2 various examples of new candidate phylum-level and/or uncharacterized lineages where this methodology could be employed are provided. Probe sets directed toward identifying functions for amino acid transport and metabolism, extracellular lignin and cellulose hydrolysis, transport, and intracellular metabolism, and hydrocarbon degradation could be utilized. In another example, function-based probes are designed to be cell permeable and reactive with specific enzymes, enzyme families, or protein/transporter interactions. The first step of the workflow consists of incubating microbial communities with a specific concentration of probe (typically 0.5-200 µM) for a defined period of time (5-60 minutes). All attempts will be made to probe label in the native media and temperature. The specific probe concentration and exposure time are community and probe-dependent, and are optimized using SDS-PAGE based analysis of protein labeling. The labeled microbial community is then prepared for sorting. Cells are ethanol fixed and permeabilized, as this fixation method is compatible with various standard single cell genome sequencing pipelines. This method is also applicable without requiring fixation. In this particular application, a single cell suspension is obtained by brief sonication or via shear force generated by passage through a 21-gauge needle. A fluorophore is then covalently attached to the probe using click chemistry. Unbound fluorophore is washed away and cells are resuspended in a FACS buffer containing a fluorescent nucleic acid stain.

In this application, the final step uses FACS to isolate function-dependent probe-labeled microbial cell populations. Single-cell suspensions are loaded onto a cell sorter prepared for aseptic sorting with DNA/RNA-free sheath fluid. Scatter and fluorescence of the nucleic acid dye are used to identify microbes, and fluorescence from the probed proteins is used to identify activity-positive or -negative cells. Cells can be sorted into tubes, collected on a filter, and DNA obtained for population-level analysis. Alternatively, single cells can be collected in a 96-well plate for single-cell whole genome amplification. The DNA is then sequenced and isolated. Functional probe-based microbial community studies will elicit information to identify operational taxonomic units (OTUs) enriched in the probe activity-positive cell fractions, conduct metagenomic analysis of the different subsets, and obtain complete genome sequences of bacteria exhibiting the function of interest, potentially leading to the identification of novel OTUs.

Three distinct communities consisting of a laboratory model unicyanobacterial consortium (UCC) and two samples of soil from geographically distinct regions (referred to herein as KS and WA, respectively) were processed. Community samples were exposed to either a monooxygenase probe ("2EN"; 20 µM for KS and WA), a protein thiol redox probe ("IAA"; 20 µM for UCC), or a cellulase probe ("6A"; 20 µM for WA) for 1 hour. No probe controls were included for all samples. Immediately after labeling, cells were washed to remove unbound probe, fixed, and permeabilized in cold 70% ethanol for 1 hour. A fluorophore, ALEXAFLUOR488®, was added via click chemistry. To sort labeled from unlabeled cells, samples were suspended in FACS buffer (1% BSA; 50 mM EDTA in PBS) containing 4 µM ethidium homodimer and loaded on a BD FACSAriall sorter. Cells of interest were identified by light scattering compared to 0.1 µm, 0.5 µm, and 1 µm beads and ethidium homodimer fluorescence. Cells with higher ALEXAFLUOR488® fluorescence than the no probe controls were defined as probe-positive ("+"), while cells with fluorescence falling in the same gate as the no probe controls were defined as probe-negative ("−"). Both probe-positive and probe-negative fractions were collected (FIGS. 9B-9E). The probes labeled only a portion of the cells (i.e., function-dependent labeling), and there is a clear differential response between distinct communities (compare FIGS. 9C and 9D).

To confirm isolation of microbial DNA in sorted cells, PCR was performed using universal primers spanning the V3-V4 regions of the 16S rRNA gene. As shown in FIG. 9F, amplification was observed for all samples, but not in the elution buffer-only control. In addition, DNA yield was higher in samples with more sorted cells (for example, comparing WA 2EN+ (less) to WA 2EN− (more) in FIG. 9F). These data suggest that genomic DNA was successfully isolated from sorted cells and that this DNA serves as template for PCR and sequencing. These data show specific functional labeling of microbes.

Example 6

In this example, the functional association between cellulolytic activity and lignin degradation by function-based probes of *S. viridosporus* is evaluated. *S. viridosporus* is grown on switchgrass, Douglas fir sawdust (forest softwood), and white oak sawdust (forest hardwood) to MI and MII growth phases. For each culture type, six replicates are prepared, and common cellulase, xylanase, and peroxidase assays will be performed on each. Biomass depletion throughout growth on each substrate is evaluated. Probes embodiments described herein are added individually in vivo to the cultures. The transport of lignin monomers and the (oligo)saccharides is quantitated by flow cytometry. This measures the alterations to uptake at the different time points for each substrate and specifically point to how different culture durations and substrates influence transport and intracellular metabolism. Quantitative proteomic analyses for all probes at all times and substrates is then performed as discussed in Examples 4 and/or 5. Statistical analyses are used to characterize the probe-labeled enzyme, transport, and metabolism activities that are changing to the greatest amount. First, how growth at each time point changes on a single substrate is characterized. This is then evaluated across substrates to identify specific alterations that may be drivers of mechanistic changes. For example, the bacterium may increase a particular cellulase while decreasing a specific peroxidase, or transport of a particular aromatic monomer may correlate directly to a peroxidase activity. These couplings may also point to mechanisms by which *S. viridosporus* could be optimized to be an efficient biorefinery of lignocellulose. Alternatively, it may point to ways plants could be genetically altered to generate biomass most suitable for deconstruction by *S. viridosporus*. Finally, activity changes are evaluated and it is determined whether functional activity is concomitant with transcription and protein abundance or if it is dependent on post-translational and environmental queues. Global proteome analyses are performed and genes of high interest are selected for RT-PCR analysis.

Example 7

Synthesis of GlcA-ABP

NMR spectra were recorded on a 499.8 MHz $^1$H, 125.7 MHz $^{13}$C NMR spectrometer at 25° C. Chemical shifts are reported in parts per million (ppm—δ) referenced to the NMR solvent residual peak, and coupling constants (J) are in hertz (Hz) and multiplicities indicated with: singlet (s), doublet (d), triplet (t), doublet of doublets (dd), doublet of triplets (dt), doublet of doublet of doublets (ddd), and multiplet (m) as recorded. Silica gel flash column chromatography was used to purify all compounds using a BIOTAGE® purification system, and prepacked columns for the same were from LUKNOVA®. Reagents and solvents were from commercial suppliers and used as-is without further purification. Wherever necessary, anhydrous solvents were produced using a solvent purification system. All reactions were monitored using TLC and THERMO SCIENTIFIC® LTQ-MS. Reactions were carried out under nitrogen ($N_2$) atmosphere wherever necessary. For characterization of new compounds, $^1$H, $^{13}$C NMR, $^{19}$F, and LTQ-MS data are included, whereas, for known compounds, only $^1$H NMR data is reported with appropriate literature reference.

Preparation of 2-(2-formyl-4-nitrophenoxy)-6-(methoxycarbonyl)tetrahydro-2H-pyran-3,4,5-triyl triacetate (2)

A clean and dry 100 mL round bottom flask with stir bar was charged with 1 (0.749 g, 1.89 mmol), 2-hydroxy-5-nitrobenzaldehyde (0.316 g, 1.89 mmol), and acetonitrile (50 mL) and allowed to stir for 5 minutes. $Ag_2O$ (0.435 g, 1.89 mmol) was carefully added to the reaction mixture and stirred at room temperature for 4 hours. After confirming completion of reaction by LTQ-MS (m/z 484; M+H) using a filtered aliquot giving a desired mass, the reaction was stopped, and $Ag_2O$ was filtered out over a celite bed. The solvents were removed using a rotatory evaporator to give rise to a dark brown crude product, which was further purified using flash chromatography (ethyl acetate:hexanes; 1:2) to give the desired aldehyde 2 as a buff solid (0.62 g; 67%). $^1$H NMR ($CDCl_3$; 500 MHz) δ 10.32 (s, 1H), 8.70 (br s, 1H), 8.41 (d, J=6.5 Hz, 1H), 7.28 (d, J=9.9 Hz, 1H), 5.46-5.39 (obscured m, 5H), 3.73 (s, 3H), 2.02 (m, 9H,) ppm.

Preparation of 2-(2-(difluoromethyl)-4-nitrophenoxy)-6-(methoxycarbonyl)tetrahydro-2H-pyran-3,4,5-triyl triacetate (3)

Compound 2 (0.401 g, 0.83 mmol) was dissolved in anhydrous dichloromethane (50 mL), cooled in an ice bath, and allowed to stir for 5 minutes under a constant purge of $N_2$. Diethylaminosulfur trifluoride (DAST) (0.66 g, 4.2 mmol) was dissolved in anhydrous dichloromethane (5 mL) and added drop-wise to the reaction mixture, after which the reaction mixture was stirred at 0° C. for 3 hours. After confirming the completion of the reaction by TLC and LTQ-MS, the reaction was quenched by aqueous $NaHCO_3$ solution. The contents were transferred to a separatory funnel containing 50 mL dichloromethane, and the organic layer was washed with water (3×25 mL) and brine (1×25 mL), after which the dichloromethane layer was separated, dried over anhydrous MgSO4, and filtered. The solvent was evaporated using a rotatory evaporator to obtain crude product, which was further purified via flash chromatography using ethyl acetate:hexanes (1:2) to give 3 (0.39 g, 92%) as a white solid. $^1$H NMR ($CD_3OD$; 500 MHz) δ 8.42 (s, 1H), 7.45 (d, J=9.0 Hz, 1H), 7.03-6.81 (br t, J=54.4 Hz, 1H), 5.67 (d, J=7.5 Hz, 1H), 5.50 (t, J=9.5 Hz, 1H), 5.32 (obscured t, 1H), 5.25 (t, J=9.5 Hz, 1H), 4.61 (d, J=9.5 Hz, 1H), 3.72 (s, 3H), 2.07-2.03 (br s, 9H) ppm.

Preparation of 2-(2-(difluoromethyl)-4-(hex-5-ynamido)phenoxy)-6-(methoxycarbonyl)tetrahydro-2H-pyran-3,4,5-triyl triacetate (5)

A clean and dry 50 mL round bottom flask with a stir bar was flushed with $N_2$ for 5 minutes, charged with compound 3 (0.201 g, 0.39 mmol) and dissolved in EtOAc (25 mL). To this, activated (heated in oven at 105° C. overnight) Pd/C (0.4 g) was added, and the reaction mixture was purged by bubbling $H_2$ gas (via a balloon) through the reaction mixture for 5 min. The reaction was then maintained under a balloon of $H_2$ for 15-20 hours. After confirming the completion of reaction by TLC (2:1 Hex/EtOAc), the $H_2$ balloon was carefully detached, and the reacting mixture was purged with $N_2$. Under an $N_2$ flow, the contents were filtered over a bed of Celite using dichloromethane as solvent. The filtrate was the concentrated by evaporating solvents using a rotatory evaporator to yield amine 4 (0.180 g, 95%) as a pale yellow solid, the mass was confirmed using an LTQ-MS (m/z 476; M+H), and the compound was used in the subsequent step without purification.

To a 100 mL round bottom flask with stir bar, 5-hexynoic acid (1.00 g) dissolved in dichloromethane (50 mL) was added, and, to this, $SOCl_2$ (10 eq) was added. The reaction mixture was refluxed for 6 hours, and then solvents were evaporated using a rotatory evaporator to give hexynoyl chloride as a crude oil, which was then reacted with amine 4.

Amine 4 (0.125 g, 0.26 mmol) was dissolved in anhydrous dichloromethane (25 mL) containing trimethyl amine (0.080 g, 0.78 mmol) and stirred for 5 minutes. Hexynoyl chloride (0.070 g, 0.53 mmol) was dissolved in dichloromethane (2 mL) and slowly added to the reaction mixture dropwise over 5 minutes. The resulting solution was then stirred for 12 hours at room temperature, the completion was eventually confirmed using LTQ-MS (m/z 570, M+H). The reaction mixture was diluted with dichloromethane (50 mL), and the contents were transferred to a separatory funnel. The organic layer was washed with saturated $NaHCO_3$ (2×25 mL), $H_2O$ (2×30 mL) and brine (1×50 mL). The organic layer was dried over $Na_2SO_4$, filtered, and concentrated by evaporating solvents using a rotary evaporator to give crude product, which was purified by flash column chromatography (1:1 EtOAc/Hex) to give 5 (0.161 g, 77%) as a white solid. $^1H$ NMR (CD$_3$OD, 500 MHz): δ 7.77 (s, 1H), 7.69 (d, J=9.0 Hz, 1H), 7.19 (d, J=9.0 Hz, 1H), 6.96-6.74 (br t, J(H,F)=55.5 Hz, 1H), 5.49-5.44 (obscured d, 1H), 5.40 (d, J=8.0 Hz, 1H), 5.26-5.20 (m, 2H), 4.52 (d, J=10.0 Hz, 1H), 3.73 (s, 3H), 2.50 (t, J=7.5 Hz, 2H), 2.30-2.27 (m, 3H), 2.04-2.03 (m, 9H), 1.91-1.87 (m, 2H); $^{13}C$ NMR (CD$_3$OD, 125 MHz): δ 172.3, 169.9, 169.7, 167.4, 134.3, 123.3, 117.3, 116.0, 98.7, 82.6, 71.6, 71.5, 70.7, 69.3, 68. 9, 51.9, 35.0, 24.1, 19.0, 18.9, 17.2; $^{19}F$ NMR (CD$_3$OD, 470 MHz) −111.26, −111.38, −111.90, −112.02, −121.23, −121.34, −121.87, −121.98; HRMS m/z (M+H) calculated for $C_{27}H_{29}F_2NO_{11}$: 569.51, observed: 570.49.

Preparation of 6-(2-(difluoromethyl)-4-(hex-5-ynamido)phenoxy)-3,4,5-trihydroxytetrahydro-2H-pyran-2-carboxylic acid (6)

5 (0.101 g, 0.175 mmol) was dissolved in anhydrous MeOH (20 mL) in a 100 mL round bottom flask and stirred for 5 minutes. NaOCH$_3$ in methanol (25% wt/v; 0.030 g, 0.536 mmol) was dissolved in methanol (5 mL) and added to the reaction mixture slowly by syringe. The reaction mixture stirred at room temperature for 3 hours. After confirming the completion of the reaction by LTQ-MS (m/z 428, M−H), the reaction was stopped, and solvents were evaporated using a rotatory evaporator to leave a crude oil. Final purification via flash chromatography using 100% ethyl acetate gave GlcA-ABP (6) as a yellow-brown solid (0.061 g, 80%). $^1H$ NMR (CD$_3$OD, 500 MHz): δ 8.53 (s, 1H), 7.80 (s, 1H), 7.62 (br d, J=7.5 Hz, 1H), 7.29 (obscured s, 1H), 7.27-7.06 (br t, J=55.5 Hz, 1H), 4.58 (br s, 1H), 3.78 (d, J=9.5 Hz, 1H), 3.57-3.55 (m, 1H), 3.54-3.51 (m, 2H), 3.35 (s, 1H), 2.50 (t, J=7.5 Hz, 2H), 2.30-2.27 (m, 3H), 1.93-1.87 (m, 2H); $^{13}C$ NMR (CD$_3$OD, 125 MHz): δ 172.3, 169.8, 168.8, 151.5, 149.3, 135.0, 133.7, 123.3, 117.1, 116.8, 82.7, 76.3, 75.2, 73.2, 72.0, 68.8, 35.0, 24.2, 17.2; $^{19}F$ NMR (CD$_3$OD, 470 MHz) −114.70, −114.81, 115.34, −115.46, −116.98, −117.09, −117.62, −117.74; HRMS m/z (M+) calculated for $C_{19}H_{21}F_2NO_8$: 429.37, observed: 428.11 [M−H].

In Vitro Fluorescence Labeling and Gel Imaging

Purified proteins (5 μM) or cell lysate (1 mg/mL) were treated with varying concentrations of GlcA-ABP for 1 hour at 37° C. Rhodamine was attached via copper catalyzed azide-alkyne cycloaddition (CuAAC) as previously described, and proteins were analyzed via SDS-PAGE. Gels were imaged using a GE® TYPHOON® FLA-9500 and band intensity was quantified using ImageJ.

Fluorescent Labeling of Microbes and Cell Sorting

Figure 10:
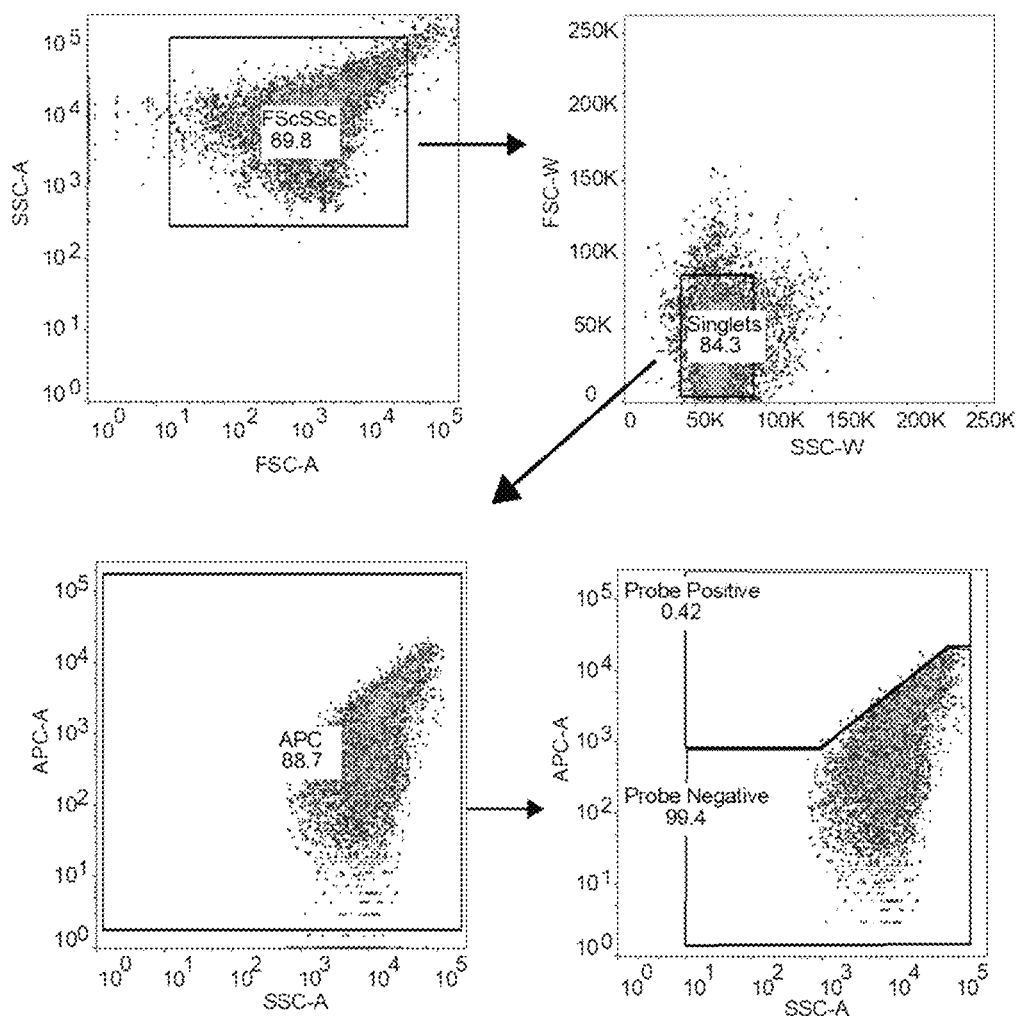
FIG. 10 shows a general gating strategy for isolation of GlcA-ABP+/– populations wherein side-scatter and a SYBR® Gold signal were used for an event threshold, and the cells were gated on Forward and Side scatter, pulse duration, CF®640-R to remove debris, and then CF®640-R; gates were drawn such that >95% of events in the No Probe control sample were considered "Probe Negative."

Overnight cultures (5 mL) were collected via centrifugation resuspended in 1 mL of PBS, and 100 μL was transferred into aliquots. Aliquots were treated with 50 μM GlcA-ABP, 10 μM iodoacetamide alkyne (IAA), or an equal volume of vehicle ('No Probe'; DMSO). Cells were incubated with shaking for 1 hour at 37° C. Cells collected via centrifugation at 10,000 g for 5 minutes and washed 3× with 1 mL deoxygenated PBS. Pellets were resuspended in 100 μL PBS and fixed with 70% ethanol (1 mL) at −20° C. overnight. Cells were washed twice via resuspension in 1 mL PBS and centrifugation at 10,000 g for 5 minutes. Cells were resuspended in 250 μM CuAAC reaction buffer (10 μM CF640R picolyl azide, 8 mM $CuSO_4$, 2 mM THPTA, 10 mM ascorbic acid in PBS:0.5% (w/v) BSA). One-half of the No Probe sample was used as a no fluorescence control (CuAAC reaction buffer without CF640R). Cells were incubated in the dark with rotation at room temperature for 1 hour and collected by centrifugation as above. Cells were washed 4× by resuspension in 1 mL PBS:0.5% BSA, incubating with rotation for 5 minutes in the dark at room temperature, and centrifuged as above. Cells were resuspended in PBS with SYBR® Gold (LIFE TECHNOLOGIES®; 1:10,000) and analyzed using a BD® FACSARIA® Ilu with autoclaved sheath fluid. Forward and side scatter (488 nm), SYBR® Gold (488 nm excitation; 530/30 nm detection filter) and CF)640R (633 nm excitation; 660/20 nm detection filter) parameters were collected. Gates were drawn such that >95% of events in the No Probe sample were classified as Probe Negative (FIG. 10). Flow cytometry data were collected using FACSDIVA® 8 (BD Biosciences) and analyzed using FLOWJO® 10.

Fluorescence Labeling and Sorting of Gut Microbes

Microbial cells were collected and sorted as previously described with some modifications. Lower intestinal tract from ileum to rectum was collected and placed into 50 mL conical tubes containing approximately 5 mL sterile glass beads (3 mm diameter) and 20 mL of deoxygenated PBS. The tubes were quickly transferred to an anaerobic chamber, and 1 mM dithiothreitol was added to aid in microbial recovery and incubated for 5 minutes. The suspended intestinal content was then transferred into a new tube, vortexed for 30 seconds, and large debris precipitated for 5 minutes. The supernatant was collected and centrifuged at 700 g for 15 minutes. The supernatant was transferred to a clean 50 mL conical and centrifuged at 8,000 g for 15 minutes to collect bacterial cells. The bacterial cell pellet was washed once via resuspension in 1 mL of deoxygenated PBS and centrifuging at 8,000 g for 15 minutes. Cells were then labeled and sorted as described above.

DNA Isolation and Amplicon Sequencing

Where possible, 2,000,000 events (using side scatter and SYBR® Gold as threshold parameters) were collected via 4-way purity sort in UV-irradiated glass tubes. Enrichment was confirmed by re-analyzing a small aliquot of the sorted cells. Cells were collected via centrifugation at 12,000 g for 10 minutes into 1.5 mL tubes and resuspended in lysis buffer (50 mM NaCl, 10 mM Tris HCl, 5 mM EDTA, 0.5% SDS, and 0.1% β-mercaptoethanol). To control for background DNA contamination, 50,000 beads were collected in a separate tube, and one tube of lysis buffer only was prepared with each sort. The tubes were incubated at 4° C. for 30 minutes and then lysed via five freeze/thaw cycles using liquid nitrogen. DNA was then extracted and purified (Zymogen DNA Clean & Concentration-5). PCR amplification of the V4 region of the 16S rRNA gene was performed using the protocol developed by the Earth Microbiome Project and described in Walters et al. Amplicons were sequenced on an ILLUMINA® MISEQ® using the 500 cycle MISEQ® Reagent Kit v2 per manufacturer's instructions.

Bioinformatics Analysis

Sequences were analyzed using an in-house pipeline. Briefly, raw sequence reads were demultiplexed with using EA-Utils with zero mismatches allowed in the barcode sequence. Reads were quality filtered with BBDuk2 to remove adapter sequences and PhiX with matching kmer length of 31 bp at a hamming distance of 1. Reads shorter than 51 bp were discarded. Reads were merged using USEARCH with a minimum length threshold of 175 bp and maximum error rate of 1%. Sequences were dereplicated (minimum sequence abundance of 2) and clustered using the distance-based, greedy clustering method of USEARCH at blast % pairwise sequence identity among operational taxonomic unit (OTU) member sequences. De novo prediction of chimeric sequences was performed using USEARCH during clustering. Taxonomy was assigned to OTU sequences using BLAST® alignments followed by least common ancestor assignments across SILVA database version 123 clustered at 99%. OTU seed sequences were filtered against SILVA database version 123 clustered at 99% to identify chimeric OTUs using USEARCH. OTUs for which the read count was higher in the 'Beads' or 'Control' sample compared with samples from sorted cells were excluded from further analysis.

Differential Abundance Analysis

For each OTU and comparison, a differential abundance test was performed using a compositional data analysis approach with the ALDEx2 package in R replacing the typical glm in the algorithm with a mixed effects model including a random effect accounting for littermates. Additionally, a qualitative g-test for systematic differences in presence/absence between two groups was run for each OTU and comparison. Differences with adjusted $p<0.05$ were considered significant.

Differentially abundant taxa were graphed using GraPhlAn.

β-Glucuronidase Activity Assays

Microbial cells from the mouse gut were suspended in PBS with a protease inhibitor (COMPLETE® EDTA-free Protease Inhibitor, ROCHE®) and lysed via bead beating (BULLET BLENDER®). β-glucuronidase assays were conducted as previously described with modifications. Briefly, 4-methylumbelliferyl-β-D-glucuronide (4-MUG; 1 mM) was added to 50 μL lysate (0.9 μg total protein) for a final concentration of 500 μM. At specific time points (0-240 minutes), 10 μL aliquots of each reaction were added to 90 μL of 0.1 M $Na_2HCO_3$ (pH=10) and stored in the dark. Fluorescence was measured using a plate reader (MOLECULAR BIOSCIENCES®), and the amount of hydrolyzed substrate was calculated relative to a standard curve. The rate (mM/s) was determined via linear regression (GRAPHPAD® PRISM®), and activity was calculated as rate per μg protein. Values from three independent replicates were averaged, and activity was compared across biological replicates (n=5) using a ratio paired t-test.

Correlation Analysis

Glucuronidase activity was correlated to OTU relative abundance in the total population of control and vancomycin-treated samples. The high activity value for one sample (litter set E control) in the water treatment is much larger than all other values and drastically affected statistical results; thus, these samples were excluded from the analyses. Additionally, OTUs with a large number of zeros (more than ⅔ of samples had observed 0 counts) were excluded, as any results from these OTUs would likely be spurious. For the remaining OTUs, the Pearson correlation between the normalized OTU abundance and glucuronidase activity were calculated, and a hypothesis test for significance was performed. Correlation was considered significant at a 0.05 level of significance.

A platform employing function-based probes to detect, isolate, and identify microbial populations responsible for xenobiotic metabolism was developed. Described herein is a probe for β-glucuronidases, which are enzymes capable of reversing a major pathway in phase II metabolism that is responsible for xenobiotic clearance. Using this probe, active enzymes were covalently labeled both in vitro and in live bacterial cells in the mouse gut microbiota. Cells with active β-glucuronidases were labeled by the probe, fluorescently tagged, isolated, and identified by sequencing. The probe platform was used to demonstrate that the metabolic activity of the gut microbiota can be plastic and that, during perturbation, phylogenetically disparate populations can reconstitute β-glucuronidase activities. The use of probe in the gut microbiome moves beyond genomic inference and constitutes a new, powerful approach to combine measurement of biochemical activity with molecular-scale resolution.

The probe is a small molecule substrates that, upon activation by a catalytically active target enzyme, form a covalent bond with that enzyme. Because the probes only label when an active enzyme is present, the probe can be used to demonstrate activity in lysate, live cells, or tissue. Furthermore, the use of generalized bio-orthogonal tags facilitates enrichment of labeling events and measurement by proteomics or tagging with a fluorophore for imaging, SDS-PAGE, or fluorescence-activated cell sorting (FACS). FACS-based approaches can be used to study activity in the context of microbial communities. By combining FACS with the probe, cells with active enzyme can be sorted, and genomic sequencing can be used to identify the community members. Thus, taxa can be identified based on activity rather than potential activity (e.g., by genes or transcripts), which addresses a major hurdle to understanding host-microbe-xenobiotic interactions.

A pathway modulated by the gut microbiome is glucuronidation. Glucuronidation facilitates mammalian Phase II metabolism and clearance of xenobiotics, which is mediated by conjugation of a glucuronic acid to xenobiotics and endogenous metabolites to increase their solubility. Microbial β-glucuronidases in the gut can hydrolyze the conjugate back to the parent compound, leading to altered pharmacodynamics, failure of therapeutics, or severe side effects. Recent work has identified conserved motifs to improve annotation of β-glucuronidases; however, these genes are widespread amongst members of the gut microbiota, making prediction of the specific taxa active in deglucuronidation extremely difficult.

Figure 11A:
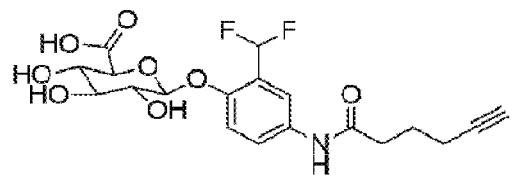
FIGS. 11A-11E show that GlcA-ABP labels proteins and cells in a β-glucuronidase-dependent manner.
Figure 11A:
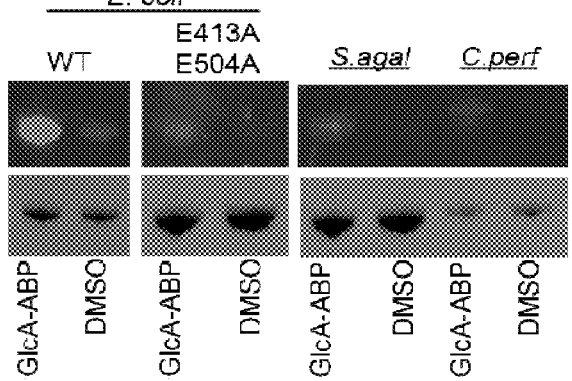
Figure 11B:
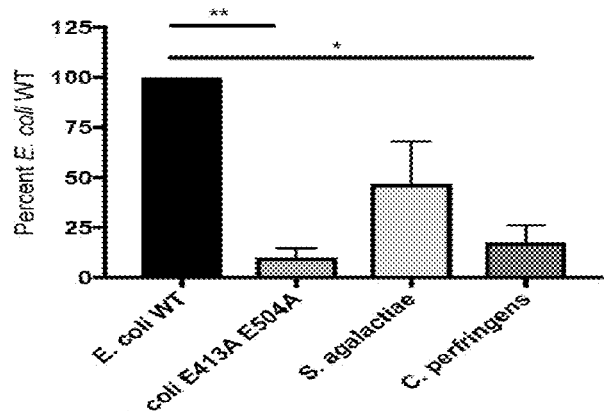

A function-based probe for β-glucuronidases was developed that can characterize functional activity in the gut microbiome. Given the ubiquity of these genes, activity should be spread throughout phylogenetically distinct taxa. To better define this activity in situ, GlcA-ABP was synthesized, which mimics a glucuronidated metabolite and bears a reactive group attached to the anomeric position of glucuronic acid as well as an alkyne moiety for reporter group attachment (FIG. 11A). When an active glucuronidase reacts with the probe, an electrophilic o-quinone methide forms and is attacked by a nearby nucleophilic residue, creating a covalent bond. The alkyne handle of GlcA-ABP enables fluorophore attachment via copper-catalyzed azide-alkyne cycloaddition (CuAAC). To demonstrate probe efficacy, in vitro probe labeling was performed using recombinantly expressed and purified β-glucuronidases from *Escherichia coli*, *Streptococcus agalactiae*, and *Clostridium perfringens*. Enzymes were treated with GlcA-ABP, tagged with rhodamine-azide, and analyzed by SDS-PAGE. GlcA-ABP labeling intensity corresponded with the catalytic efficiency of these enzymes (FIGS. 11A and 11B). Mutation of the catalytic residues from glutamate to alanine abolished probe labeling, confirming that GlcA-ABP probe labels β-glucuronidases in an activity-dependent manner (FIGS. 11A and 11B).

Figure 11C:
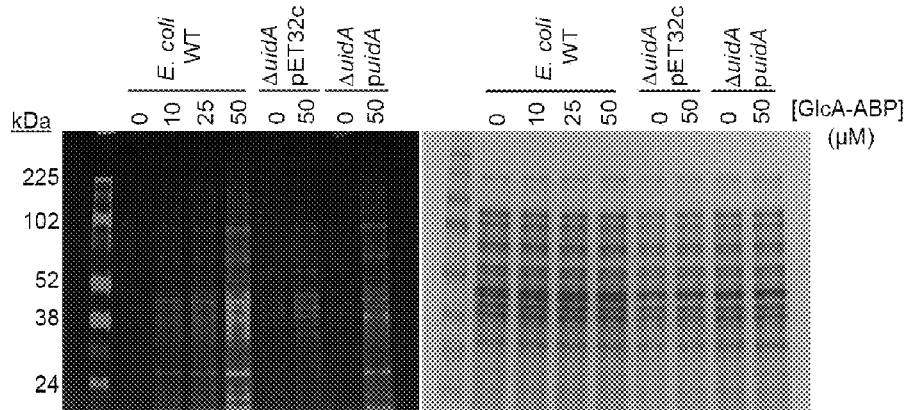
Figure 11D:
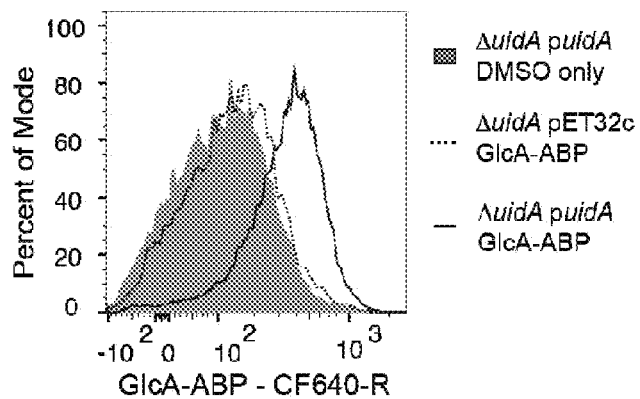
Figure 11E:
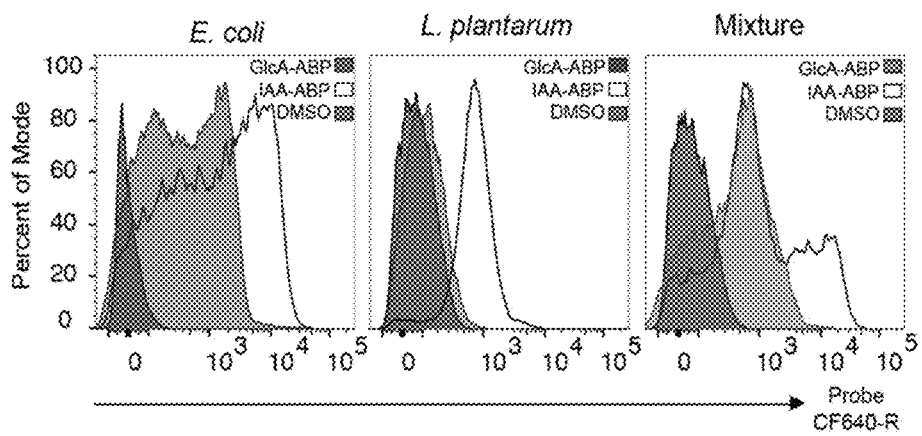
Figure 11E:
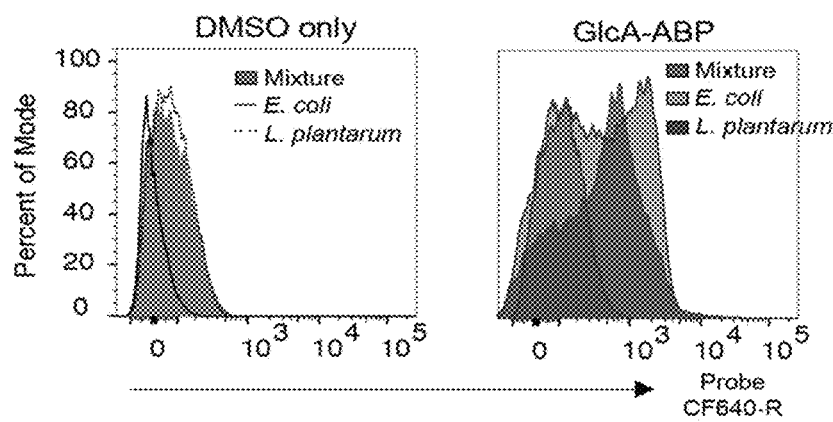

An *E. coli* strain that lacks uidA (ΔuidA), which encodes for β-glucuronidase, was used for in vivo activity assays. Live cells were treated with GlcA-ABP, lysed, and fluorescently tagged by CuAAC, and labeled enzymes were visualized by SDS-PAGE (FIG. 11C). Dose-dependent labeling was observed in wild type (WT) *E. coli*; no labeling was observed in ΔuidA, which encodes for the β-glucuronidase; and restoration of labeling was observed in ΔuidA complemented with uidA both by SDS-PAGE and flow cytometry (FIG. 11D). WT *E. coli* and *Lactobacillus plantarum*, which lacks a β-glucuronidase, were used to assay for coupling probe labeling to FACS. The labels included WT *E. coli* only, *L. plantarum* only, or a mix of the two with GlcA-ABP or a positive control iodoacetamide alkyne (IAA) probe. Cells were fixed, fluorescently tagged via CuAAC, and analyzed by flow cytometry. While all cells were labeled by IAA, GlcA-ABP labeling was observed in *E. coli* only, but none in *L. plantarum* only and an intermediate amount in the mixture (FIG. 11E). These data demonstrate that GlcA-ABP can be used to label and sort cells possessing active β-glucuronidases from a mixed population of microbes.

Figure 12:
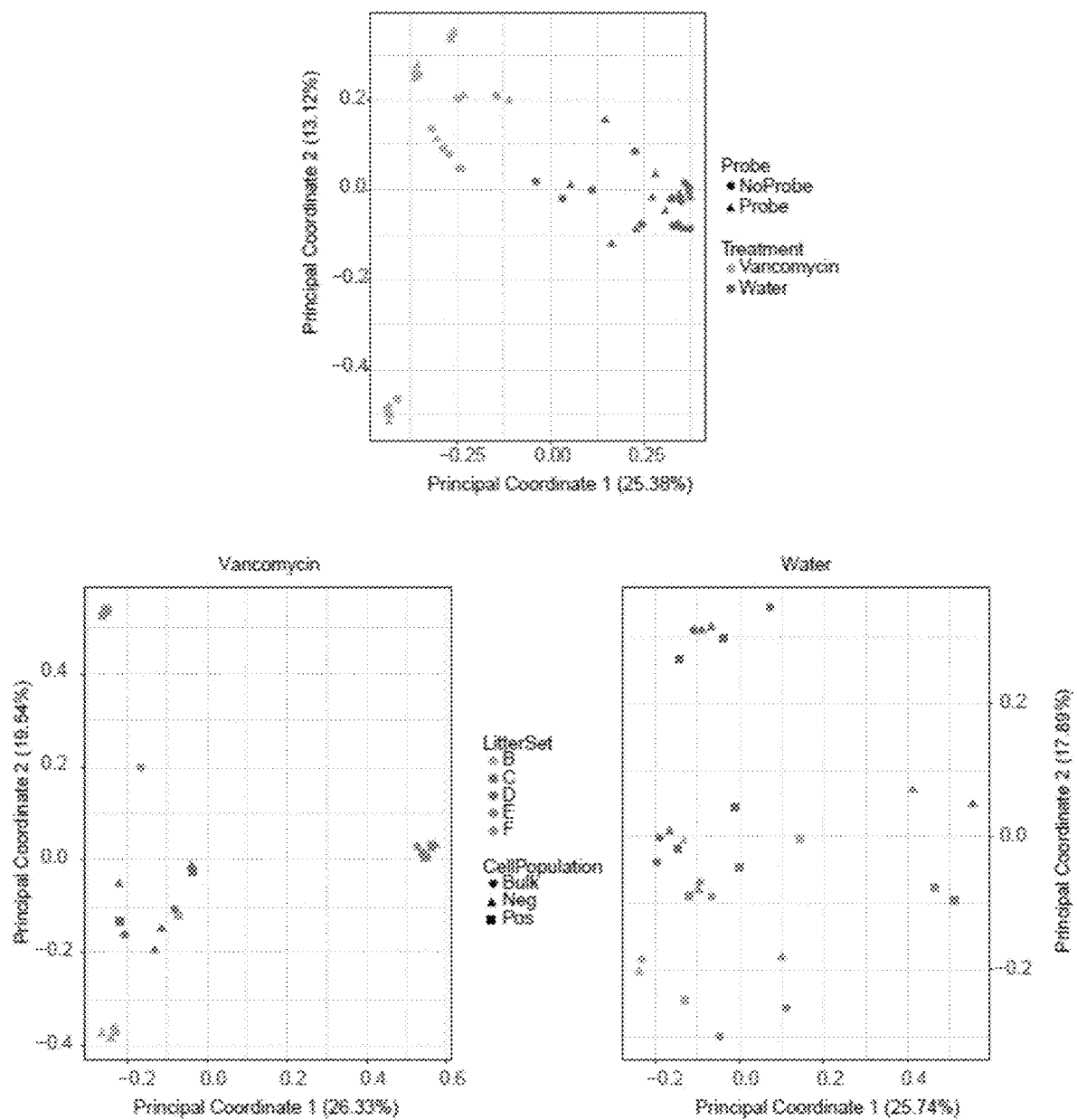
FIG. 12 shows β-diversity among input, GlcA-ABP+, and GlcA-ABP– populations wherein a Bray-Curtis dissimilarity analysis of sequenced populations from all (top), control (bottom right), or vancomycin-treated (bottom left) mice was performed.

Glucuronidase-active members of the gut microbiota were then sought. Microbes were isolated from the mouse gastrointestinal tract and incubated with GlcA-ABP under anaerobic conditions. Cells were fixed, fluorescently tagged, and sorted into populations of probe-positive (GlcA-ABP+), probe-negative (GlcA-ABP−), and all cells (FIG. 10). Community composition was then determined for each population by amplicon sequencing of the 16S rRNA gene, and differentially abundant taxa were identified both via paired quantitative analysis and presence/absence analysis. Taxa with statistically increased abundance in the GlcA-ABP+ fraction compared to the GlcA-ABP− fraction were considered glucuronidase-active. Glucuronidase active taxa were taxonomically diverse, including Bacteroidetes, Proteobacteria, and Tenericutes; however, the majority of the taxa (31/37) were Firmicutes (FIG. 12). The three most abundant GlcA-ABP+ operational taxanomic units (OTUs) were also diverse, representing the families Rikkenellaceae, Anaeroplasmaceae, and Erysipelotrichaceae. By contrast, OTUs with significantly increased abundance in the GlcA-ABP− fraction compared with the GlcA-ABP+ fraction were considered to be glucuronidase-inactive. This fraction was also taxonomically diverse with representative sequences from Bacteroidetes, Proteobacteria, and Firmicutes. Interestingly, the GlcA-ABP-enriched OTU with the highest abundance was a Lachnospiraceae. This highlights a pertinent finding: some taxonomic groups at the level of family or even genus contained both glucuronidase-active and glucuronidase-inactive OTUs. This demonstrates that in vivo metabolic activity cannot be ascribed based solely on phylogenetic similarity.

Figure 13:
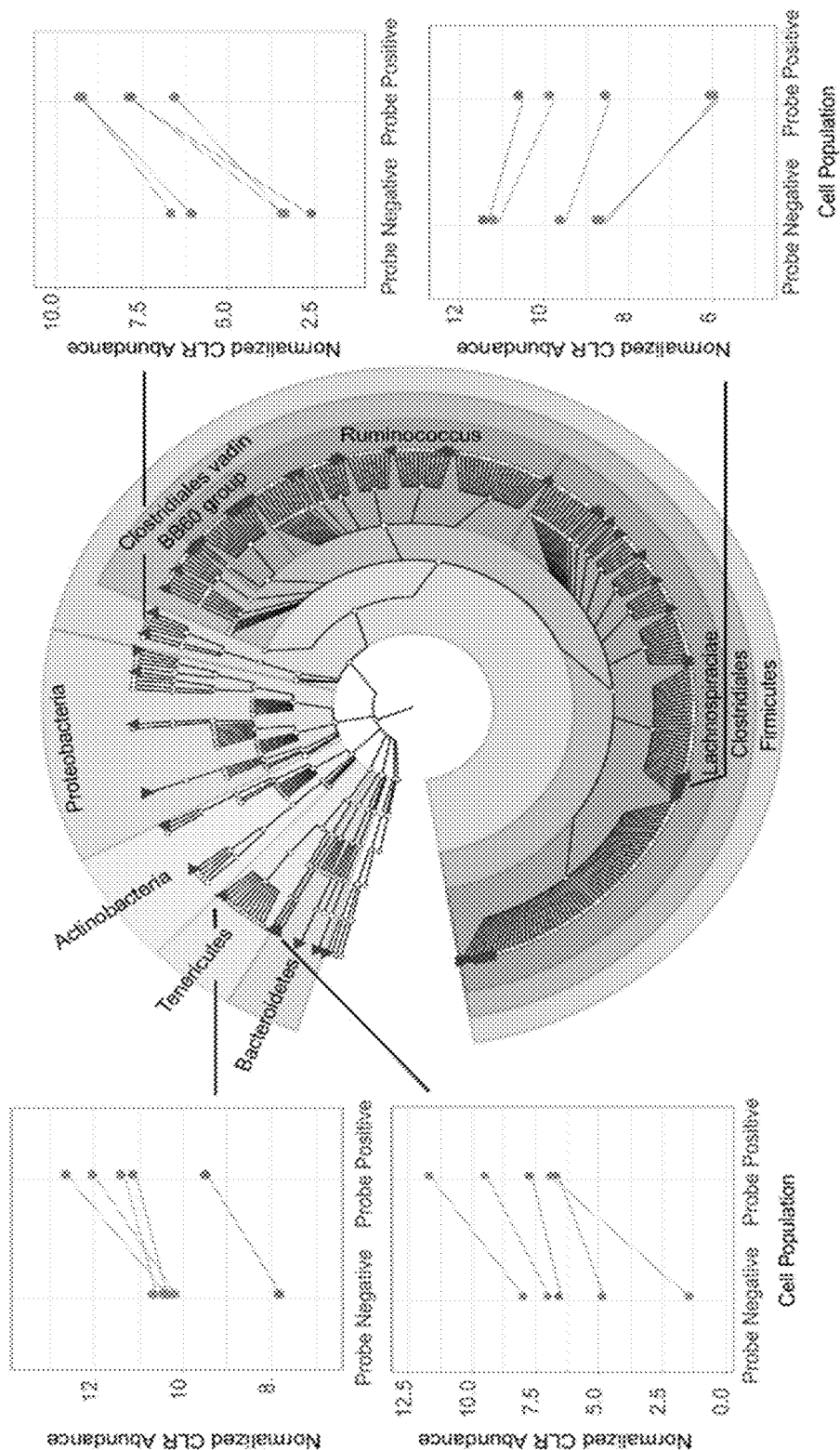
FIG. 13 shows a phylogenetic distribution of GlcA-ABP+ and GlcA-ABP– taxa, wherein triangles indicate taxa with significantly increased abundance in the probe-positive or probe-negative population and circles indicate that no significant differential abundance was observed; examples of three GlcA-ABP+ taxa (left and top right) and one GlcA-ABP– taxon (bottom left) are shown and taxa are considered differentially abundant where Benjamini-Hochberg adjusted p<0.05 by Welch's t test or by G-test (n=5).
Figure 14A:
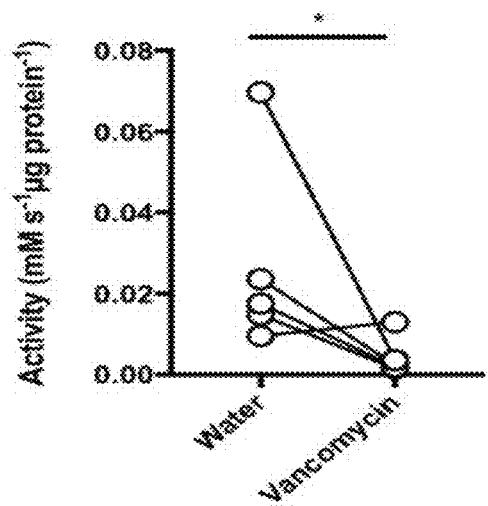
Figure 14B:
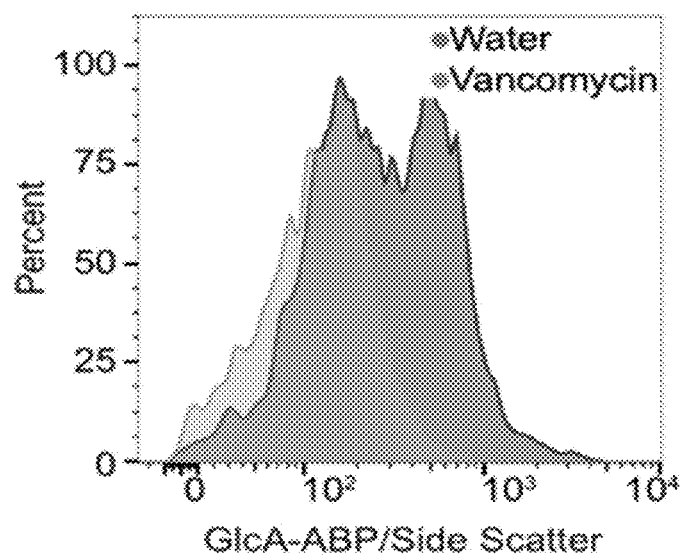
FIG. 14B shows glucuronidase activity in the gut microbiome of control or vancomycin-treated mice, wherein paired littermates (n=5) are connected by lines and * indicates p<0.05 by ratio-paired Student's t-test.

Given that multiple phylogenetically distinct taxa contribute to glucuronidase activity in the gut, disruption of the gut microbiota does not necessarily aborogate glucuronidase activity, but rather the taxa responsible could change this activity. Pairs of littermates were exposed to water with or without vancomycin, an antibiotic known to target Firmicutes in the gut microbiota (FIG. 12). As Firmicutes made up most the probe-positive taxa in the non-treated mice (FIG. 13), vancomycin treatment may shift the GlcA-ABP+ population composition. Vancomycin treatment reduced, but did not eliminate, glucuronidase activity in 4 of 5 sets of littermates (FIG. 14A). Accordingly, the intensity of GlcA-ABP+ labeling decreased as well (FIG. 14B).

Figure 14C:
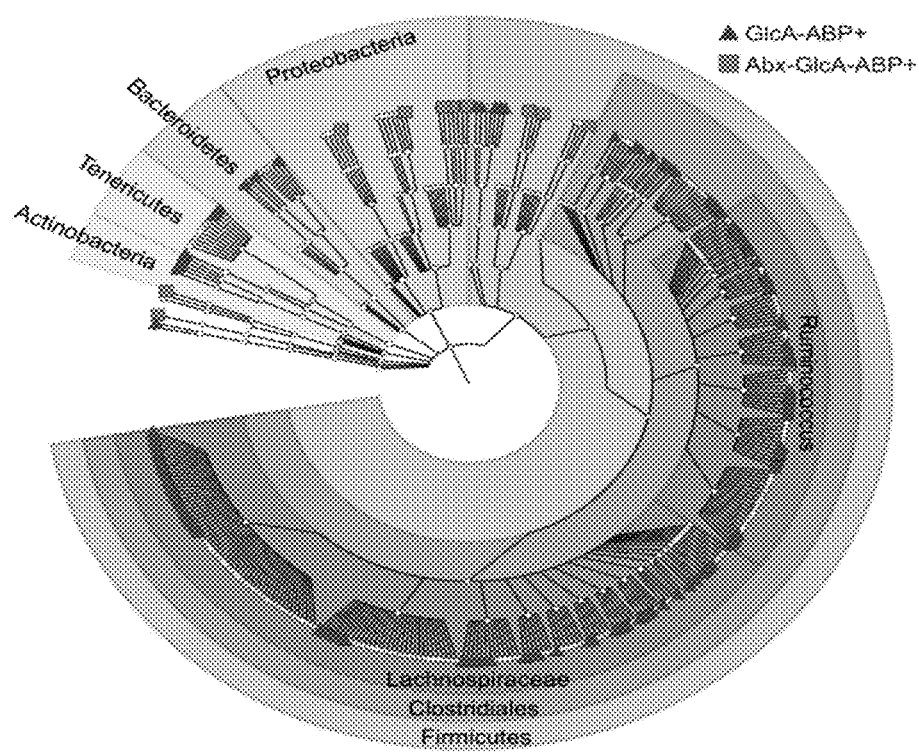
FIG. 14C shows a comparison of GlcA-ABP+ populations in untreated (water) and vancomycin-treated mice.
Figure 15:
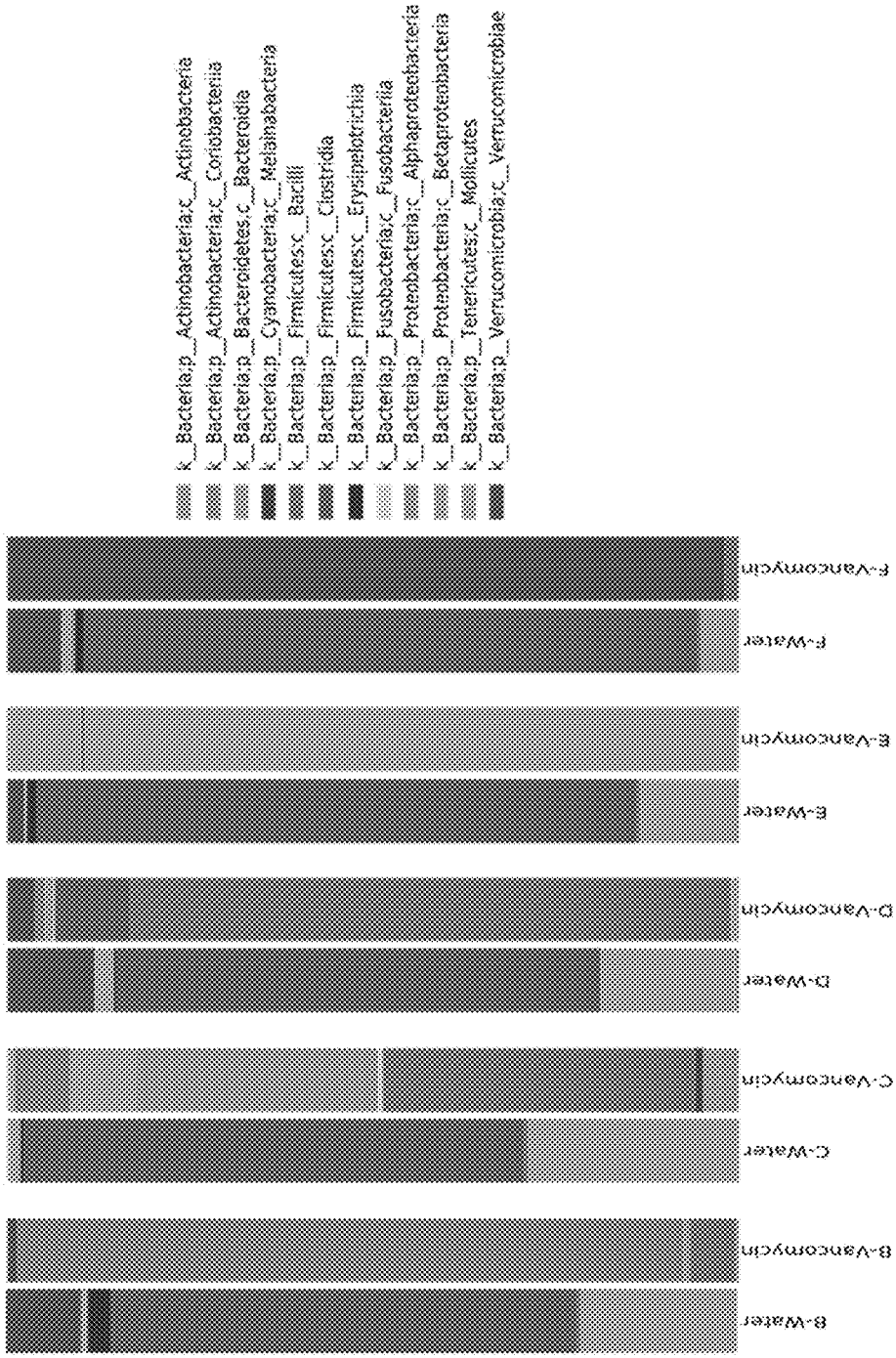
FIG. 15 shows a population shift upon vancomycin treatment for each littermate pair.

To identify the glucuronidase-active taxa that shift following antibiotic treatment, the GlcA-ABP+ populations of vancomycin-treated (Abx-GlcA-ABP+) and untreated (GlcA-ABP+) littermates were compared. As expected, vancomycin treatment dramatically decreased the relative abundance of Firmicutes with a corresponding increase in the relative abundance of Proteobacteria, Verrucomicrobia, and Bacteroidetes (FIG. 15). Compared with the vancomycin-treated GlcA-ABP+ population, the control GlcA-ABP+ population was significantly enriched in OTUs from the Firmicutes (specifically Clostridiales), Bacteroidetes, Tenericutes, and Actinobacteria phyla (FIG. 14C). In contrast, the Abx-GlcA-ABP+ population was significantly enriched in OTUs belonging to the Proteobacteria; additionally, two *Lactobacillus* taxa were also significantly more abundant in the GlcA-ABP+ population following antibiotic treatment. The ability of such disparate taxa to elicit the same function under different conditions (i.e., antibiotic perturbation) demonstrates the substrate diversity and utility of these enzymes. The binding of glucuronides to β-glucuronidases is primarily mediated by the glucuronic acid rather than the metabolite, allowing microbes to extract carbon and energy in the form of glucuronic acid from multiple parent metabolites.

Thus, β-glucuronidases exhibit a high degree of functional redundancy by being both genetically widespread and capable of hydrolyzing multiple substrates. As a result, perturbation of community structure may change the composition of a functional guild without entirely eliminating the function. These data demonstrate that therapeutic manipulation of deglucuronidation activity in the gut requires targeting enzymes from multiple gut taxa. While genetic prediction and in vitro analysis of gut microbiota isolates previously suggested this result, the compositions and methods herein confirm biochemical activity at the molecular scale in the microbiome through coupling detection of in situ activity with the ability to identify the responsible functional taxa.

Figure 14D:
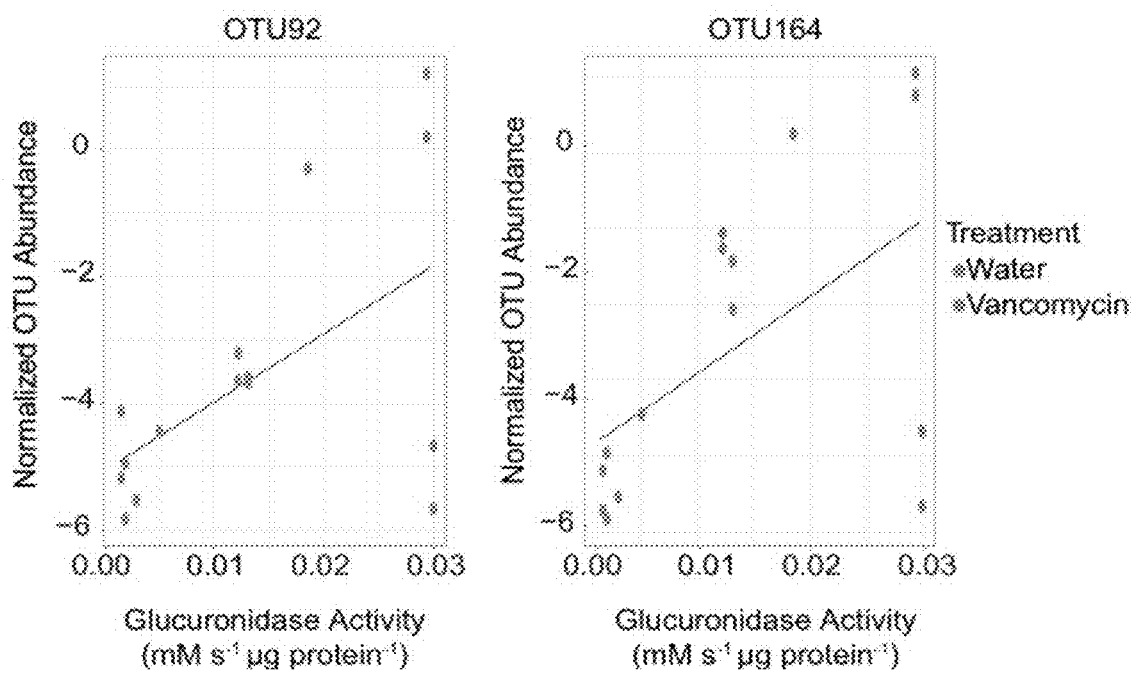
FIG. 14D shows Pearson correlation plots of glucuronidase activity with normalized log abundance for two example OTUs.

To provide further confirm the data, OTUs with an abundance in the total population that positively correlates with glucuronidase activity were identified and compared to the OTUs that were depleted following vancomycin exposure. Twelve OTUs with a significant positive correlation to glucuronidase activity were identified. Two examples are shown, OTU92, corresponding to the Clostridiales, and OTU164, corresponding to the Ruminococcus (FIG. 14D). Of the 12 OTUs, 10 were significantly more abundant in the GlcA-ABP+ population than in the Abx-GlcA-ABP+ population (FIG. 14C), suggesting that these taxa were responsible for the glucuronidase activity in the untreated mice and are reduced upon vancomycin exposure. Of the remaining two OTUs, one was only found in a single sample across the GlcA-ABP+ and Abx-GlcA-ABP+, preventing statistical analysis.

The remaining OTU is an Akkermansia OTU. A dramatic increase in Akkermansia was observed in one of the vancomycin-treated mice (Set F), which was also the only litter pair to exhibit increased glucuronidase activity after antibiotic treatment. These findings show functional plasticity or redundancy among metabolically active subpopulations of the gut microbiome, and accessing this experimental information requires functional assays, such as provided by the compositions and methods disclosed herein.

In view of the many possible embodiments to which the principles of the present disclosure may be applied, it should be recognized that the illustrated embodiments are only examples and should not be taken as limiting. Rather, the scope of the present disclosure is defined by the following claims. We therefore claim as our invention all that comes within the scope and spirit of these claims.

We claim:

1. A probe having a structure satisfying a formula selected from:

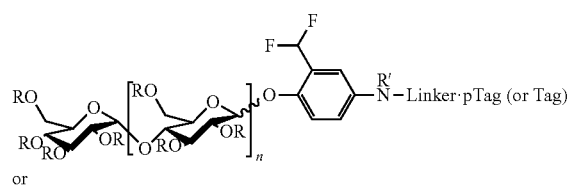

or

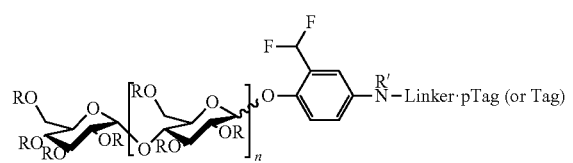

wherein the linker is an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; pTag is an azide or an alkyne or Tag is a detectable moiety; each R independently is hydrogen, aliphatic, or a protecting group; R' is hydrogen, aliphatic, heteroaliphatic, or aromatic; and n is a integer selected from 2 to 10.

2. The probe of claim 1, wherein the bi-functional linker is selected from:

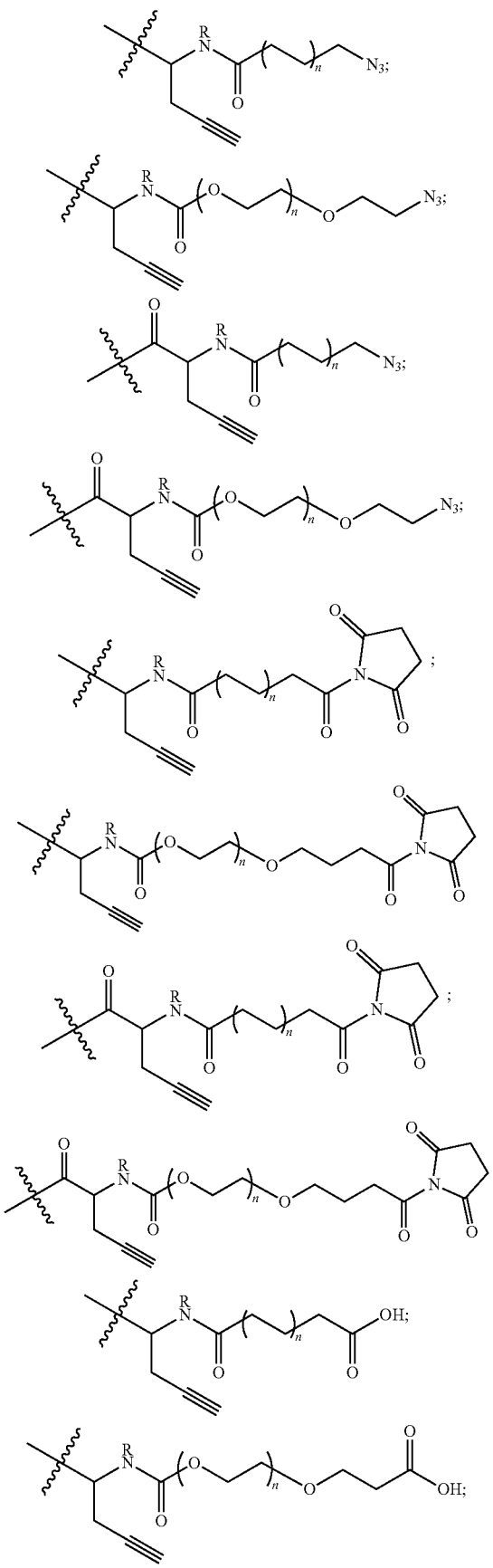

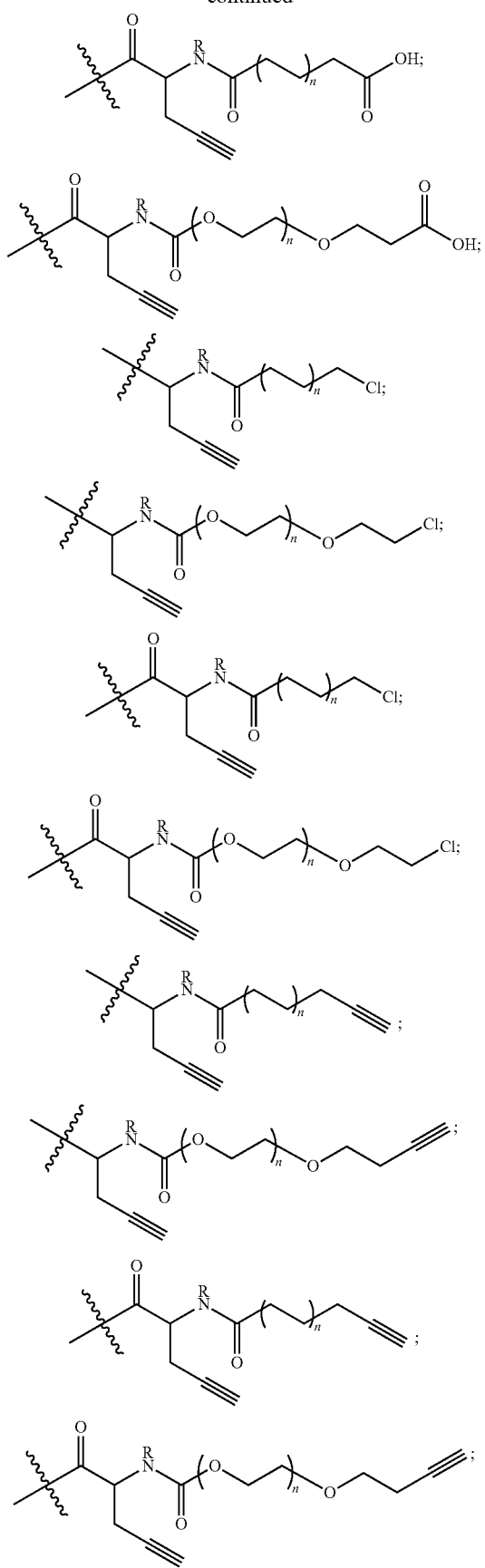
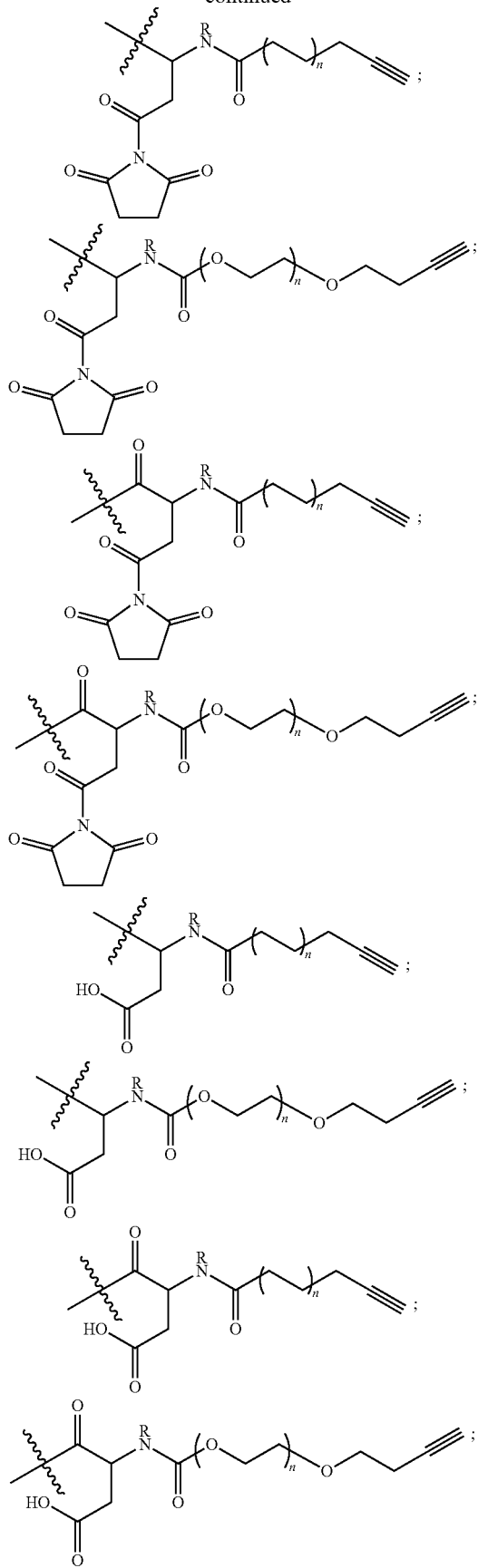

117
-continued
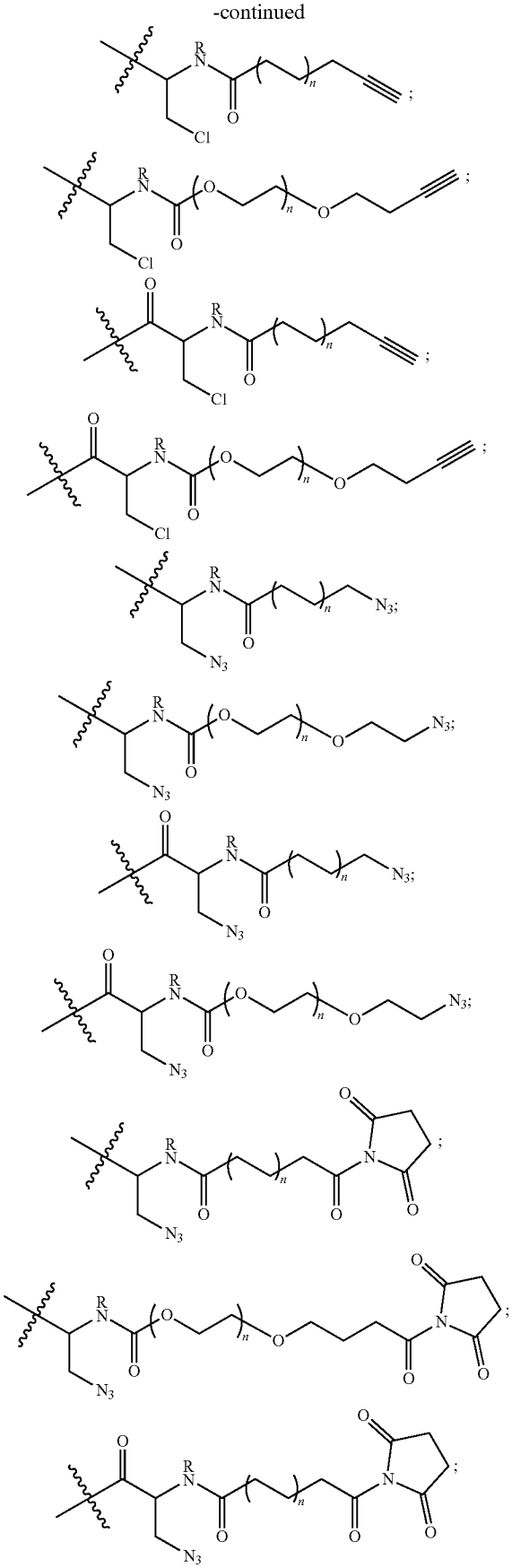
118
-continued
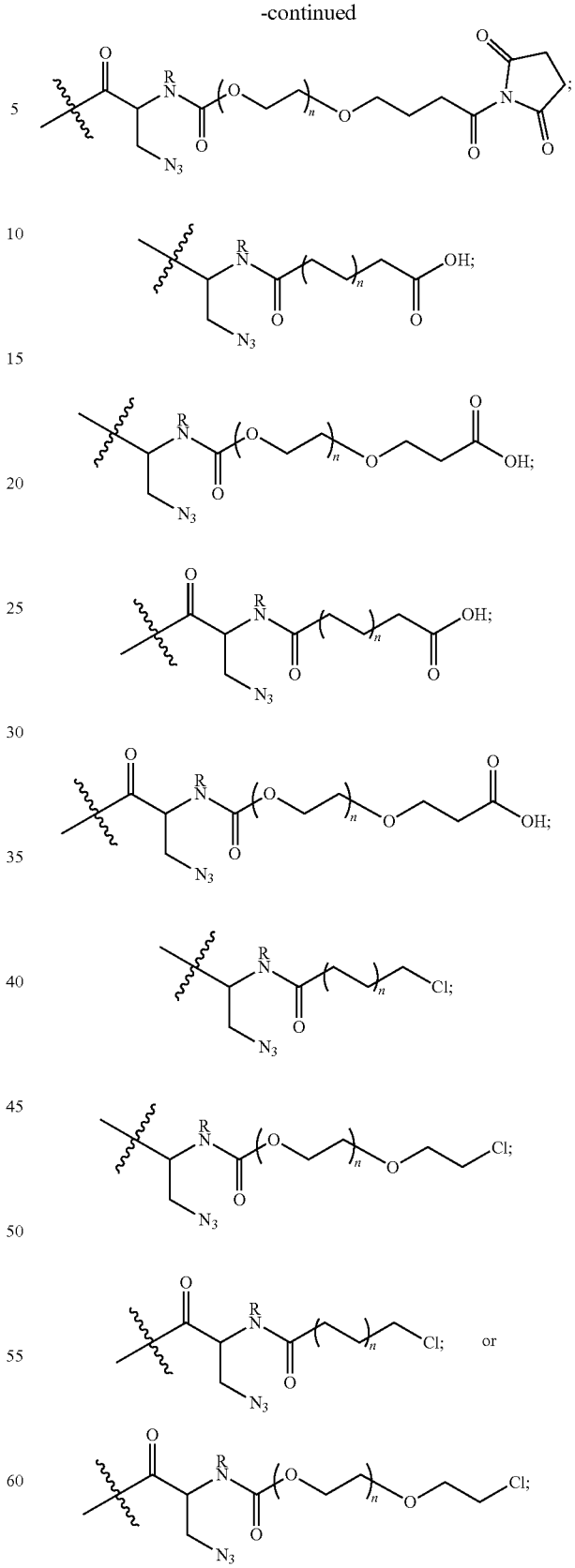
wherein R is hydrogen, aliphatic, heteroaliphatic, or aromatic; and n is an integer ranging from 0 to 20.

3. The probe of claim 1, wherein the probe is selected from:
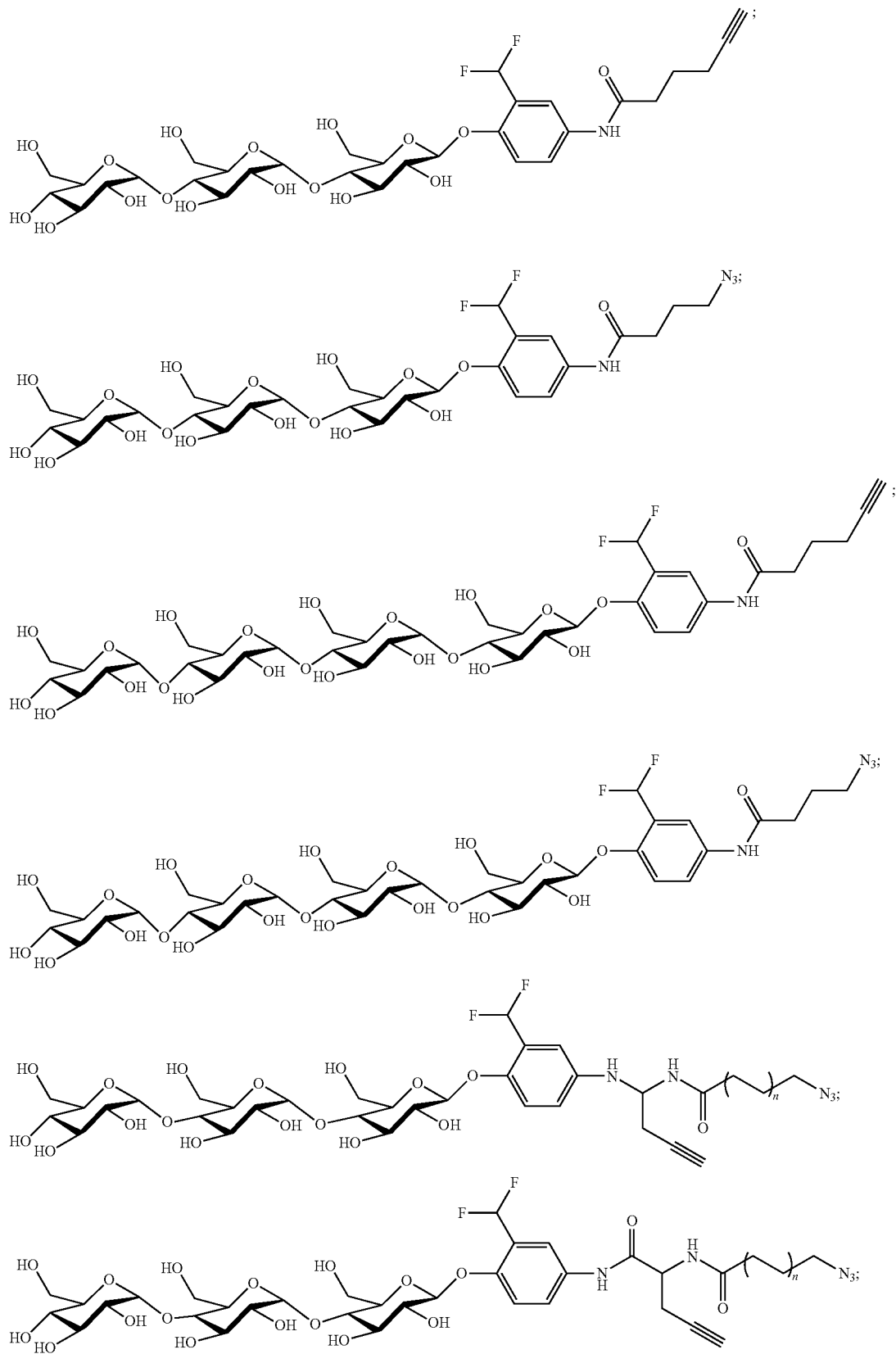

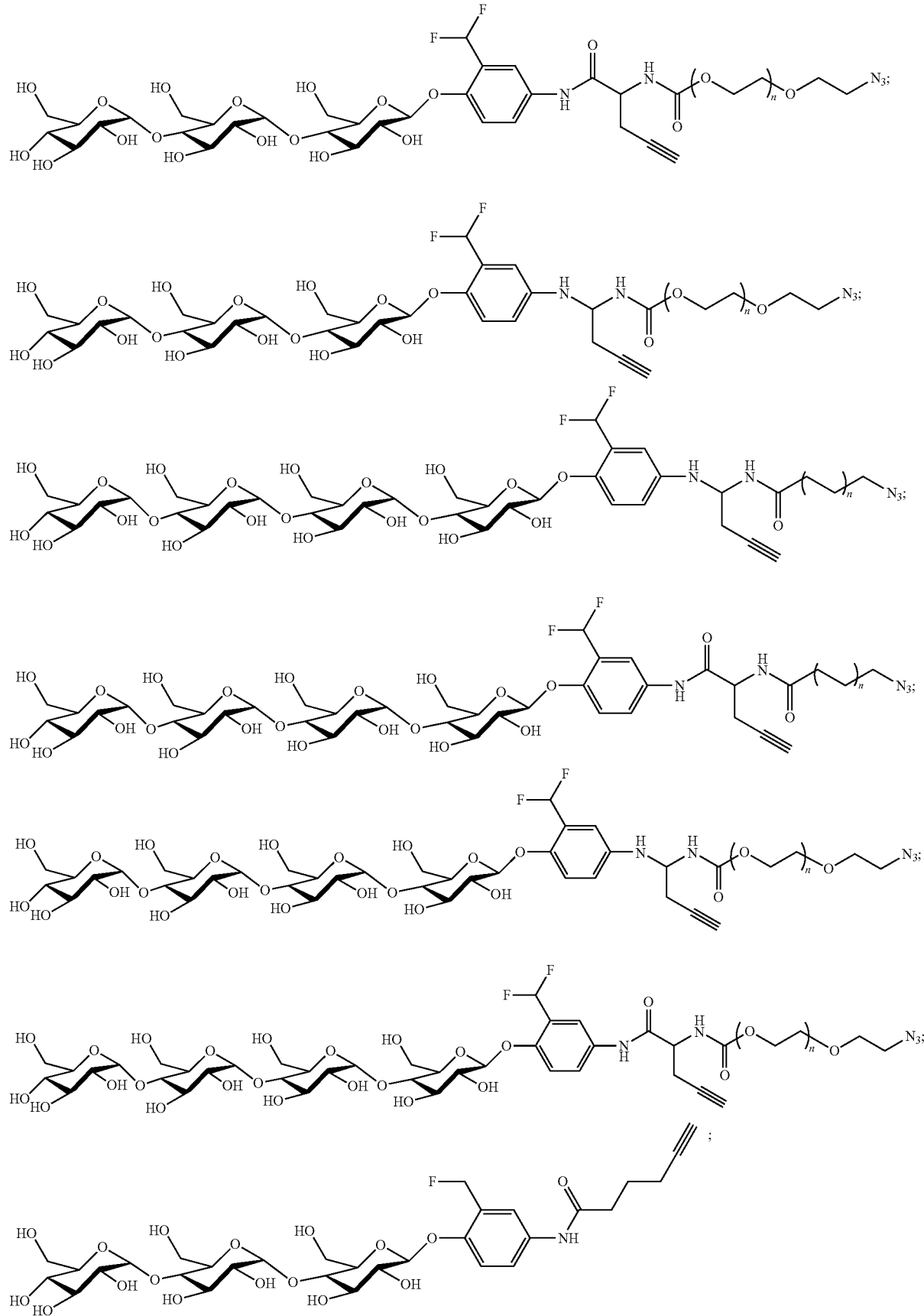

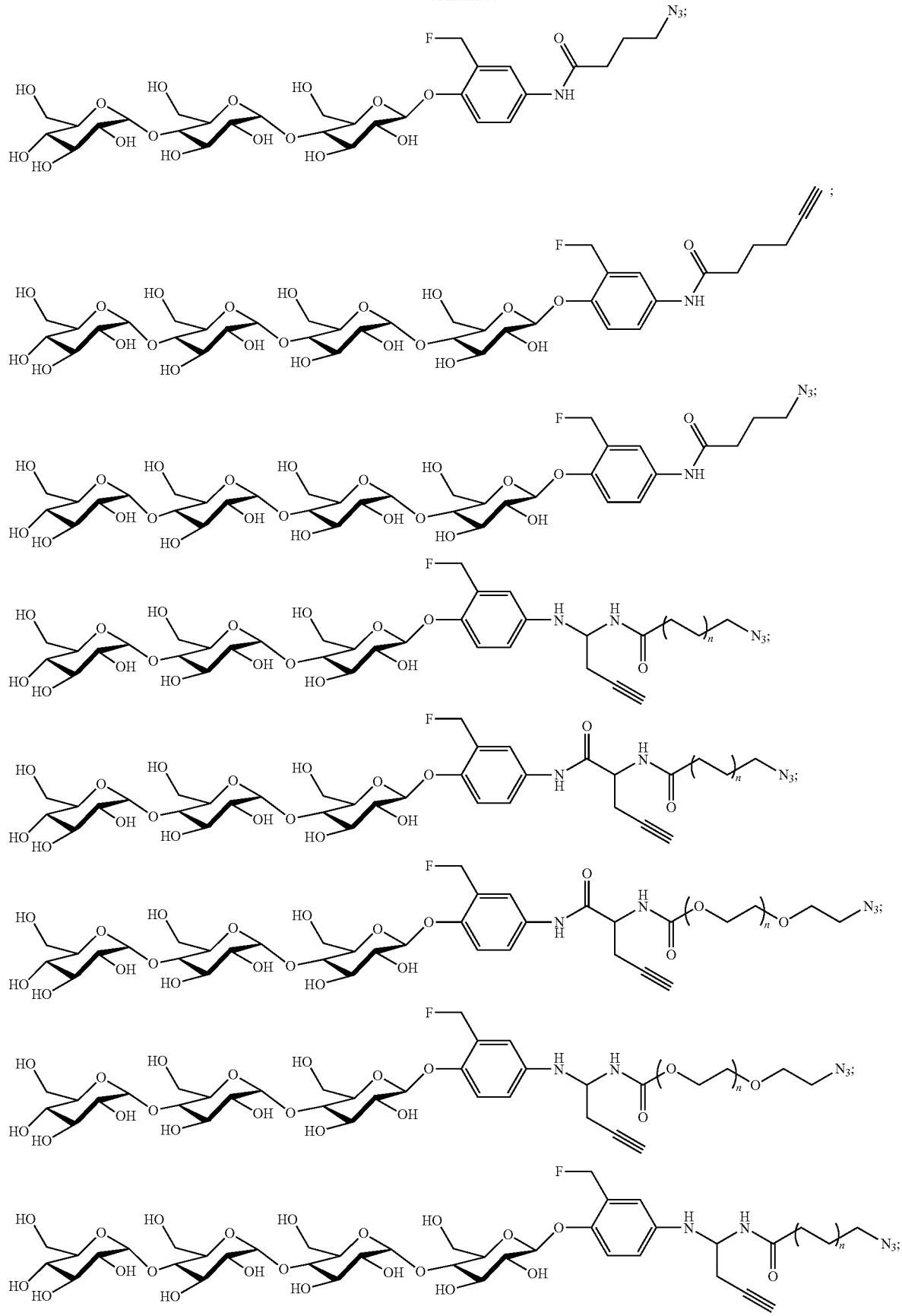

-continued

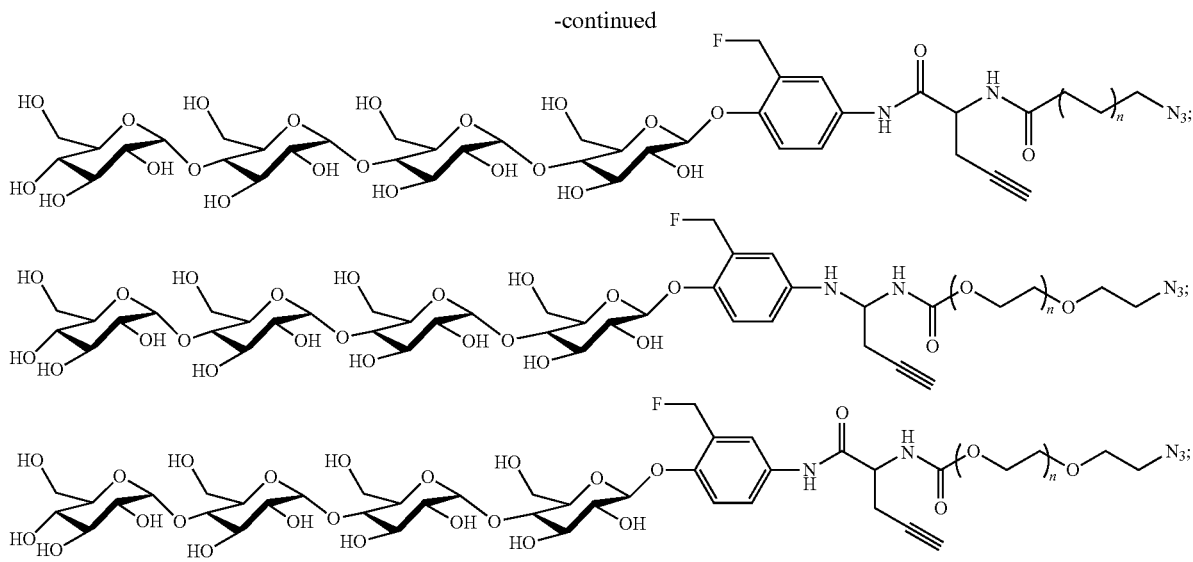

wherein each R independently is H, aliphatic, aromatic, or a combination of aliphatic and aromatic, or a counterion that balance a negative charge on the corresponding oxygen atom.

4. A kit, comprising:
a substrate; and
a probe having a structure satisfying a formula selected from

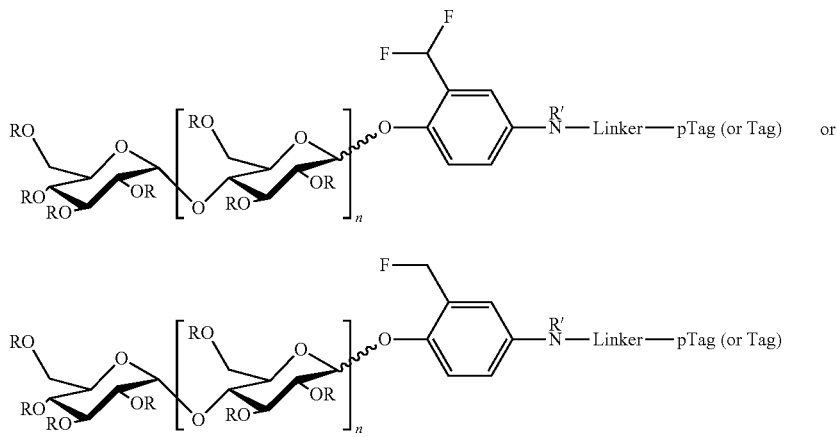

wherein the linker is a bi-functional linker comprising an anchor group; pTag is an azide or alkyne or Tag is a detectable moiety; each R independently is hydrogen, aliphatic, or a protecting group; R' is hydrogen, aliphatic, heteroaliphatic, or aromatic; and n is a integer selected from 2; to 10 and wherein the substrate comprises a surface modified with a functional group configured to covalently bind with the anchor group of the probe.

5. The kit of claim 4, wherein the surface of the substrate is modified with an azide or an alkyne and wherein the anchor group is an azide or an alkyne and the substrate is covalently bound to the probe by a triazole ring formed between the azide or the alkyne of the substrate and the alkyne or the azide, respectively, of the anchor group of the probe.

6. The kit of claim 4, wherein the substrate is a glass plate, a glass well-plate, a glass rod, or a glass microsphere.

7. The kit of claim 4, wherein the probe comprises a pTag group and the kit further comprises a reagent comprising a detectable moiety configured to covalently bind with the pTag group.

8. A method, comprising exposing a sample to the probe of claim 1 to label at least one analyte present in the sample with the probe thereby forming a probe-analyte conjugate.

9. The method of claim 8, wherein the method further comprises:
(i) exposing the sample to an energy source to promote formation of the probe-analyte conjugate;
(ii) exposing the sample to a reagent comprising a detectable moiety configured to covalently bind with a pTag group of the probe;
(iii) sorting or isolating the probe-analyte conjugate or a microbe comprising the probe-analyte conjugate;
(iv) identifying the analyte or the microbe with the probe-analyte conjugate; or
(v) any combination of (i)-(iv).

10. A method of altering microbial metabolism in an environment, comprising:
    exposing a sample from the environment to the probe of claim 1;
    allowing the probe to interact with at least one microbial protein present in the sample, wherein the at least one microbial protein comprises at least one specific metabolic function;
    determining the presence of the at least one microbial protein in the sample that is bound to the probe;
    evaluating the activity of the at least one microbial protein bound to the probe; and
    altering microbial metabolism in the environment by:
        enriching the environment with the at least one microbial protein or a microbe containing the at least one microbial protein;
        reducing the amount of the at least one microbial protein or an amount of a microbe containing the at least one microbial protein in the environment;
        increasing the at least one specific metabolic function; or
        reducing the at least one specific metabolic function.

11. The method of claim 10, wherein the at least one specific metabolic function comprises nutrient cycling, bioremediation, or producing biofuel or bioenergy;
    and wherein the at least one microbial protein is a cellulase, hemicellulase, xylanase, glucosidase, sulfatase, phosphatase, protease, lytic polysaccharide monooxygenase (LPMO), or chitinase.

12. A method, comprising exposing a sample to the kit of claim 4 to label at least one analyte present in the sample with the probe of the kit thereby forming a probe-analyte conjugate.

13. The method of claim 12, wherein the method further comprises:
    (i) exposing the sample to an energy source to promote formation of the probe-analyte conjugate;
    (ii) exposing the sample to a reagent comprising a detectable moiety configured to covalently bind with a pTag group of the probe;
    (iii) sorting or isolating the probe-analyte conjugate or a microbe comprising the probe-analyte conjugate;
    (iv) identifying the analyte or the microbe with the probe-analyte conjugate; or
    (v) any combination of (i)-(iv).

14. A method of altering microbial metabolism in an environment, comprising:
    exposing a sample from the environment to the kit of claim 4;
    allowing the probe to interact with at least one microbial protein present in the sample, wherein the at least one microbial protein comprises at least one specific metabolic function;
    determining the presence of the at least one microbial protein in the sample that is bound to the probe;
    evaluating the activity of the at least one microbial protein bound to the probe; and
    altering microbial metabolism in the environment by:
        enriching the environment with the at least one microbial protein or a microbe containing the at least one microbial protein;
        reducing the amount of the at least one microbial protein or an amount of a microbe containing the at least one microbial protein in the environment;
        increasing the at least one specific metabolic function; or
        reducing the at least one specific metabolic function.

15. The method of claim 14, wherein the at least one specific metabolic function comprises nutrient cycling, bioremediation, or producing biofuel or bioenergy.

16. The method of claim 14, wherein the at least one microbial protein is a cellulase, hemicellulase, xylanase, glucosidase, sulfatase, phosphatase, protease, lytic polysaccharide monooxygenase (LPMO), or chitinase.

17. A probe having a structure satisfying a formula selected from:

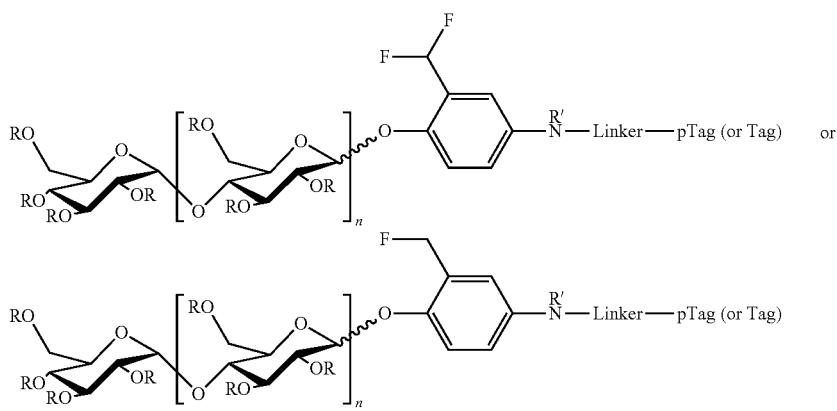

wherein the linker is an aliphatic group, a heteroaliphatic group, an aromatic group, an aliphatic-aromatic group, a heteroaliphatic-aromatic group, a heteroaromatic group, an aliphatic-heteroaromatic group, a heteroaliphatic-heteroaromatic group, or a bi-functional linker; pTag is an alkyne or an azide, or Tag is a detectable moiety; each R independently is hydrogen, aliphatic, or a protecting group; R' is hydrogen, aliphatic, heteroaliphatic, or aromatic; and n is 2 or 3.

* * * * *